US012571031B2

(12) United States Patent
Shi et al.

(10) Patent No.: US 12,571,031 B2
(45) Date of Patent: Mar. 10, 2026

(54) NUCLEIC ACID MODIFYING REAGENTS AND USES THEREOF

(71) Applicant: Promega Corporation, Madison, WI (US)

(72) Inventors: Ce Shi, Madison, WI (US); Nathan Feirer, Madison, WI (US); Michael A. Scurria, Madison, WI (US); Subhanjan Mondal, Madison, WI (US); Said A. Goueli, Madison, WI (US); Thomas Kirkland, Madison, WI (US); James J. Cali, Madison, WI (US); Poncho Meisenheimer, Madison, WI (US)

(73) Assignee: Promega Corporation, Madison, WI (US)

( * ) Notice: Subject to any disclaimer, the term of this patent is extended or adjusted under 35 U.S.C. 154(b) by 1217 days.

(21) Appl. No.: 17/464,476

(22) Filed: Sep. 1, 2021

(65) Prior Publication Data

US 2022/0064710 A1 Mar. 3, 2022

Related U.S. Application Data

(60) Provisional application No. 63/073,787, filed on Sep. 2, 2020.

(51) Int. Cl.

| | |
|---|---|
| ***C12Q 1/68*** | (2018.01) |
| ***C07D 221/12*** | (2006.01) |
| ***C07D 403/04*** | (2006.01) |
| ***C07D 513/06*** | (2006.01) |
| ***C07F 15/00*** | (2006.01) |
| ***C12Q 1/686*** | (2018.01) |
| ***C12Q 1/689*** | (2018.01) |
| ***C12Q 1/70*** | (2006.01) |

(52) U.S. Cl.

CPC ........... *C12Q 1/686* (2013.01); *C07D 221/12* (2013.01); *C07D 403/04* (2013.01); *C07D 513/06* (2013.01); *C07F 15/0093* (2013.01); *C12Q 1/689* (2013.01); *C12Q 1/701* (2013.01)

(58) Field of Classification Search

CPC ...... C12Q 1/686; C12Q 1/689; C07D 221/12; C07D 403/04; C07D 513/06; C07F 15/0093

See application file for complete search history.

(56) References Cited

U.S. PATENT DOCUMENTS

| | | | |
|---|---|---|---|
| 7,262,009 | B2 | 8/2007 | Rudi |
| 7,776,567 | B2 | 8/2010 | Mao et al. |
| 7,803,943 | B2 | 9/2010 | Mao et al. |
| 9,206,474 | B2 | 12/2015 | Mcdougall et al. |
| 2018/0142283 | A1 | 5/2018 | Mao et al. |

FOREIGN PATENT DOCUMENTS

| | | |
|---|---|---|
| WO | WO-2007100762 A2 | 9/2007 |
| WO | WO-2014005125 A2 | 1/2014 |
| WO | WO 2015/009678 | 1/2015 |
| WO | WO 2015/116867 | 8/2015 |
| WO | WO 2016/011348 | 1/2016 |
| WO | WO 2020/167811 | 8/2020 |

OTHER PUBLICATIONS

International Search Report and Written Opinion for PCT/US2021/048725. Mailed Jan. 4, 2022. 15 pages.

Costales et al., A Designed Small Molecule Inhibitor of a Non-Coding RNA Sensitizes HER2 Negative Cancers to Herceptin. J Am Chem Soc. Feb. 20, 2019;141(7):2960-2974.

Egorova et al., Biological Activity of Ionic Liquids and Their Application in Pharmaceutics and Medicine. Chem Rev. May 24, 2017;117(10):7132-7189.

Emerson et al., Schrödinger's microbes: Tools for distinguishing the living from the dead in microbial ecosystems. Microbiome. Aug. 16, 2017;5(1):86. 23 pages.

Immanuel et al., Discrimination between viable and dead Xanthomonas fragariae in strawberry using viability PCR. Journal of Phytopathology , vol. 168, No. 6, 2020, pp. 363-373.

Mustafa et al., Novel No-Wash Luminogenic Probes for the Detection of Transporter Uptake Activity. Bioconjug Chem. Jan. 20, 2016;27(1):87-101.

Nocker et al., Comparison of propidium monoazide with ethidium monoazide for differentiation of live vs. dead bacteria by selective removal of DNA from dead cells. J Microbiol Methods. Nov. 2006;67(2):310-20.

Nogva et al., Ethidium monoazide for DNA-based differentiation of viable and dead bacteria by 5'-nuclease PCR. Biotechniques. Apr. 2003;34(4):804-8, 810, 812-3.

Valu et al., DNA-directed alkylating agents. 3. Structure-activity relationships for acridine-linked aniline mustards: consequences of varying the length of the linker chain. J Med Chem. Nov. 1990;33(11):3014-9.

Gravatt G.L., et al., DNA-Directed Alkylating Agents. 6. Synthesis and Antitumor Activity of DNA Minor Groove-targeted Aniline Mustard Analogues of Pibenzimol (Hoechst 33258), Journal of Medicinal Chemistry, 1994, vol. 37, No. 25, pp. 4338-4345.

Loskotova H., et al., "DNA Interactions of Cisplatin Tethered to the DNA Minor Groove Binder Distamycin", European Journal of Biochemistry, 1999, vol. 266, No. 2, pp. 392-402.

(Continued)

*Primary Examiner* — Jezia Riley

(74) *Attorney, Agent, or Firm* — Casimir Jones, S.C.; Anne M. Reynolds

(57) ABSTRACT

The present disclosure includes compounds, compositions, and methods for nucleic acid amplification reactions. In particular, the present disclosure provides compounds, compositions, and methods for viability PCR (vPCR) applications, in which the compounds that selectively bind to nucleic acids from non-viable cells.

13 Claims, 9 Drawing Sheets

(56) References Cited

OTHER PUBLICATIONS

Santisteban M.S., et al., "Fluorescence Image Cytometry of Nuclear DNA Content Versus Chromatin Pattern: a Comparative Study of Ten Fluorochromes", The Journal of Histochemistry and Cytochemistry, 1992, vol. 40, No. 11, pp. 1789-1797.

Su D., et al., "Antibody-Drug Conjugate Derived from Cytotoxic Seco-CBI-Dimer Payloads Are Highly Efficacious in Xenograft Models and Form Protein Adducts in Vivo", Bioconjugate Chemistry, 2019, vol. 30, No. 5, pp. 1356-1370.

Vlahov I.R., et al., "Latent Warheads for Targeted Cancer Therapy: Design and Synthesis of Pro- Pyrrolobenzodiazepines and Conjugates", Bioconjugate Chemistry, 2017, vol. 28, No. 12, pp. 2921-2931, 11 Pages.

NUCLEIC ACID MODIFYING REAGENTS AND USES THEREOF

CROSS-REFERENCE TO RELATED APPLICATIONS

The present application claims priority to and the benefit of U.S. Provisional Patent Application No. 63/073,787, filed Sep. 2, 2020, which is incorporated herein by reference in its entirety.

FIELD

Provided herein are compounds, compositions, kits, and methods for DNA amplification reactions. In particular, the present disclosure provides compounds that can spontaneously modify nucleic acids from non-viable cells, and corresponding methods for selectively detecting nucleic acids from viable cells via amplification, such as polymerase chain reaction (PCR) and isothermal amplification methods.

BACKGROUND

Nucleic acid-based analytical methods, ranging from species-specific PCR to metagenomics, have greatly expanded our understanding of microbiological diversity in natural samples. However, cell viability cannot easily be assessed by standard DNA-targeted methods such as PCR or qPCR and isothermal amplification methods.

Propidium monoazide (PMA) has been shown to differentiate DNA associated with viable cells from DNA associated with non-viable cells, in a technique known as viability PCR (vPCR). In a sample having both live and dead cells, PMA can access the DNA from the dead cells owing to the compromised cell membrane. PMA has a photoreactive azide moiety that covalently modifies DNA upon photolysis, rendering the DNA unable to serve as a template in an amplification reaction. After the photoactivation step, lysis of the remaining viable cells exposes their DNA to allow for amplification. However, variations in light spectrum and intensity can result in sample-to-sample variability, particularly in complex, turbid samples. These difficulties limit the broad utilization and adoption of the vPCR technique.

SUMMARY

Provided herein are compounds, compositions, kits, and methods for DNA amplification reactions. In particular, the present disclosure provides compounds that can spontaneously modify nucleic acids from non-viable cells, and corresponding methods for selectively detecting nucleic acids from viable cells via amplification, such as polymerase chain reaction (PCR) and isothermal amplification methods.

In one aspect, provided herein is a compound or a salt thereof, the compound comprising:

(A) a nucleic acid binding moiety ("NAB moiety");

(B) a live/dead cell differentiating moiety ("LDCD moiety"); and (C) a nucleic acid modifying moiety ("NAM moiety").

In some embodiments, the compound has the structure:

A-B-C wherein A is the NAB moiety, B is the LDCD moiety, C is the nucleic acid modifying moiety. In some embodiments, the compound has more than one NAB moiety, more than one LDCD moiety, and/or more than one NAM moiety. In some embodiments, the NAB moiety is a groove-binding moiety, an intercalating moiety, or a mixed-mode binding moiety. In some embodiments, the NAB moiety comprises a bibenzimidazole moiety or a phenylphenanthridium moiety. In some embodiments, the NAB moiety has a structure selected from:

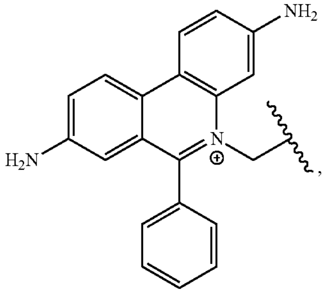

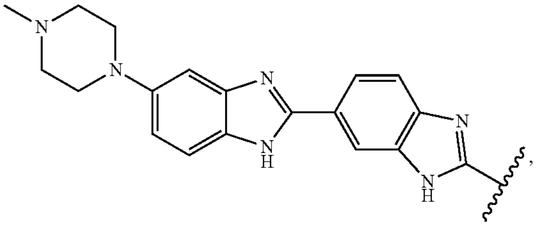

, and

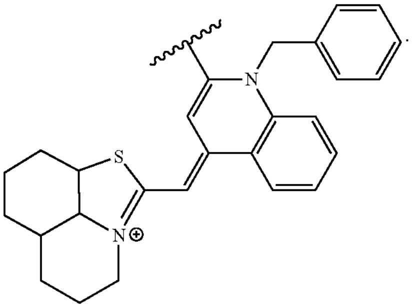

In some embodiments, the NAM moiety comprises a bischloroethylamine (nitrogen mustard) moiety, a platinum-based moiety, a 1-(chloromethyl)-2,3-dihydro-1H-benzo[e]indolyl moiety, or a pyrrolo[2,1-c][1,4]benzodiazepine (PBD) moiety. In some embodiments, the NAM moiety has a structure selected from:

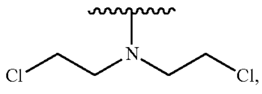

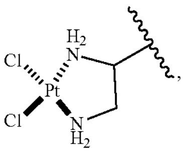

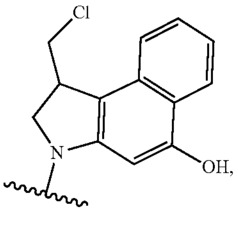

and

-continued

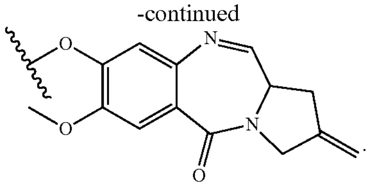

In some embodiments, the LDCD moiety comprises at least one charged moiety. In some embodiments, the LDCD moiety comprises at least one quaternary ammonium group. In some embodiments, the LDCD moiety comprises at least one poly(ethylene glycol) moiety. In some embodiments, the poly(ethylene glycol) moiety has formula: $-(CH_2CH_2O)_n-$, wherein n is 2, 3, 4, 5, 6, 7, 8, 9, or 10. In some embodiments, the LDCD moiety comprises a functional group bound to a solid support. In some embodiments, the LDCD moiety comprises a metabolically cleavable group.

In some embodiments, the compound is selected from:

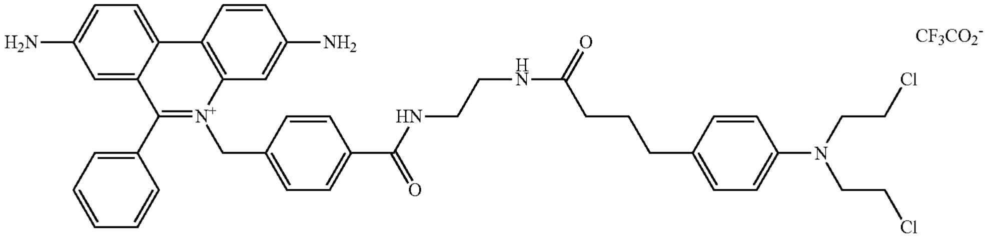

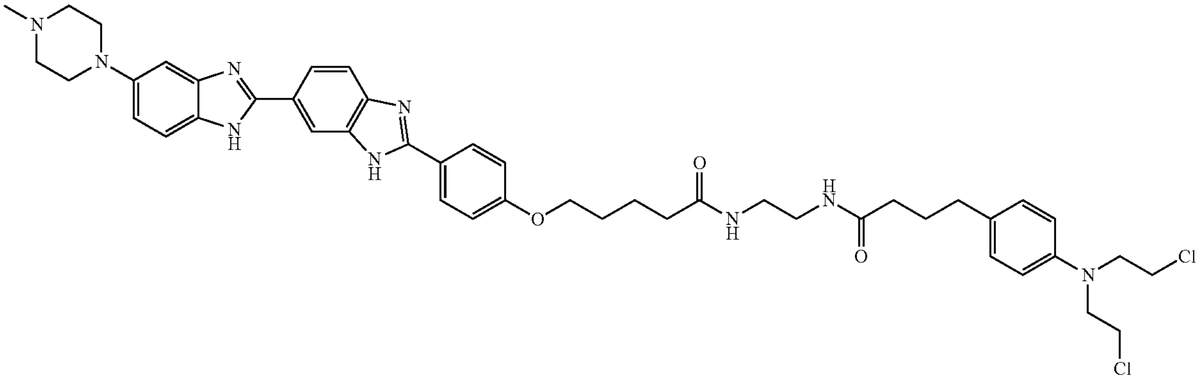

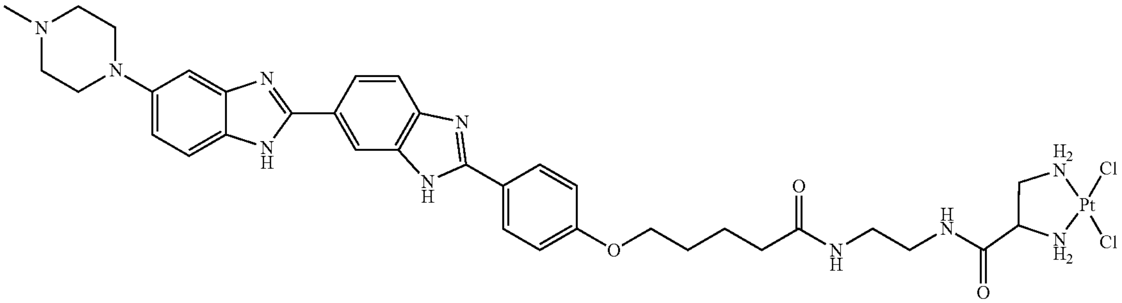

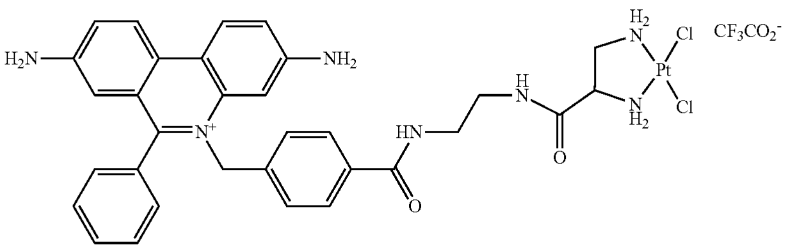

-continued
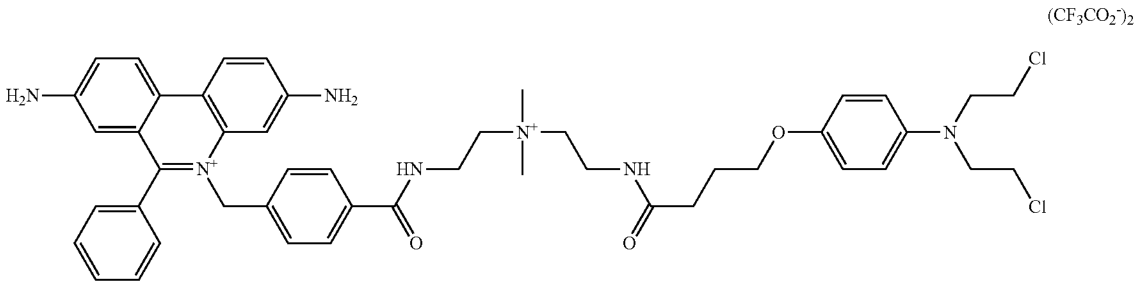
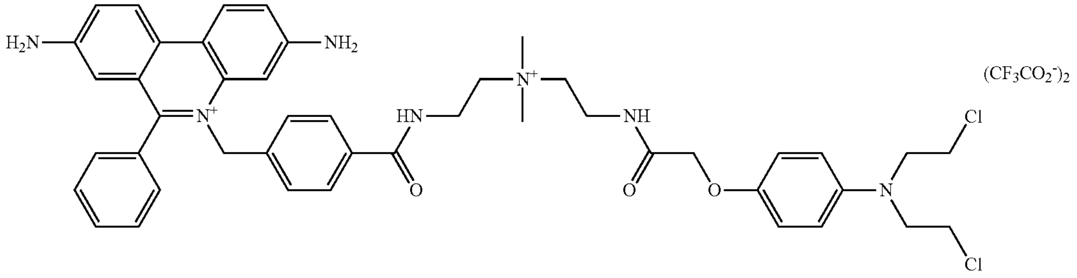
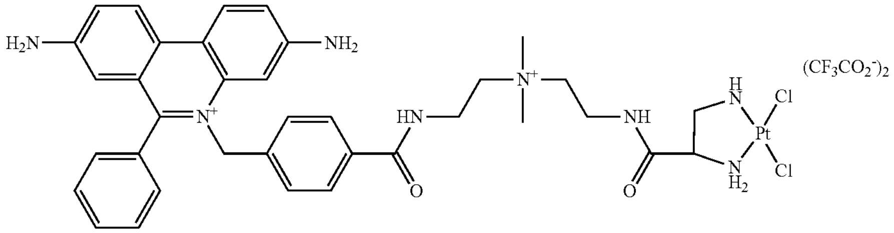
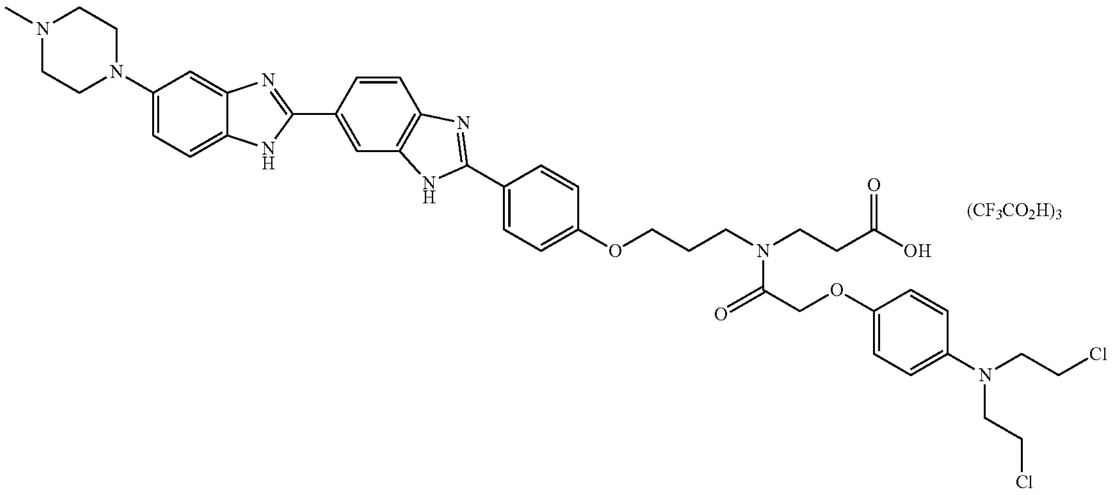

-continued
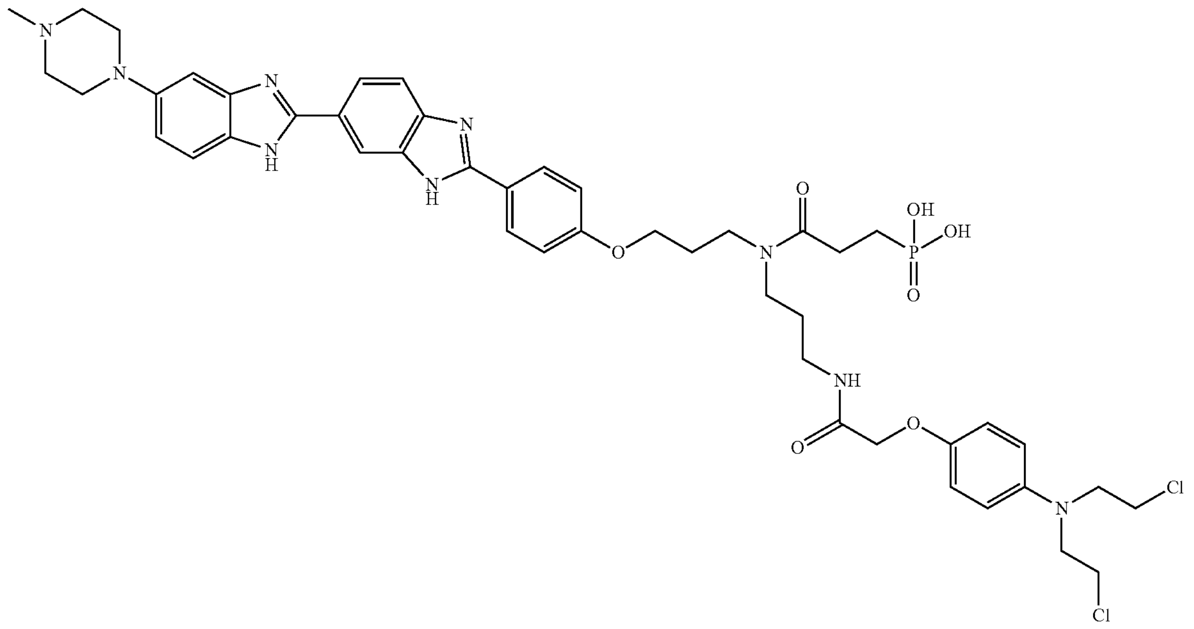
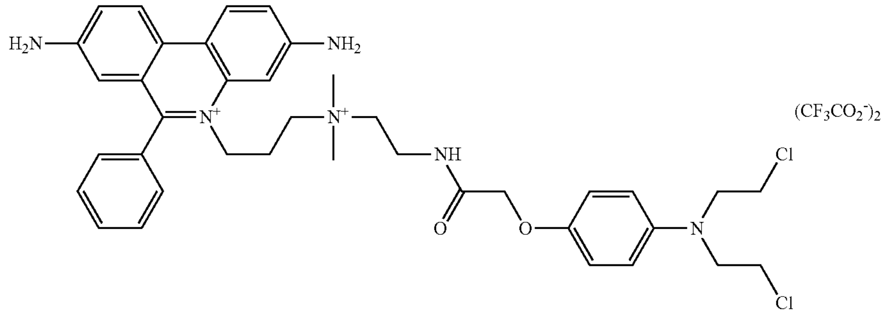
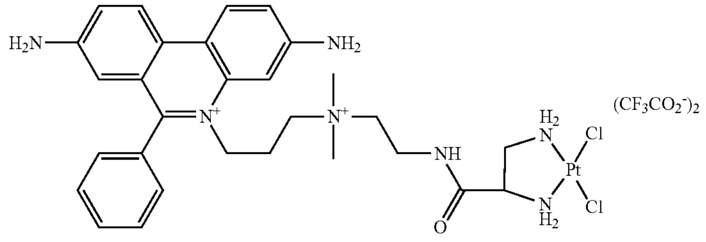
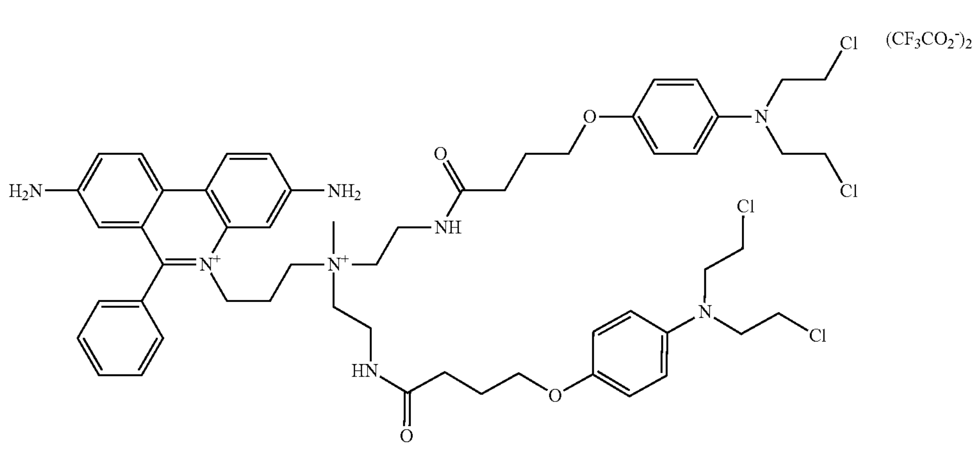
and

-continued

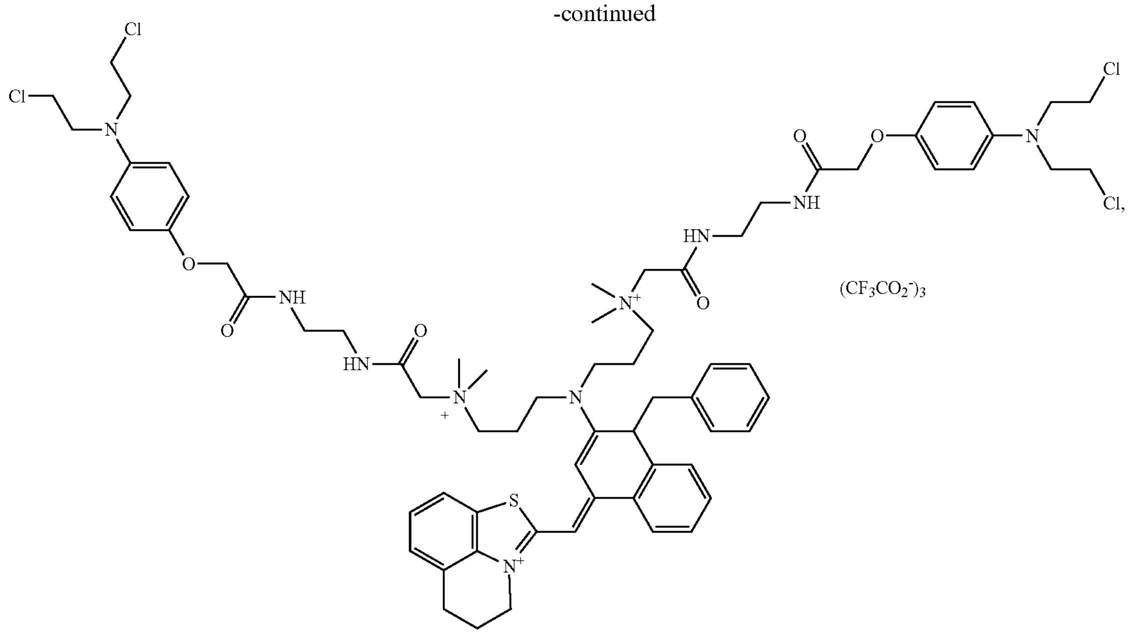

$(CF_3CO_2^-)_3$

In one aspect, provided herein is a method of detecting a viable microorganism or cell in a sample, the method comprising:

(a) contacting the sample with a compound disclosed herein (i.e., a compound having a NAB moiety, a LDCD moiety, and a NAM moiety, or a salt thereof), to form a first mixture;

(b) contacting the first mixture with an inactivating agent to form a second mixture; and (c) amplifying nucleic acids from the second mixture to produce a detectable signal, wherein the signal is indicative of the presence of a viable microorganism or cell in the sample.

In some embodiments, the method does not include a photoactivation step. In some embodiments, the method does not include a culturing step.

In some embodiments, step (a) comprises contacting the sample with the compound or the salt thereof for 5 minutes to 180 minutes. In some embodiments, step (a) comprises contacting the sample with the compound or the salt thereof for 60 minutes to 120 minutes. In some embodiments, step (a) comprises adding to the sample a composition comprising the compound, or a salt thereof, in a solvent. In some embodiments, step (a) further comprises contacting the sample with one or more additional compounds disclosed herein (i.e., a compound having a NAB moiety, a LDCD moiety, and a NAM moiety, or a salt thereof). In some embodiments, the solvent is dimethylsulfoxide. In some embodiments, in step (a), the first mixture comprises the compound at a concentration of 5-100 micromolar.

In some embodiments, the inactivating agent comprises a nucleophile selected from an amine and a thiol. In some embodiments, the inactivating agent is selected from the inactivating agent is selected from cysteine, glutathione, a dNTP, guanine, an amine-containing buffer, and a mixture of any thereof.

In some embodiments, step (c) comprises:

(i) lysing cells in the second mixture to form a lysed sample;

(ii) adding a DNA polymerase and amplification reagents to the lysed sample to form a mixture; and (iii) subjecting the mixture to a thermal cycling protocol to amplify the nucleic acid from the sample.

In some embodiments, the method further comprises a step of removing contaminants and/or cellular debris from the lysed sample, prior to adding the DNA polymerase and amplification reagents. In some embodiments, the method further comprises heating the mixture to a temperature of at least 90° C. to activate the DNA polymerase prior to subjecting the mixture to the thermal cycling protocol.

In some embodiments, the DNA polymerase is a thermostable DNA polymerase selected from Taq, Tbr, Tfi, Tfl, KOD, Tru, Tth, Tli, Tac, Tne, Tma, Pfu, Pho, Pwo, ES4, Bca, Bst, Sac, Sso, Poc, Pab, and Mth, or a mutant, variant, or derivative of any thereof. In some embodiments, the DNA polymerase is Taq polymerase. In some embodiments, the amplification reagents comprise at least one primer, deoxynucleotide triphosphates, a buffer, and a magnesium salt. In some embodiments, the magnesium salt is magnesium chloride. In some embodiments, the amplification reagents comprise forward and reverse primers for a target amplicon in the sample.

In some embodiments, the thermal cycling protocol comprises:

(1) a denaturation step comprising subjecting the mixture to a temperature of 90-96° C.;

(2) an annealing step comprising subjecting the mixture to a temperature of 45-68° C.; and (3) an extension step comprising subjecting the mixture to a temperature of 50-72° C.;

wherein the sequence of steps (1)-(3) is repeated 10 or more times in succession. In some embodiments, the sequence of steps (1)-(3) is repeated 20 or more times in succession.

In some embodiments, the thermal cycling protocol comprises:

(1a) a denaturation step comprising subjecting the mixture to a temperature of 90-96° C.;

(2a) an annealing/extension step comprising subjecting the mixture to a temperature of 45-70° C.; and wherein the sequence of steps (1a)-(2a) is repeated 10 or more times in succession. In some embodiments, the sequence of steps (1a)-(2a) is repeated 20 or more times in succession.

In some embodiments, step (c) comprises:

(i) lysing cells in the second mixture to form a lysed sample;

(ii) adding a DNA polymerase and amplification reagents to the lysed sample to form a mixture; and (iii) subjecting the mixture to an isothermal amplification protocol to amplify the nucleic acid from the sample.

In some embodiments, the detectable signal is a fluorescent signal.

In some embodiments, the microorganism is a bacterium. In some embodiments, the bacterium is from a genus selected from *Actinomyces, Bacteroides, Bacillus, Bordetella, Campylobacter, Clostridium, Corynebacterium, Enterobacter, Enterococcus, Escherichia, Fusobacterium, Haemophilus, Helicobacter, Klebsiella, Legionella, Leptospira, Listeria, Mycobacterium, Mycoplasma, Neisseria, Pasteurella, Pseudomonas, Salmonella, Staphylococcus, Streptobacillus, Streptococcus, Treponema, Vibrio*, and *Yersinia*. In some embodiments, the microorganism is a virus. In some embodiments, the virus is from a family selected from Retroviridae, Picornaviridae, Calciviridae, Flaviridae, Coronaviridae, Rhabdoviridae, Filoviridae, Paramyxoviridae, Orthomyxoviridae, Bungaviridae, Arenaviridae, Reoviridae, Birnaviridae, Hepadnaviridae, Parvoviridae, Papovaviridae, Adenoviridae, Herpesviridae, Poxyiridae, and Iridoviridae. In some embodiments, the microorganism or cell is a fungus, a yeast, mammalian cell, or plant cell.

In one aspect, provided herein is a method of amplifying a nucleic acid from a sample, the method comprising:

(a) contacting the sample with a compound disclosed herein (i.e., a compound having a NAB moiety, a LDCD moiety, and a NAM moiety, or a salt thereof) to form a first mixture;

(b) contacting the first mixture with an inactivating agent to form a second mixture; and (c) amplifying nucleic acids from the second mixture.

In some embodiments, the method does not include a photoactivation step. In some embodiments, the method does not include a culturing step.

In some embodiments, step (a) comprises contacting the sample with the compound or the salt thereof for 5 minutes to 180 minutes. In some embodiments, step (a) comprises contacting the sample with the compound or the salt thereof for 60 minutes to 120 minutes. In some embodiments, step (a) comprises adding to the sample a composition comprising the compound, or a salt thereof, in a solvent. In some embodiments, the solvent is dimethylsulfoxide. In some embodiments, in step (a), the first mixture comprises the compound at a concentration of 5-100 micromolar. In some embodiments, the inactivating agent comprises a nucleophile selected from an amine and a thiol. In some embodiments, the inactivating agent is selected from cysteine, glutathione, a dNTP, guanine, an amine-containing buffer, or a mixture of any thereof.

In some embodiments, step (c) comprises:

(i) lysing cells in the second mixture to form a lysed sample;

(ii) adding a DNA polymerase and amplification reagents to the lysed sample to form a mixture; and (iii) subjecting the mixture to a thermal cycling protocol to amplify the nucleic acid from the sample.

In some embodiments, the method further comprises a step of removing contaminants and/or cellular debris from the lysed sample, prior to adding the DNA polymerase and amplification reagents.

In some embodiments, the method further comprises heating the mixture to a temperature of at least 90° C. to activate the DNA polymerase prior to subjecting the mixture to the thermal cycling protocol.

In some embodiments, the DNA polymerase is a thermostable DNA polymerase selected from Taq, Tbr, Tfi, Tfl, KOD, Tru, Tth, Tli, Tac, Tne, Tma, Pfu, Pho, Pwo, ES4, Bca, Bst, Sac, Sso, Poc, Pab, and Mth, or a mutant, variant, or derivative of any thereof. In some embodiments, the DNA polymerase is Taq polymerase.

In some embodiments, the amplification reagents comprise at least one primer, deoxynucleotide triphosphates, a buffer, and a magnesium salt. In some embodiments, the magnesium salt is magnesium chloride. In some embodiments, the amplification reagents comprise forward and reverse primers for a target amplicon in the sample.

In some embodiments, the thermal cycling protocol comprises:

(1) a denaturation step comprising subjecting the mixture to a temperature of 90-96° C.;

(2) an annealing step comprising subjecting the mixture to a temperature of 45-68° C.; and (3) an extension step comprising subjecting the mixture to a temperature of 50-72° C.;

wherein the sequence of steps (1)-(3) is repeated 10 or more times in succession. In some embodiments, the sequence of steps (1)-(3) is repeated 20 or more times in succession.

In some embodiments, the thermal cycling protocol comprises:

(1a) a denaturation step comprising subjecting the mixture to a temperature of 90-96° C.;

(2a) an annealing/extension step comprising subjecting the mixture to a temperature of 45-70° C.; and wherein the sequence of steps (1a)-(2a) is repeated 10 or more times in succession. In some embodiments, the sequence of steps (1a)-(2a) is repeated 20 or more times in succession.

In some embodiments, step (c) comprises:

(i) lysing cells in the second mixture to form a lysed sample;

(ii) adding a DNA polymerase and amplification reagents to the lysed sample to form a mixture; and (iii) subjecting the mixture to an isothermal amplification protocol to amplify the nucleic acid from the sample.

In some embodiments, the sample is a sample suspected of comprising an organism or cell selected from a bacterium, a virus, a yeast, a fungi, a mammalian cell, or a plant cell. In some embodiments, the sample is suspected of comprising a bacterium. In some embodiments, the bacterium is from a genus selected from *Actinomyces, Bacteroides, Bacillus, Bordetella, Campylobacter, Clostridium, Corynebacterium, Enterobacter, Enterococcus, Escherichia, Fusobacterium, Haemophilus, Helicobacter, Klebsiella, Legionella, Leptospira, Listeria, Mycobacterium, Mycoplasma, Neisseria, Pasteurella, Pseudomonas, Salmonella, Staphylococcus, Streptobacillus, Streptococcus, Treponema, Vibrio*, and *Yersinia*. In some embodiments, the sample is suspected of comprising a virus. In some embodiments, the virus is from a family selected from Retroviridae, Picornaviridae, Calciviridae, Flaviridae, Coronaviridae, Rhabdoviridae, Filoviridae, Paramyxoviridae, Orthomyxoviridae, Bungaviridae, Arenaviridae, Reoviridae, Birnaviridae, Hepadnaviridae, Parvoviridae, Papovaviridae, Adenoviridae, Herpesviridae, Poxyiridae, and Iridoviridae.

In one aspect, provided herein is a method of removing nucleic acids from a sample, the method comprising: contacting the sample with a compound disclosed herein (i.e., a compound having a NAB moiety, a LDCD moiety, and a NAM moiety, or a salt thereof). In some embodiments, the compound is immobilized on a solid support.

In one aspect, provided herein is a system or kit comprising a compound disclosed herein (i.e., a compound having a NAB moiety, a LDCD moiety, and a NAM moiety, or a salt thereof).

In some embodiments, the system or kit further comprises a DNA polymerase. In some embodiments, the DNA polymerase is a thermostable DNA polymerase selected from Taq, Tbr, Tfi, Tfl, KOD, Tru, Tth, Tli, Tac, Tne, Tma, Pfu, Pho, Pwo, ES4, Bca, Bst, Sac, Sso, Poc, Pab, and Mth, or a mutant, variant, or derivative of any thereof. In some embodiments, the DNA polymerase is Taq polymerase. In some embodiments, the system or kit further comprises one or more amplification reagents. In some embodiments, the one or more amplification reagents are selected from at least one primer, deoxynucleotide triphosphates, a buffer, and a magnesium salt. In some embodiments, the system or kit further comprises forward and reverse primers for a target nucleic acid sequence of an organism or cell selected from a bacterium, a virus, a yeast, a fungi, a mammalian cell, or a plant cell. In some embodiments, the organism is a bacterium is from a genus selected from *Actinomyces, Bacteroides, Bacillus, Bordetella, Campylobacter, Clostridium, Corynebacterium, Enterobacter, Enterococcus, Escherichia, Fusobacterium, Haemophilus, Helicobacter, Klebsiella, Legionella, Leptospira, Listeria, Mycobacterium, Mycoplasma, Neisseria, Pasteurella, Pseudomonas, Staphylococcus, Streptobacillus, Streptococcus, Treponema, Vibrio*, and *Yersinia*. In some embodiments, the organism is a virus from a family selected from Retroviridae, Picornaviridae, Calciviridae, Flaviridae, Coronaviridae, Rhabdoviridae, Filoviridae, Paramyxoviridae, Orthomyxoviridae, Bungaviridae, Arenaviridae, Reoviridae, Birnaviridae, Hepadnaviridae, Parvoviridae, Papovaviridae, Adenoviridae, Herpesviridae, Poxyiridae, and Iridoviridae.

DETAILED DESCRIPTION

Figure 1:
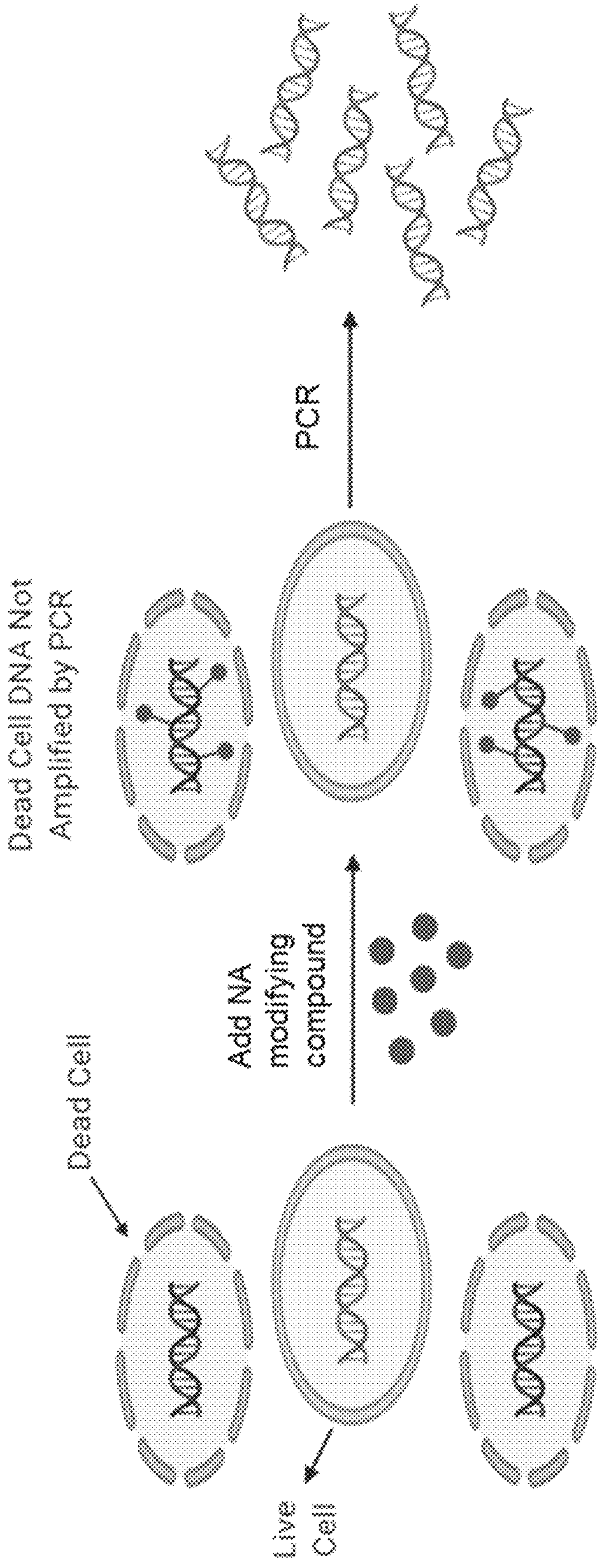
FIG. 1 shows a representative live-dead differentiation assay, which does not require a photoactivation step.

Provided herein are compounds, compositions, kits, and methods for conducting nucleic acid amplification reactions including viability PCR (vPCR) reactions. The compounds comprise a nucleic acid binding moiety, a nucleic acid modifying moiety, and a viability differentiation motif to differentiate DNA associated with viable cells from DNA associated with non-viable cells. The methods do not require a photoactivation step and allow for culture-independent detection of DNA from viable cells with minimal interference from the DNA of dead cells. The compounds, compositions, kits, and methods can simplify the vPCR process and improve the consistency and robustness of molecular-detection based viability testing. The compounds can also be used in other applications such as methods of removing nucleic acids from samples.

Section headings as used in this section and the entire disclosure herein are merely for organizational purposes and are not intended to be limiting.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents, and other references mentioned herein are incorporated by reference in their entirety. The materials, methods, and examples disclosed herein are illustrative only and not intended to be limiting.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Sorrell, Organic Chemistry, 2$^{nd}$ edition, University Science Books, Sausalito, 2006; Smith, March's Advanced Organic Chemistry: Reactions, Mechanism, and Structure, 7$^{th}$ Edition, John Wiley & Sons, Inc., New York, 2013; Larock, Comprehensive Organic Transformations, 3$^{rd}$ Edition, John Wiley & Sons, Inc., New York, 2018; and Carruthers, Some Modern Methods of Organic Synthesis, 3$^{rd}$ Edition, Cambridge University Press, Cambridge, 1987; the entire contents of each of which are incorporated herein by reference.

As used herein, the term "acyl" refers to a group —C(O)R, wherein R is hydrogen, alkyl, cycloalkyl, heterocyclyl, aryl, heteroalkyl, or heteroaryl. Examples of acyl include, but are not limited to, formyl, acetyl, cyclohexylcarbonyl, and benzoyl.

As used herein, the term "alkoxy" refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

As used herein, the term "alkyl" means a straight or branched saturated hydrocarbon chain containing from 1 to 30 carbon atoms, for example 1 to 16 carbon atoms ($C_1$-$C_{16}$ alkyl), 1 to 14 carbon atoms ($C_1$-$C_{14}$ alkyl), 1 to 12 carbon atoms ($C_1$-$C_{12}$ alkyl), 1 to 10 carbon atoms ($C_1$-$C_{10}$ alkyl), 1 to 8 carbon atoms ($C_1$-$C_8$ alkyl), 1 to 6 carbon atoms ($C_1$-$C_6$ alkyl), 1 to 4 carbon atoms ($C_1$-$C_4$ alkyl), 6 to 20 carbon atoms ($C_6$-$C_{20}$ alkyl), or 8 to 14 carbon atoms ($C_8$-$C_{14}$ alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecyl, and n-dodecyl.

As used herein, the term "alkylene" refers to a divalent group derived from a straight or branched chain hydrocarbon of 1 to 10 carbon atoms ($C_1$-$C_{10}$ alkylene), for example, of 1 to 6 carbon atoms ($C_1$-$C_6$ alkylene). Representative examples of alkylene include, but are not limited to, $—CH_2—$, $—CH_2CH_2—$, $—CH(CH_3)—$, $—CH_2CH_2CH_2—$, $—CH_2CH(CH_3)—$, $—CH_2CH_2CH_2CH_2—$, $—CH_2CH(CH_3)CH_2—$, $—CH_2CH_2CH(CH_3)—$, $—CH_2CH_2CH_2CH_2CH_2—$, $—CH_2CH(CH_3)CH_2CH_2—$, $—CH(CH_3)CH_2CH_2CH_2—$, $—CH_2CH_2CH_2CH_2CH_2CH_2—$, $—CH_2CH_2CH(CH_3)CH_2CH_2—$, $—CH_2CH(CH_3)CH_2CH_2CH_2—$, and $—CH(CH_3)CH_2CH_2CH_2CH_2—$.

As used herein, the term "alkenyl" refers to a straight or branched hydrocarbon chain containing from 2 to 30 carbon atoms and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

As used herein, the term "alkynyl" refers to a straight or branched hydrocarbon chain containing from 2 to 30 carbon atoms and containing at least one carbon-carbon triple bond. Representative examples of alkynyl include, but are not limited to, ethynyl, propynyl, and butynyl.

As used herein, the term "aryl" refers to an aromatic carbocyclic ring system having a single ring (monocyclic) or multiple rings (bicyclic or tricyclic) including fused ring systems, and zero heteroatoms. As used herein, aryl contains 6-20 carbon atoms ($C_6$-$C_{20}$ aryl), 6 to 14 ring carbon atoms ($C_6$-$C_{14}$ aryl), 6 to 12 ring carbon atoms ($C_6$-$C_{12}$ aryl), or 6 to 10 ring carbon atoms ($C_6$-$C_{10}$ aryl). Representative examples of aryl groups include, but are not limited to, phenyl, naphthyl, anthracenyl, and phenanthrenyl.

As used herein, the term "arylene" refers to a divalent aryl group. Representative examples of arylene groups include, but are not limited to, phenylene groups (e.g., 1,2-phenylene, 1,3-phenylene, and 1,4-phenylene).

As used herein, the term "cycloalkyl" refers to a saturated carbocyclic ring system containing three to ten carbon atoms and zero heteroatoms. The cycloalkyl may be monocyclic, bicyclic, bridged, fused, or spirocyclic. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, bicyclo[2.2.1]heptanyl, bicyclo[3.2.1]octanyl, and bicyclo[5.2.0]nonanyl.

As used herein, the term "cycloalkenyl" means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl, and cycloheptenyl.

As used herein, the term "halogen" or "halo" means F, Cl, Br, or I.

As used herein, the term "haloalkyl" means an alkyl group, as defined herein, in which at least one hydrogen atom (e.g., one, two, three, four, five, six, seven or eight hydrogen atoms) is replaced by a halogen.

As used herein, the term "heteroalkyl" means an alkyl group, as defined herein, in which one or more of the carbon atoms (and any associated hydrogen atoms) are each independently replaced with a heteroatom group such as —NR—, —O—, —S—, —S(O)—, $—S(O)_2—$, and the like, where R is H, alkyl, aryl, cycloalkyl, heteroalkyl, heteroaryl or heterocyclyl, each of which may be optionally substituted. By way of example, 1, 2 or 3 carbon atoms may be independently replaced with the same or different heteroatomic group. Examples of heteroalkyl groups include, but are not limited to, $—OCH_3$, $—CH_2OCH_3$, $—SCH_3$, $—CH_2SCH_3$, $—NRCH_3$, and $—CH_2NRCH_3$, where R is hydrogen, alkyl, aryl, arylalkyl, heteroalkyl, or heteroaryl, each of which may be optionally substituted. Heteroalkyl also includes groups in which a carbon atom of the alkyl is oxidized (i.e., is —C(O)—).

As used herein, the term "heteroalkylene" means an alkylene group, as defined herein, in which one or more of the carbon atoms (and any associated hydrogen atoms) are each independently replaced with a heteroatom group such as —NR—, —O—, —S—, —S(O)—, $—S(O)_2—$, and the like, where R is H, alkyl, aryl, cycloalkyl, heteroalkyl, heteroaryl or heterocyclyl, each of which may be optionally substituted. By way of example, 1, 2 or 3 carbon atoms may be independently replaced with the same or different heteroatomic group. Heteroalkylene also includes groups in which a carbon atom of the alkyl is oxidized (i.e., is —C(O)—). Examples of heteroalkylene groups include, but are not limited to, $—CH_2—O—CH_2—$, $—CH_2—S—CH_2—$, $—CH_2—NR—CH_2—$, $—CH_2—NH—C(O)—CH_2$, and the like, as well as polyethylene oxide chains, polypropylene oxide chains, and polyethyleneimine chains.

As used herein, the term "heteroaryl" refers to an aromatic group having a single ring (monocyclic) or multiple rings (bicyclic or tricyclic), having one or more ring heteroatoms independently selected from O, N, and S. The aromatic monocyclic rings are five- or six-membered rings containing at least one heteroatom independently selected from O, N, and S (e.g., 1, 2, 3, or 4 heteroatoms independently selected from O, N, and S). The five-membered aromatic monocyclic rings have two double bonds, and the six-membered aromatic monocyclic rings have three double bonds. The bicyclic heteroaryl groups are exemplified by a monocyclic heteroaryl ring appended fused to a monocyclic aryl group, as defined herein, or a monocyclic heteroaryl group, as defined herein. The tricyclic heteroaryl groups are exemplified by a monocyclic heteroaryl ring fused to two rings independently selected from a monocyclic aryl group, as defined herein, and a monocyclic heteroaryl group as defined herein. Representative examples of monocyclic heteroaryl include, but are not limited to, pyridinyl (including pyridin-2-yl, pyridin-3-yl, pyridin-4-yl), pyrimidinyl, pyrazinyl, pyridazinyl, pyrrolyl, benzopyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, furanyl, oxazolyl, isoxazolyl, 1,2,4-triazinyl, and 1,3,5-triazinyl. Representative examples of bicyclic heteroaryl include, but are not limited to, benzimidazolyl, benzodioxolyl, benzofuranyl, benzooxadiazolyl, benzopyrazolyl, benzothiazolyl, benzothienyl, benzotriazolyl, benzoxadiazolyl, benzoxazolyl, chromenyl, imidazopyridine, imidazothiazolyl, indazolyl, indolyl, isobenzofuranyl, isoindolyl, isoquinolinyl, naphthyridinyl, purinyl, pyridoimidazolyl, quinazolinyl, quinolinyl, quinoxalinyl, thiazolopyridinyl, thiazolopyrimidinyl, thienopyrrolyl, and thienothienyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings.

As used herein, the term "heterocycle" or "heterocyclic" refers to a saturated or partially unsaturated non-aromatic cyclic group having one or more ring heteroatoms independently selected from O, N, and S. means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from O, N, and S. The three- or four-membered ring contains zero or one double bond, and one heteroatom selected from O, N, and S. The five-membered ring contains zero or one double bond and one, two or three heteroatoms selected from O, N, and S. The six-membered ring contains zero, one, or two double bonds and one, two, or three heteroatoms selected from O, N, and S. The seven- and eight-membered rings contains zero, one, two, or three double bonds and one, two, or three heteroatoms selected from O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan,hexahydro-1H-1,4-methanocyclopenta[c]furan, aza-adamantane (1-azatricyclo[3.3.1.1$^{3-7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings.

As used herein, the term "hydroxy" means an —OH group.

In some instances, the number of carbon atoms in a group (e.g., alkyl, alkoxy, or cycloalkyl) is indicated by the prefix "Cr-Cy-", wherein x is the minimum and y is the maximum number of carbon atoms in the group. Thus, for example, "$C_1$-$C_3$-alkyl" refers to an alkyl group containing from 1 to 3 carbon atoms.

As used herein, the term "substituent" refers to a group substituted on an atom of the indicated group.

When a group or moiety can be substituted, the term "substituted" indicates that one or more (e.g., 1, 2, 3, 4, 5, or 6; in some embodiments 1, 2, or 3; and in other embodiments 1 or 2) hydrogens on the group indicated in the expression using "substituted" can be replaced with a selection of recited indicated groups or with a suitable group known to those of skill in the art (e.g., one or more of the groups recited below), provided that the designated atom's normal valence is not exceeded. Substituent groups include, but are not limited to, alkyl, alkenyl, alkynyl, alkoxy, acyl, amino, amido, amidino, aryl, azido, carbamoyl, carboxyl, carboxyl ester, cyano, cycloalkyl, cycloalkenyl, guanidino, halo, haloalkyl, haloalkoxy, heteroalkyl, heteroaryl, heterocyclyl, hydroxy, hydrazino, imino, oxo, nitro, phosphate, phosphonate, sulfonic acid, thiol, thione, or combinations thereof.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —$CH_2O$— optionally also recites —$OCH_2$—, and —OC(O)NH— also optionally recites —NHC(O)O—.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, a "nucleic acid binding moiety" or "NAB moiety" is a moiety that interacts with nucleic acid in a non-covalent manner. Non-limiting examples of NAB moieties include major groove and minor groove binders (which interact with DNA by binding to the major or minor groove of the DNA double helix), intercalators (planar moieties that inserts between nucleotide base pairs), and mixed-mode NAB moieties (including a portion which intercalates into the DNA double helix and a portion that protrudes into a groove, such as the minor groove).

As used herein, a "nucleic acid modifying moiety" or "NAM moiety" is a moiety that reacts with at least one nucleotide of a nucleic acid, forming a covalent linkage to the nucleic acid (e.g., a covalent bond or a coordinate covalent bond). The NAM moiety can form a covalent linkage with one DNA nucleobase, or can react with two different DNA nucleobases to form a crosslink, either within the same strand (intrastrand) or between opposite strands (intrastrand).

As used herein, the term "cell permeable" refers to a compound or moiety that is capable of effectively crossing a cell membrane of a non-viable cell or a cell membrane of a viable cell that has been synthetically permeabilized or the intact membrane of a cell whether viable or non-viable. As used herein, the term "cell impermeable" refers to a compound or moiety that is incapable of effectively crossing a cell membrane of a viable cell that has not been synthetically permeabilized.

As used herein, the term "sample" is used in its broadest sense. In one sense, it is meant to include a specimen or culture obtained from any source as well as biological, food, and environmental samples. Biological samples may be obtained from animals (including humans) and encompass fluids, solids, tissues, and gases. Biological samples include blood products such as plasma, serum, and the like. Sample may also refer to cell lysates, which may include cells that have been lysed with a lysing agent or lysates such as rabbit reticulocyte or wheat germ lysates. Sample may also include cell-free expression systems. Environmental samples include environmental material such as surface matter, soil, water, crystals, and industrial samples. Such examples are not to be construed as limiting the sample types applicable to the present disclosure.

As used herein, the term "substantially" means that the recited characteristic, parameter, and/or value need not be achieved exactly, but that deviations or variations, including for example, tolerances, measurement error, measurement accuracy limitations, and other factors known to skill in the art, may occur in amounts that do not preclude the effect the characteristic was intended to provide. A characteristic or feature that is substantially absent may be one that is within the noise, beneath background, below the detection capabilities of the assay being used, or a small fraction (e.g., <1%, <0.1%, <0.01%, <0.001%, <0.00001%, <0.000001%, <0.0000001%) of the significant characteristic.

"Variant" is used herein to describe a peptide or polypeptide that differs in amino acid sequence by the insertion, deletion, or conservative substitution of amino acids, but retain at least one biological activity. Representative examples of "biological activity" include enzymatic activity, such as DNA polymerase activity. Variant is also used herein to describe a protein with an amino acid sequence that is substantially identical to a referenced protein with an amino acid sequence that retains at least one biological activity. As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. COMPOUNDS

The present disclosure includes compounds that can selectively bind to and modify nucleic acids from non-viable cells without requiring a photoactivation step. Such compounds can be used in methods of selectively detecting nucleic acids from viable cells, and in methods of removing nucleic acids from samples.

In one aspect, the disclosure provides a compound or a salt thereof, the compound comprising:

(A) a nucleic acid binding moiety ("NAB moiety");
(B) a live/dead cell differentiating moiety ("LDCD moiety"); and
(C) a nucleic acid modifying moiety ("NAM moiety").

In some embodiments, the compound comprises more than one NAB moiety (e.g., two NAB moieties), more than one LDCD moiety (e.g., two LDCD moieties), and/or more than one NAM moiety (e.g., two NAM moieties). In some embodiments, the compound comprises more than one NAB moiety (e.g., two NAB moieties). In some embodiments, the compound comprises more than one NAM moiety (e.g., two NAM moieties).

In some embodiments, the compound has a structure selected from:

A-B—C, B-A-C, A-C—B, B—C-A, and B—C,

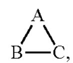, wherein A is the NAB moiety, B is the LDCD moiety, C is the NAM moiety. In some embodiments, the compound has the structure A-B—C, wherein A is the NAB moiety, B is the LDCD moiety, C is the NAM moiety. In such embodiments, the NAB moiety A is linked to the LDCD moiety B via a covalent bond, and the NAM moiety C is linked to the LDCD moiety B by another covalent bond.

The compounds include at least one NAB moiety, which is a moiety that interacts with nucleic acids in a non-covalent manner. The NAB moiety efficiently binds to nucleic acid species, facilitating rapid covalent modification of the nucleic acid by the NAM moiety. In some embodiments, the NAB moiety interacts with DNA by binding to the major groove of the DNA double helix. In some embodiments, the NAB moiety interacts with DNA by binding to the minor groove of the DNA double helix. In some embodiments, the NAB moiety is an intercalating moiety that inserts between nucleotide base pairs, such as an intercalating dye.

Suitable NAB moieties comprise groups such as acridine, phenanthridine (e.g., phenylphenanthridium), dipyridine, terpyridine, phenanthroline, indole, quinoline, cyanine, quinacrine, benzothiazole, benzimidazole (e.g., bibenzimidazole), pyridocarbazole (e.g., a pyridocarbazole dimer), an aminoglycoside, and the like. Furthermore, a wide variety of nucleic acid stains are known, any of which (or portions thereof) can be used as the NAB moiety in the compounds described herein. Examples of nucleic acid stains include, for example, ethidium bromide, Hoescht stain, DAPI, and SYBR Green. Additional nucleic acid stains are described in the Molecular Probes Handbook, a Guide to Fluorescent Probes and Labeling Technologies, 11$^{th}$ Edition (2010), Chapter 8, which is incorporated herein by reference in its entirety. Other nucleic acid binding dyes are disclosed in U.S. Pat. No. 9,206,474, which is incorporated herein by reference in its entirety. Other compounds known to have nucleic acid binding activity include metallo-intercalators, such as ruthenium and rhodium complexes with ligands such as bipyridine, phenanthroline, 4,4,-diphenylbipyridine, and derivatives thereof.

Representative examples of NAB moieties that can be used in the compounds described herein include the following.

Single-stranded DNA/RNA binding moieties, such as:

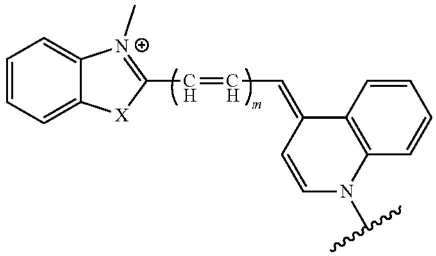

and

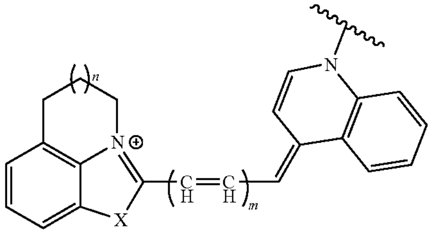

, wherein X is O, NH, or S, m is 0, 1, or 2, and n is 0, 1, 2, or 3 (e.g., wherein m is 1 and n is 1);

Intercalating moieties, such as:

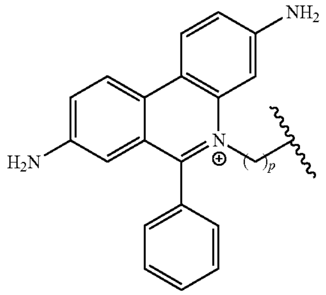

wherein p is 0 or 1,

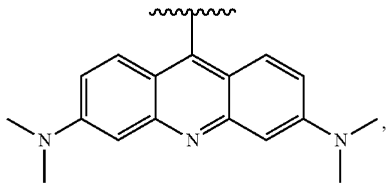

, and

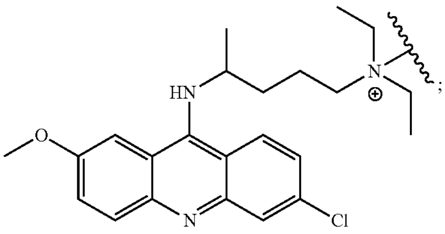

;

Minor groove binders, such as:

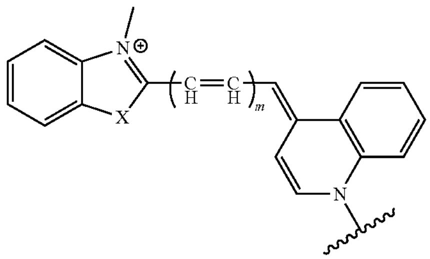

and

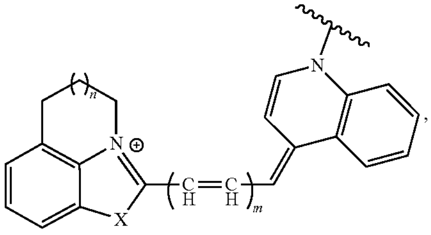

, wherein X is O, NH, or S, m is 0, 1, or 2, and n is 0, 1, 2, or 3 (e.g., wherein m is 1 and n is 1);

Major groove binders, such as:

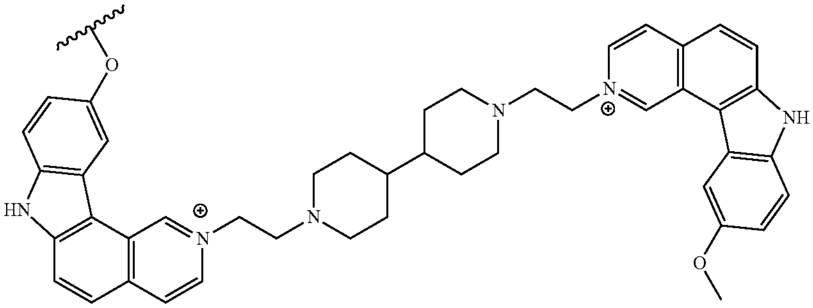

and

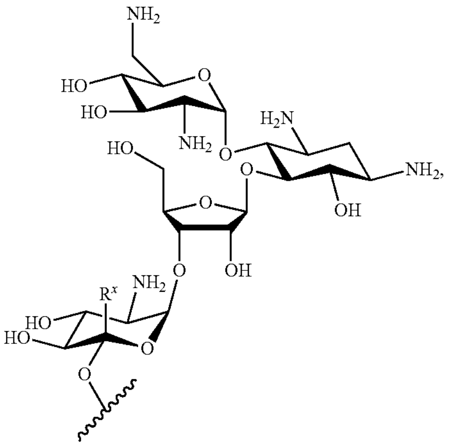

wherein $R^x$ is $-CH_2NH_2$ or H.

In particular embodiments, the NAB moiety is selected from:

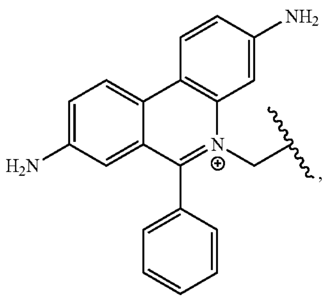

,

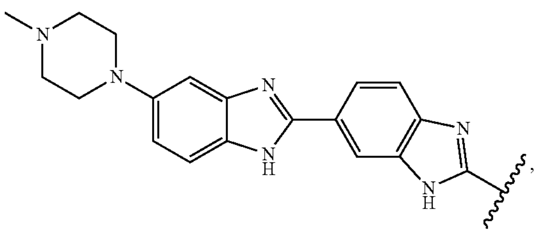

, and

-continued

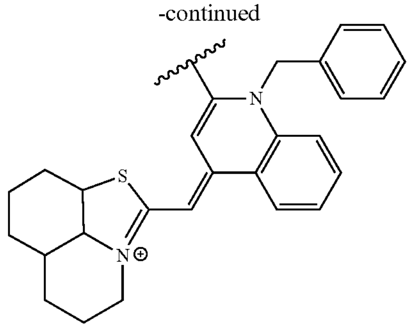

The compounds include an LDCD moiety, which comprises at least one LDCD motif that renders the compounds capable of binding to and modifying the DNA from dead cells, but not viable cells. The LDCD motif either prevents entry of the molecule into live cells or is processed by live cells such that the compound is unable to modify viable cell DNA. The LDCD motif distinguishes the compounds described herein from other compounds that include a NAB moiety and a NAM moiety (e.g., anticancer drugs or research agents, in which the compounds are designed to be cell permeable in order to bind to and modify nucleic acids in live cells). In addition to the at least one LDCD motif, the LDCD moiety can also include other atoms or groups of atoms, including but not limited to alkylene groups ($—(CH_2)_n—$), ether groups (—O—), thioether groups (—S—), amide linkages (—C(O)NH—), ester linkages (—C(O)O—), carbamate linkages (—OC(O)NH—), sulfonamide linkages ($—S(O)_2NH—$), phenylene linkages ($—C_6H_4—$), and any combination thereof. Furthermore, any substitutable atom or group can be substituted with an appropriate substituent (e.g., an amide linkage could include a group —C(O)NR—, where R is a suitable substituent, or a phenylene linkage can include one or more substituents on the phenyl group).

In some embodiments, the LDCD moiety serves as a linker between one or more NAB moieties and one or more NAM moieties.

In some embodiments, the LDCD moiety comprises at least one LDCD motif selected from charged moieties, high molecular weight moieties, immobilization moieties, and metabolically cleavable moieties.

In some embodiments, the LDCD motif is a charged moiety, which will preclude the molecule from entering live cells. In some embodiments, the LDCD moiety includes at least one charged moiety selected from a carboxylate group, a sulfate group, a sulfonate group, a phosphate group, a phosphonate group, and an ammonium group (e.g., a quaternary ammonium group). In some embodiments, the LDCD moiety includes more than one charged moiety. For example, in some embodiments, the LDCD moiety includes more than one carboxylate group, more than one sulfate group, more than one sulfonate group, more than one phosphate group, more than one phosphonate group, or more than one ammonium group (e.g., more than one quaternary ammonium group). In some embodiments, the LDCD moiety includes 2, 3, 4, 5, 6, or more charged moieties. In some embodiments, the LDCD moiety includes at least one quaternary ammonium center. In some embodiments, the LDCD moiety includes at least one group of formula $—N^+(CH_3)_2—$. In some embodiments, the LDCD moiety includes at least one carboxylate group. In some embodiments, the LDCD moiety includes at least one group of formula $—CH_2COO^-$ or $—CH_2CH_2COO^-$. In some embodiments, the LDCD moiety includes at least one phosphonate group. In some embodiments, the LDCD moiety includes at least one group of formula $—CH_2PO_3^{2}—$ or $CH_2CH_2PO_3^{2-}$.

In some embodiments, the LDCD motif is a high molecular weight moiety, for example, a moiety that has a molecular weight such that the overall compound has a molecular weight of greater than 600 g/mol, e.g., greater than 700 g/mol, greater than 800 g/mol, greater than 900 g/mol, or greater than 1000 g/mol. Compounds of higher molecular weights can slow down mobility and impact cell permeability. The high molecular weight moiety can include any combination of groups such as alkylene, heteroalkylene, arylene, and heteroarylene moieties, provided that the total molecular weight of the LDCD moiety is sufficient to render the compound unable to enter a live cell (e.g., such that the overall compound has a molecular weight of 600 g/mol or higher). In some embodiments, the high molecular weight moiety includes a polyethylene glycol chain (i.e., a group of formula $—(CH_2CH_2O)_n—$, wherein n is an integer from 1-100, e.g., 1, 2, 3, 4, 5, 6, 7, 8, 9, 10, 15, 20, 25, 30, 35, 40, 45, 50, 55, 60, 65, 70, 75, 80, 85, 90, 95, or 100). In some embodiments, the LDCD moiety is a peptide, such as a peptide with properties that render the molecule cell-impermeable and do not interfere with DNA binding.

In some embodiments, the LDCD motif is a metabolically cleavable moiety. Molecules having such moieties may be able to enter both viable and non-viable cells, but the viable cells would process the moiety to release the NAM moiety and thus prevent covalent modification. Non-viable cells are not able to process the moiety, therefore the NAM moiety can effectively interact with the nucleic acid to prevent its amplification. For example, a trimethyl quinone lock is a metabolically cleavable moiety that, when incorporated into compounds at an appropriate position, can be processed inside a viable cell to release the NAB moiety or the NAM moiety, rendering the compound unable to target and modify the DNA. For example, in some embodiments, in a viable cell, the trimethylquinone moiety is reduced by an intracellular reductase enzyme. The resulting trimethylhydroquinone moiety undergoes a lactonization reaction to produce a dihydrocoumarin. Further rearrangement of the rest of the molecule then leads to release of the NAM moiety and/or the NAB moiety. See, for example, WO 2015/116867, and Mustafa et al. Bioconjugate Chem. 2016, 27, 1, 87-101, each of which is incorporated herein by reference in its entirety. An exemplary reaction is shown below in Scheme 1.

Scheme 1. Metabolic cleavage of a compound containing a trimethyl quinone lock LDCD motif

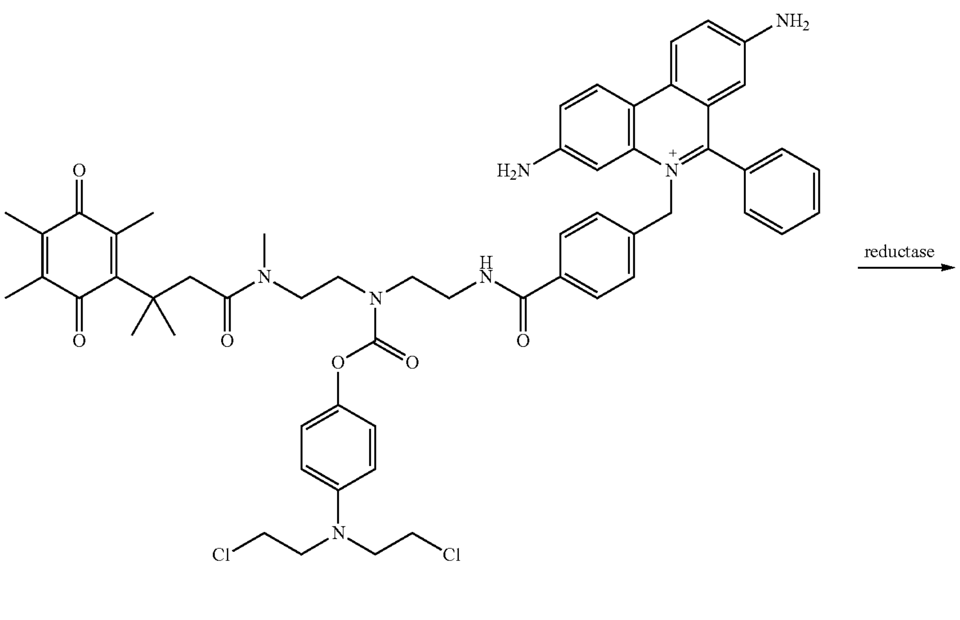

-continued

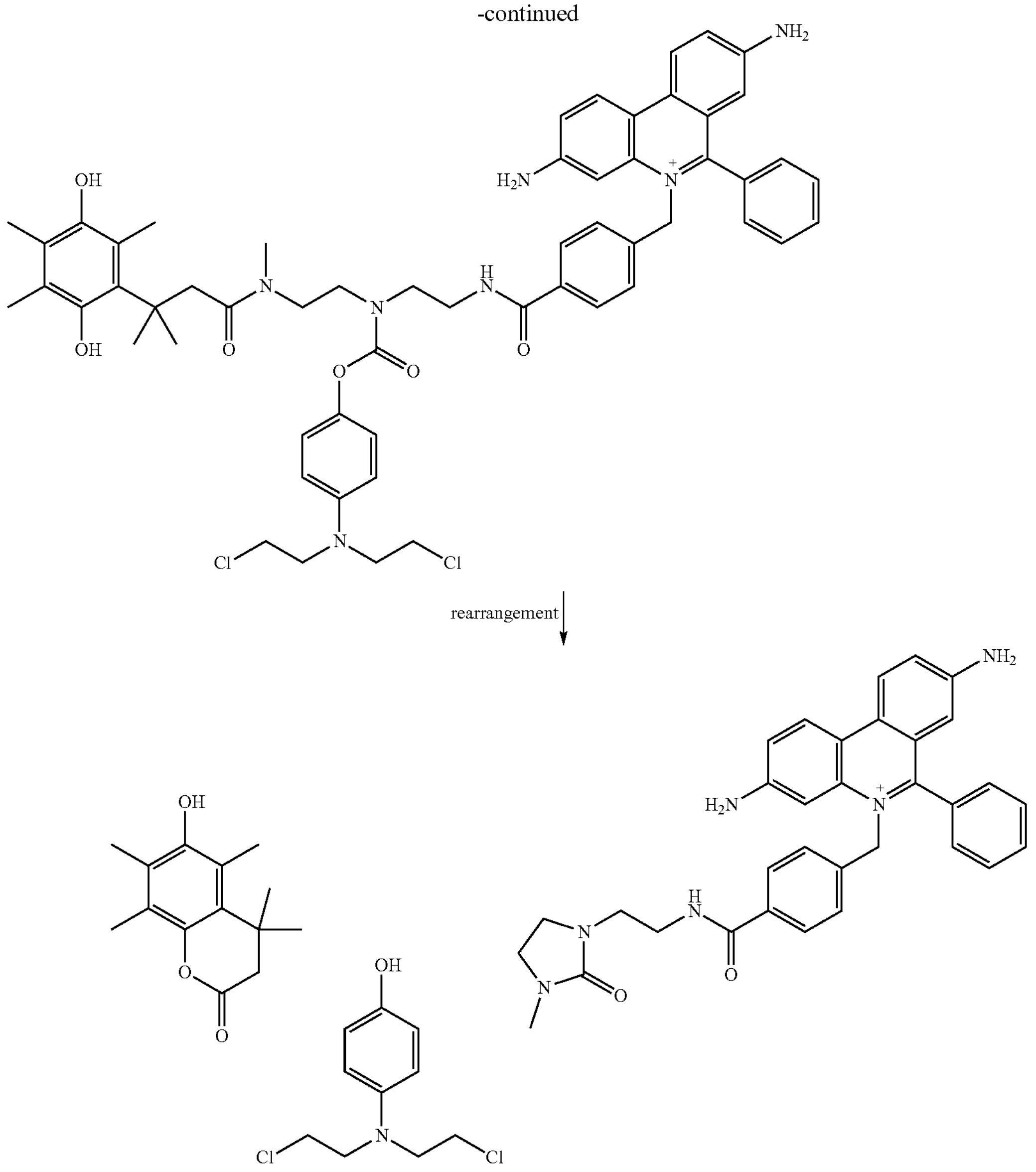

In some embodiments, the LDCD motif comprises a solid support. Binding of the compound to a solid support allows a sample containing viable and non-viable cells to be mixed with the solid support such that DNA from non-viable cells will bind to the solid support, whereas viable cells will not. Separation of the solid support from the rest of the sample will provide a sample containing only viable cells, which can be used in a subsequent amplification reaction. This embodiment also allows for removal of free DNA from other types of samples, which can be used in applications requiring generation of DNA-free reagents and/or solutions. The solid support could be, for example, a bead, a resin, a magnetic particle, a membrane, a gel, an ionic liquid (see, e.g., Egorova et al. *Chem. Rev.* 2017, 117, 10, 7132-7189), or a surface such as the surface of a tube, vial, slide, microtiter plate, cuvette, or the like. Methods of immobilizing compounds on solid supports are known to those skilled in the art.

The compounds also include at least one NAM moiety, which serves to covalently modify the nucleic acid and thus prevent it from being amplified. Examples of NAM moieties include DNA alkylating agents, such as nitrogen mustards (e.g., bendamustine, chlorambucil, chlormethine, cyclophosphamide, ifosfamide, melphalan, and uramustine), nitrosoureas (e.g., carmustine, chlorozotocin, ethylnitrosourea, fotemustine, lomustine, nimustine, ranimustine, semustine, and streptozocin), and alkyl sulfonates (e.g., busulfan), seco-CBI compounds (e.g., 1-(chloromethyl)-5-hydroxy-1,2-dihydro-3H-benz(e)indole), and pyrrolo[2,1-c][1,4]benzodiazepine (PBD) compounds (e.g., 8-hydroxy-7-methoxy-2-methylene-1,2,3,11a-tetrahydro-5H-benzo[e]pyrrolo[1,2-a][1,4]diazepin-5-one). Any of these, or derivatives thereof, can be used as a basis for a NAM moiety in the compounds described herein.

Other NAM moieties include platinum-based moieties, which modify DNA through binding of DNA nucleobases (typically via the N7 position of guanine residues) to the platinum center (via a coordinate covalent bond). Examples of platinum-based chemotherapeutic agents include cisplatin, carboplatin, nedaplatin, ormaplatin, oxaliplatin, phenanthriplatin, picoplatin, and satraplatin, any of which (or derivatives thereof) can be used as a basis for a NAM moiety in the compounds described herein. For example, the compound may feature a monodentate or bidentate ligand that binds to the platinum center (e.g., a moiety with one or more primary amines and/or secondary amines, and/or another source of a coordinating nitrogen atom, such as a pyridine, quinoline, or phenanthridine moiety).

In some embodiments, the NAM moiety comprises a group selected from:

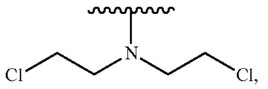

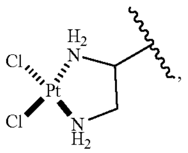

-continued

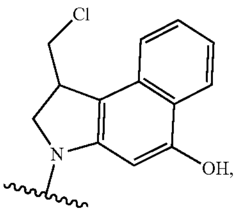

and

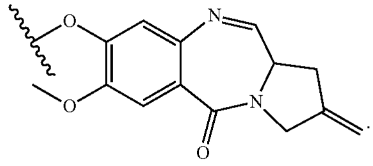

In some embodiments, the compound is selected from:

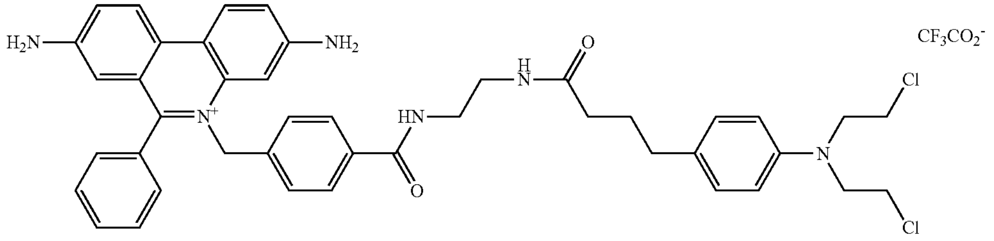

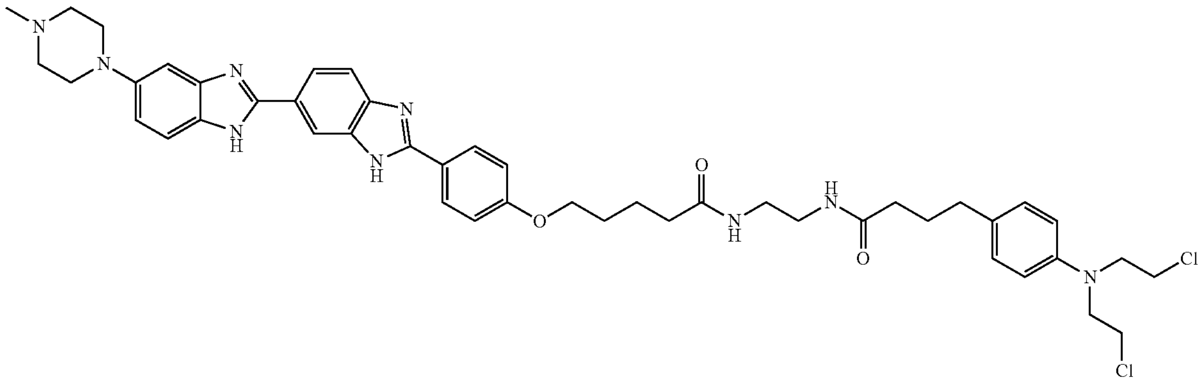

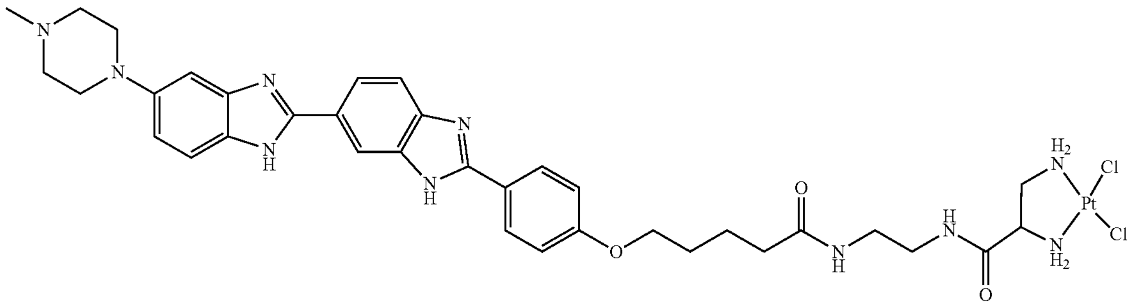

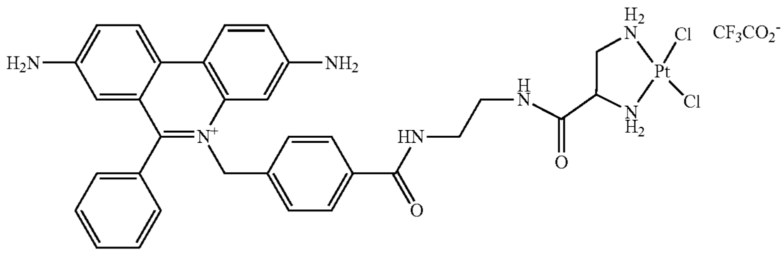

-continued
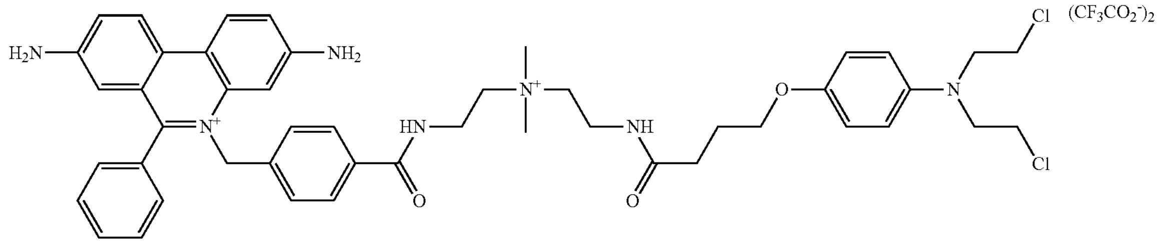
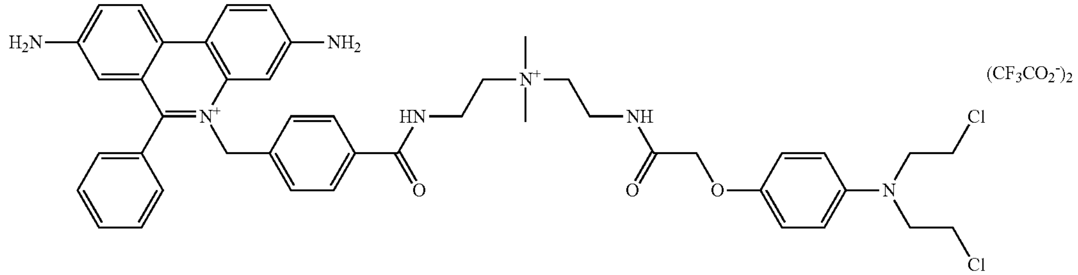
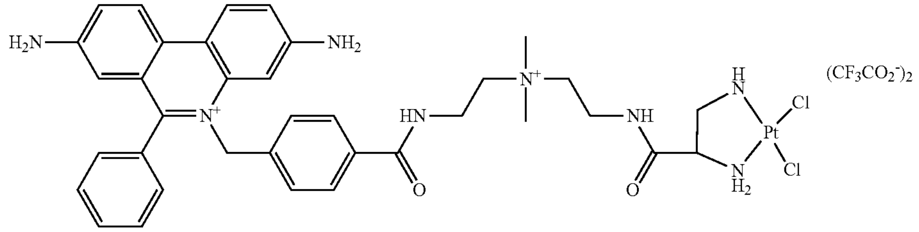
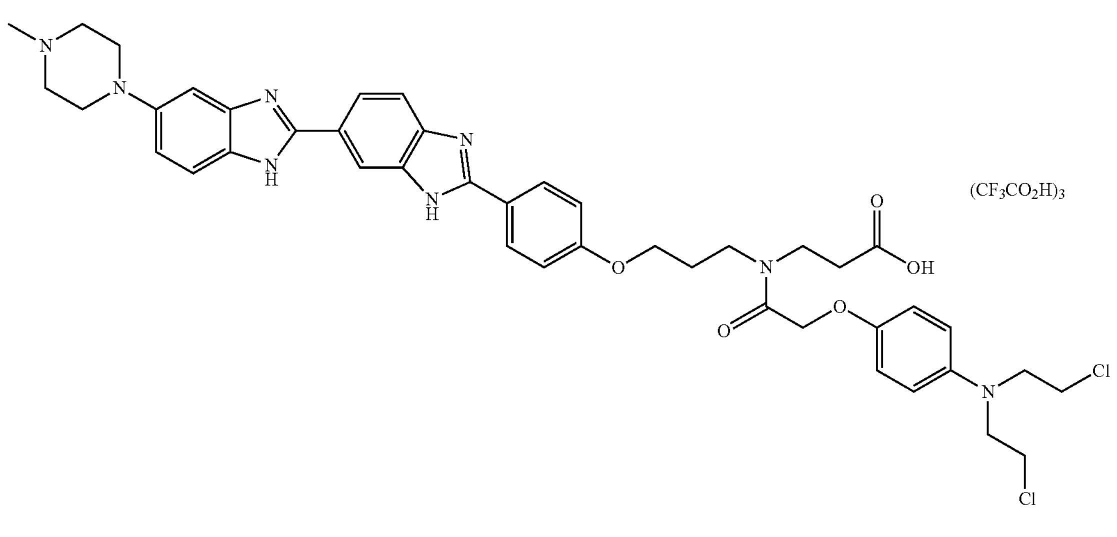

-continued
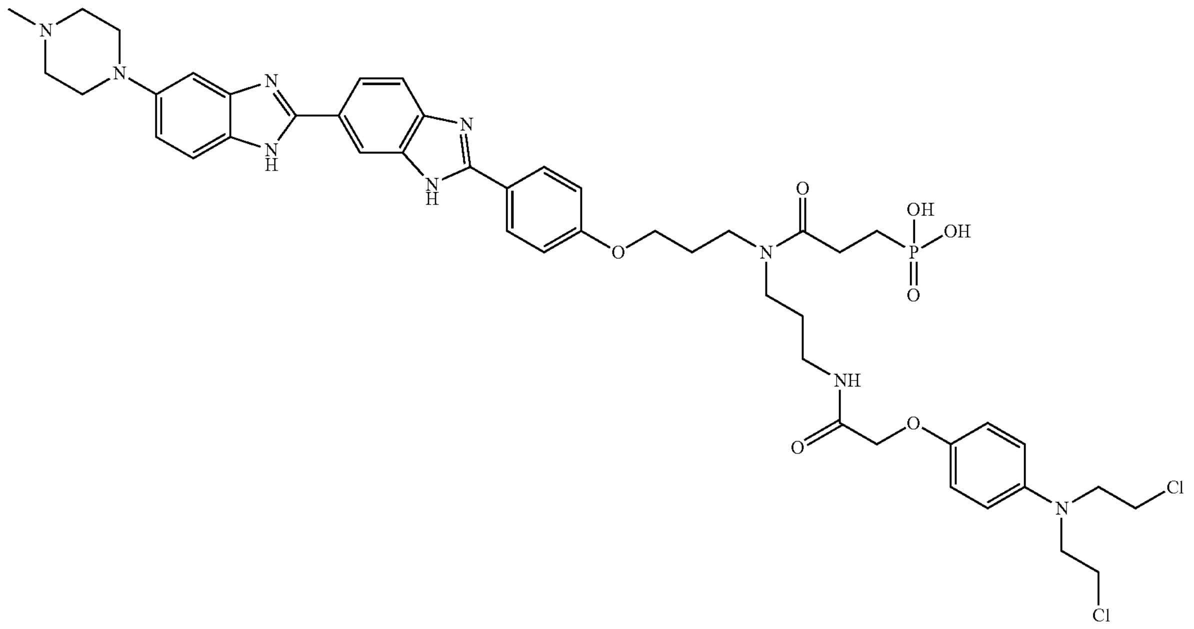
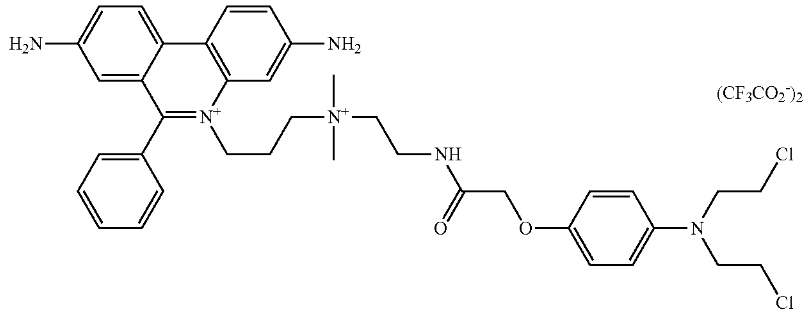
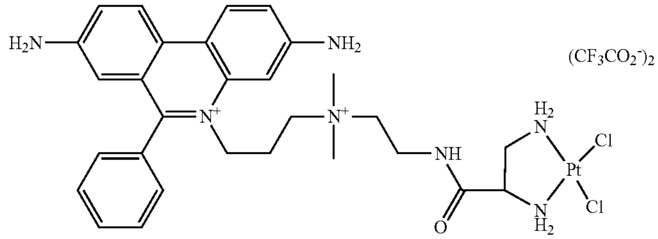
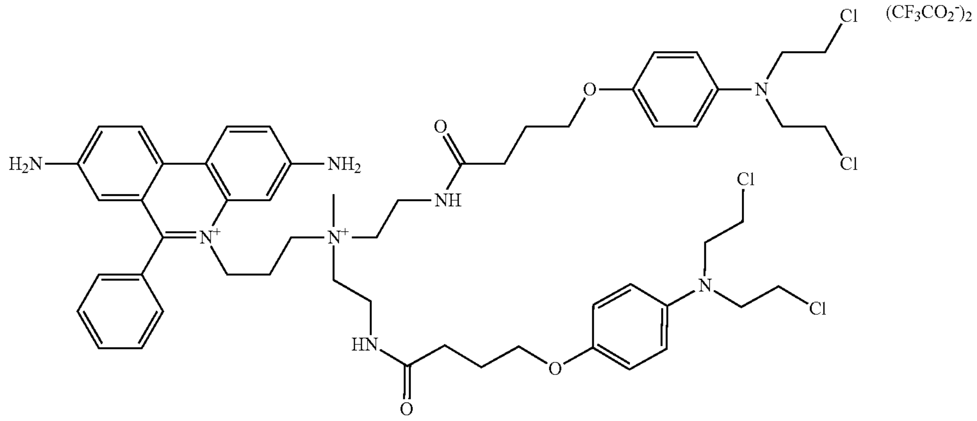
and

-continued

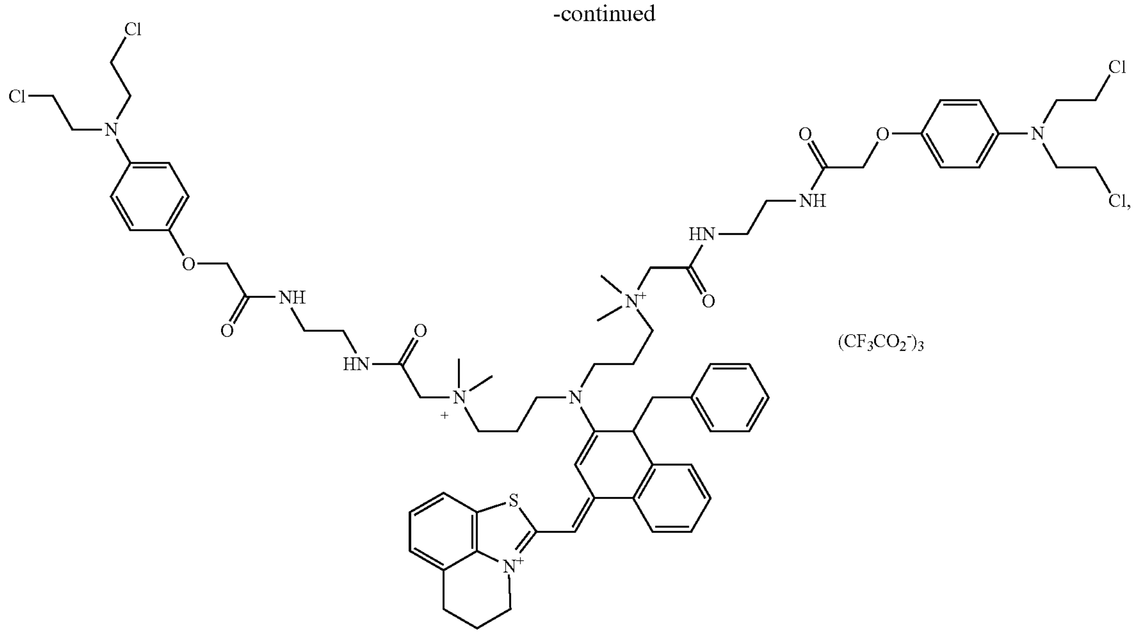

$(CF_3CO_2^-)_3$ or a salt of any thereof.

The compound can be in the form of a salt. In some embodiments, a neutral form of the compound may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure.

In particular, if the compound is anionic or has a functional group that may be anionic (e.g., —COOH may be —COO, —$SO_3H$ may be —$SO_3$, or —$P(O)(OH)_2$ can be —$PO_3^{2-}$), then a salt may be formed with one or more suitable cations. Examples of suitable inorganic cations include, but are not limited to, alkali metal cations such as $Li^+$, $Na^+$, and $K^+$, alkaline earth cations such as $Ca^{2+}$ and $Mg^{2+}$, and other cations. Sodium salts may be particularly suitable. Examples of suitable organic cations include, but are not limited to, ammonium ion (i.e., $NH_4^+$) and substituted ammonium ions (e.g., $NH_3R_1^+$, $NH_2R_2^+$, $NHR_3^+$, and $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine as well as amino acids such as lysine and arginine. In some embodiments, the compound is a sodium salt.

If the compound is cationic or has a functional group that may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, tetrafluoroboric, toluenesulfonic, trifluoromethanesulfonic, and valeric. In some embodiments, the compound is a halide salt, such as a chloro, bromo, or iodo salt. In some embodiments, the compound is a tetrafluoroborate or trifluoromethanesulfonate salt.

The compounds can be prepared by a variety of methods, including those shown in the Examples. The compounds and intermediates herein may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration as described for instance in "Vogel's Textbook of Practical Organic Chemistry," 5th edition (1989), by Furniss, Hannaford, Smith, and Tatchell, pub. Longman Scientific & Technical, Essex CM20 2JE, England.

Reaction conditions and reaction times for each individual step can vary depending on the particular reactants employed and substituents present in the reactants used. Specific procedures are provided in the Examples section. Reactions can be worked up in the conventional manner, e.g., by eliminating the solvent from the residue and further purified according to methodologies generally known in the art such as, but not limited to, crystallization, distillation, extraction, trituration, and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups, and the methods for protecting and deprotecting different substituents using such suitable protecting groups, are well known to those skilled in the art; examples of which can be found in the treatise by PGM Wuts entitled "Greene's Protective Groups in Organic Synthesis" (5th ed.), John Wiley & Sons, Inc. (2014), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step) or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material or by resolution of a mixture of the geometric isomers of the compound or intermediates using a standard procedure such as chromatographic separation.

The synthetic schemes and specific examples as described are illustrative and are not to be read as limiting the scope of the invention as it is defined in the claims. All alternatives, modifications, and equivalents of the synthetic methods and specific examples are included within the scope of the claims.

3. COMPOSITIONS AND SYSTEMS/KITS

In some embodiments, the present disclosure provides compositions and systems/kits comprising a nucleic acid modifying compound described herein (i.e., a compound comprising a NAB moiety, a LDCD moiety, and a NAM moiety).

The composition comprising the nucleic acid modifying compound described herein can further comprise a solvent. In some embodiments, the solvent is water. In such embodiments, the composition may further include one or more water-soluble components such as a salt or a buffer. In some embodiments, the solvent is an organic solvent such as dimethylsulfoxide (DMSO). Use of DMSO as a solvent for the compounds may provide additional advantages when amplifying DNA from samples comprising Gram-negative bacteria, because such bacteria have an additional lipopolysaccharide layer that may be more difficult for the compounds to cross, even when the cells are non-viable. Use of DMSO as a solvent can increase the DNA modification efficiency in samples containing Gram-negative bacteria.

The present disclosure further provides a system or kit comprising a compound described herein (i.e., a compound comprising a NAB moiety, a LDCD moiety, and a NAM moiety). The system or kit includes the compound, either alone or in a solvent such as water or DMSO. When the compound is provided alone, the system or kit may further include the solvent in which the compound can be dissolved. The system or kit may further comprise one or more reagents used to carry out an amplification reaction, such as a viability PCR reaction.

For example, in some embodiments, the system or kit further comprises a DNA polymerase. DNA polymerases that can be used in accordance with these embodiments include, but are not limited to, any polymerase capable of replicating a DNA molecule. In some embodiments, the DNA polymerase is a thermostable polymerase, which is especially useful in PCR applications. Thermostable polymerases are isolated from a wide variety of thermophilic bacteria, such as *Thermus aquaticus* (Taq), *Thermus brockianus* (Tbr), *Thermus filiformis* (Tfi), *Thermus flavus* (Tfl), *Thermococcus kodakaraensis* (KOD), *Thermus ruber* (Tru), *Thermus thermophilus* (Tth), *Thermococcus litoralis* (Tli) and other species of the *Thermococcus* genus, *Thermoplasma acidophilum* (Tac), *Thermotoga neapolitana* (Tne), *Thermotoga maritima* (Tma), and other species of the *Thermotoga* genus, *Pyrococcus furiosus* (Pfu), *Pyrococcus horikossii* (Pho), *Pyrococcus* woesei (Pwo), *Pyrococcus* strain ES4 (ES4), and other species of the *Pyrococcus* genus, *Bacillus caldophilus* (Bca), *Bacillus sterothermophilus* (Bst), *Sulfolobus acidocaldarius* (Sac), *Sulfolobus solfataricus* (Sso), *Pyrodictium occultum* (Poc), *Pyrodictium abyssi* (Pab), and *Methanobacterium* thermoautotrophicum (Mth), and mutants, variants or derivatives thereof. Accordingly, in some embodiments, the system or kit comprises a thermostable DNA polymerase selected from Taq, Tbr, Tfi, Tfl, KOD, Tru, Tth, Tli, Tac, Tne, Tma, Pfu, Pho, Pwo, ES4, Bca, Bst, Sac, Sso, Poc, Pab, and Mth, or a mutant, variant, or derivative of any thereof. In some embodiments, the DNA polymerase is Taq polymerase. In other embodiments, the DNA polymerase is a polymerase having strand displacement activity, which are especially useful in isothermal amplification reactions. DNA polymerases having strand displacement activity are isolated from a variety of organisms, such as *Bacillus smithii* (Bsm), *Bacillus stearothermophilus* (Bst), *Bacillus subtilis* (Bsu), and *Bacillus subtilis* phage phi29 (phi29), and mutants, variants, or derivatives thereof. Accordingly, in some embodiments, the system or kit comprises a DNA polymerase selected from Bsm, Bst, Bsu, and phi29, or a mutant, variant, or derivative of any thereof.

In some embodiments, DNA polymerases that can be used in accordance with these embodiments include, but are not limited to, commercially available DNA polymerases (e.g., from Boehringer Mannheim Corp., Indianapolis, IN; Life Technologies, Inc., Rockville, MD; MilliporeSigma, St. Louis, MO; New England Biolabs, Inc., Beverley, MA; Perkin Elmer Corp., Norwalk, CT; Pharmacia LKB Biotechnology, Inc., Piscataway, NJ; Promega Corporation, Madison, WI; Qiagen, Inc., Valencia, CA; and Stratagene, La Jolla, CA).

In some embodiments, the system or kit further comprises one or more additional reagents, such as at least one primer or at least one pair of primers for amplification of a nucleic acid target, at least one probe and/or dye to enable detection of amplification, a buffer, a ligase, a reverse transcriptase, a detergent (e.g., non-ionic detergents), nucleotides (dNTPs and/or NTPs), a magnesium salt (e.g., magnesium chloride), or any combination thereof, among other amplification reagents that would be recognized by one of ordinary skill in the art based on the present disclosure.

In some embodiments, the system or kit comprises one or more primers. Generally, a primer is a shorter nucleic acid that is complementary to a longer template. During replication, the primer may be extended, based on the template sequence, to produce a longer nucleic acid that is a complimentary copy of the template. Extension may occur by successive addition of individual nucleotides (e.g., by the action of a polymerase) or by attachment of a block of nucleotides (e.g., by the action of a ligase joining a pair of primers), among others. A primer may be DNA, RNA, an analog thereof (e.g., an artificial nucleic acid), or any combination thereof. A primer may have any suitable length, such as at least about 10 to about 30 nucleotides, or about 15 to about 30 nucleotides, for example, about 15, 16, 17, 18, 19, 20, 21, 22, 23, 24, 25, 26, 27, 28, 29, or 30 nucleotides. Primers are typically synthesized chemically. Primers may be supplied as at least one pair of primers for amplification of at least one nucleic acid target. A pair of primers may be a forward primer and a reverse primer (i.e., a sense primer and an antisense primer) that collectively define the opposing ends (and thus the length) of a resulting amplicon.

In some embodiments, the system or kit provides a pair of primers that specifically detect a microorganism or cell of interest. In some embodiments, the microorganism is a bacterium. In some embodiments, the bacterium is from a genus selected from *Actinomyces, Bacteroides, Bacillus, Bordetella, Campylobacter, Clostridium, Corynebacterium, Enterobacter, Enterococcus, Escherichia, Fusobacterium, Haemophilus, Helicobacter, Klebsiella, Legionella, Leptospira, Listeria, Mycobacterium, Mycoplasma, Neisseria, Pasteurella, Pseudomonas, Staphylococcus, Streptobacillus, Streptococcus, Treponema, Vibrio*, and *Yersinia*. In some embodiments, the microorganism is a virus. In some embodiments, the virus is from a viral family selected from Retroviridae (for example, human immunodeficiency viruses, such as HIV-1 (also referred to as HTLV-III, LAV or HTLV-III/LAV, or HIV-III) and other isolates, such as HIV-LP); Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, Ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arenaviridae (hemorrhagic fever viruses); Reoviridae (for example, reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV)-1 and HSV-2, varicella zoster virus, cytomegalovirus (CMV), herpes viruses); Poxyiridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (for example, Hepatitis C); Norwalk and related viruses, and astroviruses)). In some embodiments, the microorganism is a fungus. In some embodiments, the microorganism is a yeast, such as *Saccharomyces* (e.g., *Saccharomyces cerevisiae*) or *Candida* (e.g., *Candida albicans*). In some embodiments, the cell of interest is a eukaryotic cell, such as a mammalian cell or a plant cell.

The pair of primers can be designed to detect an amplicon of a particular length. For example, the amplicon may be about 200 base pairs to about 1000 base pairs, or about 400 base pairs to about 750 base pairs. For example, in some embodiments, the primers in the system or kit are for an amplicon of at least about 200 base pairs, at least about 300 base pairs, at least about 400 base pairs, at least about 500 base pairs, at least about 600 base pairs, at least about 700 base pairs, at least about 800 base pairs, at least about 900 base pairs, or at least about 1000 base pairs. In some embodiments, the primers in the system or kit are for an amplicon of about 200, 250 300, 350, 400, 450, 500, 550, 600, 650, 700, 750, 800, 850, 900, 950, or 1000 base pairs.

In some embodiments, the system or kit can also include one or more probes, or any nucleic acid connected to at least one label, such as at least one dye. A probe may be a sequence-specific binding partner for a nucleic acid target and/or amplicon. The probe may be designed to enable detection of target amplification based on fluorescence resonance energy transfer (FRET), including one or more nucleic acids connected to a pair of dyes that collectively exhibit fluorescence resonance energy transfer (FRET) when proximate one another. The pair of dyes may provide first and second emitters, or an emitter and a quencher, among others. Fluorescence emission from the pair of dyes changes when the dyes are separated from one another, such as by cleavage of the probe during primer extension (e.g., a 5' nuclease assay, such as with a TAQMAN probe), or when the probe hybridizes to an amplicon (e.g., a molecular beacon probe). The nucleic acid portion of the probe may have any suitable structure or origin, for example, the portion may be a locked nucleic acid, a member of a universal probe library, or the like. In other cases, a probe and one of the primers of a primer pair may be combined in the same molecule. For example, the primer-probe molecule may include a primer sequence at its 3' end and a molecular beacon-style probe at its 5' end. With this arrangement, related primer-probe molecules labeled with different dyes can be used in a multiplexed assay with the same reverse primer to quantify target sequences differing by a single nucleotide (single nucleotide polymorphisms (SNPs)).

In some embodiments, the system or kit can also include one or more labels or reporter molecules. Exemplary dyes used for labeling are fluorescent dyes (fluorophores) and fluorescence quenchers. A reporter includes any compound or set of compounds that reports a condition such as the extent of a reaction. Exemplary reporters comprise at least one dye, such as a fluorescent dye or an energy transfer pair, and/or at least one oligonucleotide. Exemplary reporters for nucleic acid amplification assays may include a probe and/or an intercalating dye (e.g., SYBR Green, ethidium bromide, etc.).

In some embodiments, the system or kit further comprises a magnesium salt, such as magnesium chloride or magnesium sulfate. In some embodiments, the system or kit further comprises magnesium chloride.

In some embodiments, the system or kit further comprises a buffer. The buffer may be provided as a separate component, or one or more of the other system or kit components (e.g., the DNA polymerase) can be provided as a solution in the buffer. Exemplary buffers include tris(hydroxymethyl) aminomethane (Tris) buffers. The buffer can further comprise a salt, such as an ammonium salt (e.g., ammonium chloride or ammonium sulfate), and/or a potassium salt (e.g., potassium chloride). The buffer can be provided at a suitable pH, which may be particularly tailored to the DNA polymerase provided with the system or kit. In some embodiments, the buffer has a pH of about 7.5 to about 10, or about 8.0 to about 9.5.

In some embodiments, the system or kit further comprises a reverse transcriptase, which is used in an RT-PCR reaction to make a complementary DNA (cDNA) from RNA, such that the cDNA can then be amplified in an amplification reaction. RT-PCR reactions may be used for detecting a variety of RNA species, such as RNA from a virus. The system or kit may also further comprise other components for RT-PCR, such as a ribonuclease inhibitor to inhibit degradation of the target during cDNA synthesis.

In some embodiments, kits are provided that contain one or more or all of the components necessary, sufficient, or useful for practicing the methods described herein (e.g., a compound described herein, a DNA polymerase, and amplification reagents). In some embodiments, the kits comprise positive control reagents, negative control reagents, quantitation standard reagents, and internal amplification control reagents. In some embodiments, the kits comprise instructions, which may be written instructions or embodied in a computer readable media. Reagents within the kits may be housed in one or more containers (e.g., tubes) and the collection of kit components may be packaged in one or more boxes or other containers that facilitate shipment and storage of the kit.

4. METHODS OF USE

Embodiments of the present disclosure include methods of amplifying DNA from a sample, wherein the DNA is selectively amplified from viable cells and not from non-viable cells in the sample (i.e., amplification reactions such as viability PCR reactions).

Generally, amplification reactions involve a process of replication or forming a copy (e.g., a direct copy and/or a complimentary copy) of a nucleic acid or a segment thereof. Replication reactions generally involve an enzyme, such as a polymerase and/or a ligase, among others. The nucleic acid and/or segment replicated is a template (and/or a target) for replication. The reactions also generally involve a process of amplification, or a reaction in which replication occurs repeatedly over time to form multiple copies of at least one segment of a template molecule. Amplification may generate an exponential or linear increase in the number of copies as amplification proceeds. Typical amplifications produce a greater than 1,000-fold increase in copy number and/or signal. Exemplary amplification reactions for the assays disclosed herein may include the polymerase chain reaction (PCR) or ligase chain reaction (LCR), each of which is driven by thermal cycling. Thermal cycling generally involves cycles of heating and cooling a reaction mixture to perform successive rounds of denaturation (melting), annealing, and extension. Other exemplary amplification reactions include isothermal amplification methods, which use an enzyme (e.g., a DNA polymerase) having strand-displacement activity.

In some embodiments, the disclosure provides a method of detecting a viable microorganism or cell of interest in the sample, the method comprising:

(a) contacting the sample with a compound described herein (i.e., a compound comprising a NAB moiety, a LDCD moiety, and a NAM moiety), or a salt thereof, to form a first mixture;

(b) contacting the first mixture with an inactivating agent to form a second mixture; and (c) amplifying nucleic acids from the second mixture to produce a detectable signal, wherein the signal is indicative of the presence of a viable organism in the sample.

In some embodiments, the disclosure provides a method of amplifying a nucleic acid from a sample, the method comprising:

(a) contacting the sample with a compound described herein (i.e., a compound comprising a NAB moiety, a LDCD moiety, and a NAM moiety), or a salt thereof, to form a first mixture;

(b) contacting the first mixture with an inactivating agent to form a second mixture; and (c) amplifying nucleic acids from the second mixture.

In some embodiments, the disclosure provides a method of detecting a viable microorganism or cell of interest in the sample, the method comprising:

(a) contacting the sample with a compound described herein (i.e., a compound comprising a NAB moiety, a LDCD moiety, and a NAM moiety), or a salt thereof, to form a first mixture;

(b) removing the compound described herein (i.e., a compound comprising a NAB moiety, a LDCD moiety, and a NAM moiety) from the first mixture to form a second mixture; and (c) amplifying nucleic acids from the second mixture to produce a detectable signal, wherein the signal is indicative of the presence of a viable organism in the sample.

As discussed herein, the compounds disclosed herein do not require a photoactivation step in order to modify nucleic acids (e.g., DNA). This provides advantages to the viability PCR process, particularly in complex or turbid samples, as it can reduce sample-to-sample variability. Accordingly, in some embodiments, the methods described herein do not include a photoactivation step.

Furthermore, the compounds described herein can modify DNA from non-viable cells in a sample, but the LDCD moiety prevents their entry into viable cells. This allows selective labeling of DNA from non-viable cells in the sample without the need for a culturing step to increase the number of live cells in the sample. Accordingly, in some embodiments, the methods described herein do not include a culturing step.

The sample from which the microorganism or cell is detected and/or the nucleic acid is amplified can be any sample for which it would be desirable to amplify nucleic acids selectively from live cells, or to detect a viable microorganism or cell in the sample. In some embodiments, the sample can be obtained from a subject. For example, non-limiting examples of samples obtained from a subject can include skin, heart, lung, kidney, bone marrow, breast, pancreas, liver, muscle, smooth muscle, bladder, gall bladder, colon, intestine, brain, prostate, esophagus, thyroid, serum, saliva, urine, gastric and digestive fluid, tears, stool, semen, vaginal fluid, interstitial fluids derived from tumorous tissue, ocular fluids, sweat, mucus, earwax, oil, glandular secretions, spinal fluid, hair, fingernails, plasma, nasal swab or nasopharyngeal wash, spinal fluid, cerebral spinal fluid, tissue, throat swab, biopsy, placental fluid, amniotic fluid, cord blood, emphatic fluids, cavity fluids, sputum, pus, microbiota, meconium, breast milk, and/or other excretions or body tissues. The sample can also be processed, extracted, or fractionated from any of the foregoing. In other embodiments, the sample is an environmental sample, such as a sample collected from a natural environment (e.g., soil, a body of water, or outdoor air), or an artificial environment (e.g., a clean room, a hospital facility, a food production facility, a laboratory facility, a pharmaceutical facility, a spa, a cooling tower, or an air handling system). In some embodiments, the sample is a food product, a pharmaceutical product, a water sample, or a soil sample.

In some embodiments, the sample can be a sample suspected of containing a viable microorganism, for which it would be desirable to detect the presence of such viable microorganism. For example, in some embodiments, the sample is a sample suspected of containing a bacterium, such as a bacterium from a genus selected from *Actinomyces, Bacteroides, Bacillus, Bordetella, Campylobacter, Clostridium, Corynebacterium, Enterobacter, Enterococcus, Escherichia, Fusobacterium, Haemophilus, Helicobacter, Klebsiella, Legionella, Leptospira, Listeria, Mycobacterium, Mycoplasma, Neisseria, Pasteurella, Pseudomonas, Staphylococcus, Streptobacillus, Streptococcus, Treponema, Vibrio*, and *Yersinia*. For example, in certain embodiments, the bacterium is *Escherichia coli* (e.g., *E. coli* O157:H7), *Legionella pneumophila, Listeria monocytogenes, Mycobacterium tuberculosis, Pseudomonas aeruginosa, Salmonella enterica*, or *Staphylococcus aureus* (e.g., methicillin-resistant *Staphylococcus aureus*). In some embodiments, the sample is a sample suspected of containing a virus, such as a virus from a family selected from Retroviridae, Picornaviridae, Calciviridae, Flaviridae, Coronaviridae, Rhabdoviridae, Filoviridae, Paramyxoviridae, Orthomyxoviridae, Bungaviridae, Arenaviridae, Reoviridae, Birnaviridae, Hepadnaviridae, Parvoviridae, Papovaviridae, Adenoviridae, Herpesviridae, Poxyiridae, and Iridoviridae. In some embodiments, the sample is a sample suspected of containing a fungus, a yeast, or another type of eukaryotic cell such as a mammalian cell or a plant cell.

The methods disclosed herein include a step of contacting a sample with the compound comprising the NAB moiety, the LDCD moiety, and the NAM moiety, to form a first mixture. The contacting step can be conducted by adding the compound to the sample, and incubating the sample for a period of time sufficient to allow the compound to bind to and modify nucleic acids in the sample that are not present in viable cells (i.e., free nucleic acids or nucleic acids in non-viable cells). The contacting step can be conducted for about 5 minutes to about 180 minutes, or about 60 minutes to about 120 minutes, e.g., about 5, 10, 15, 20, 25, 30, 35, 40, 45, 50, 55, 60, 65, 70, 75, 80, 85, 90, 95, 100, 105, 110, 115, or 120 minutes. In some embodiments, step (a) comprises contacting the sample with the compound for about 90 minutes.

The concentration of the compound in the first mixture can range from about 1 micromolar to about 200 micromolar, or about 5 micromolar to about 100 micromolar, e.g., about 5, 10, 15, 20, 25, 30, 35, 40, 45, 50, 55, 60, 65, 70, 75, 80, 85, 90, 95, or about 100 micromolar.

Step (a) can be conducted at any suitable temperature. For example, step (a) can be conducted at room temperature (e.g., about 20-25° C.), or at about 37° C.

In some embodiments, the contacting step of step (a) is conducted by adding a composition comprising the compound to the sample, for example, a composition comprising the compound and a solvent. In some embodiments, the solvent is water. In some embodiments, the solvent is an organic solvent such as dimethylsulfoxide (DMSO). Use of a solvent such as DMSO may have particular advantages in samples comprising Gram-negative bacteria, as discussed above.

Step (b) of the method comprises removing, inactivating, or otherwise neutralizing the compound in the first mixture to form a second mixture. In some embodiments, step (b) comprises contacting the first mixture with an inactivating agent to form a second mixture. This step serves to inactivate the NAM moiety in any excess compound in the first mixture, which renders it unable to modify any further nucleic acids and ensure optimal performance in the subsequent amplification reaction. For example, if excess compound remained after step (a), then a subsequent lysis of viable cells in the sample would be modified by the excess compound and would not be available for the amplification reaction. In such embodiments, the inactivating agent will depend on the particular NAM moiety in the compound. For example, when the NAM moiety is a nitrogen mustard moiety, the inactivating agent can be a nucleophilic compound that can effectively displace the chloride groups, such as an amine or a thiol. Accordingly, in some embodiments, the inactivating agent is a compound comprising a thiol, such as cysteine, glutathione, or DTT. In some embodiments, the inactivating agent is an amine-containing compound, such as an amine-containing buffer. Examples of amine-containing buffers include tris(hydroxymethyl)aminomethane (Tris) and triethanolamine-containing buffers. In some embodiments, the inactivating agent is a dNTP or mixture of dNTPs. In some embodiments, the inactivating agent is a nucleotide, such as guanine. In other embodiments, the inactivating step serves to inhibit the NAB moiety, thereby preventing the compounds from binding to and modifying the DNA. In such embodiments, the inactivating agent will depend on the particular NAB moiety in the compound yet other embodiments, the compound is physically removed from the first mixture to form the second mixture, for example, by washing the sample.

Step (c) comprises amplifying nucleic acids from the second mixture to produce a detectable signal, wherein the signal is indicative of the presence of a viable organism in the sample. The amplification reaction can be performed in a variety of ways. For example, in some embodiments, the amplification step (c) comprises steps of: (i) lysing cells in the second mixture to form a lysed sample; (ii) adding a DNA polymerase and amplification reagents to the lysed sample to form a mixture; and (iii) subjecting the mixture to a thermal cycling protocol to amplify the nucleic acid from the sample. In other embodiments, the amplification step (c) comprises steps of: (i) lysing cells in the second mixture to form a lysed sample; (ii) adding a DNA polymerase and amplification reagents to the lysed sample to form a mixture; and (iii) subjecting the mixture to an isothermal amplification reaction to amplify the nucleic acid from the sample.

The lysis step exposes the DNA from the viable cells in the sample so that it can be amplified in the amplification reaction. Any suitable method of cell lysis can be used in the methods, e.g., chemical lysis, electrochemical lysis, acoustic lysis (i.e., sonication), mechanical lysis, or heat lysis.

In some embodiments, the method further comprises a step of removing contaminants and/or cellular debris from the lysed sample prior to adding the DNA polymerase and amplification reagents. For example, this step may involve purifying DNA from the sample to generate a purified DNA sample to which the DNA polymerase and amplification reagents can be added. The DNA can be purified by any conventional means, for example, using organic extraction followed by ethanol precipitation, a salt-based precipitation method, magnetic particle-based isolation, or stationary phase adsorption methods.

The DNA is amplified in an amplification reaction such as PCR. Generally, PCR includes any nucleic acid amplification reaction that relies on alternating cycles of heating and cooling (i.e., thermal cycling) to achieve successive rounds of replication. PCR may be performed by thermal cycling between two or more temperature set points, such as a higher melting (denaturation) temperature and a lower annealing/extension temperature, or among three or more temperature set points, such as a higher melting temperature, a lower annealing temperature, and an intermediate extension temperature, among others. PCR generally produces an exponential increase in the amount of a product amplicon over successive cycles.

Any suitable PCR methodology or combination of methodologies may be utilized in the embodiments disclosed herein such as allele-specific PCR, assembly PCR, asymmetric PCR, digital PCR, endpoint PCR, hot-start PCR, in situ PCR, intersequence-specific PCR, inverse PCR, linear after exponential PCR, ligation-mediated PCR, methylation-specific PCR, miniprimer PCR, multiplex ligation-dependent probe amplification, multiplex PCR, nested PCR, overlap-extension PCR, polymerase cycling assembly, qualitative PCR, quantitative PCR, real-time PCR, RT-PCR, single-cell PCR, solid-phase PCR, thermal asymmetric interlaced PCR, touchdown PCR, universal fast walking PCR, or any combination thereof, among others.

In some embodiments, the DNA is amplified in an isothermal amplification reaction, which generally includes any nucleic acid amplification reaction that relies on an enzyme, rather than thermal denaturation, to directly unwind the DNA double helix in order to synthesize complementary strands. Examples of isothermal amplification methods include loop-mediated isothermal amplification (LAMP), helicase-dependent amplification (HAD), rolling circle amplification (RCA), multiple displacement amplification (MDA), nucleic acid sequence-based amplification (NASBA), whole genome amplification (WGA), and recombinase polymerase amplification (RPA).

The amplification can be conducted by adding amplification reagents and a DNA polymerase to form a mixture. DNA polymerases that can be used in accordance with these embodiments include, but are not limited to, any polymerase capable of replicating a DNA molecule. In some embodiments, the DNA polymerase is a thermostable polymerase, which is especially useful in PCR applications. In some embodiments, the thermostable DNA polymerase is selected from Taq, Tbr, Tfi, Tfl, KOD, Tru, Tth, Tli, Tac, Tne, Tma, Pfu, Pho, Pwo, ES4, Bca, Bst, Sac, Sso, Poc, Pab, and Mth, or a mutant, variant, or derivative of any thereof. In some embodiments, the DNA polymerase is Taq polymerase. In some embodiments, the DNA polymerase is a polymerase having strand displacement activity, which is useful in isothermal amplification applications. In some embodiments, the DNA polymerase having strand displacement activity is selected from Bsm, Bst, Bsu, and phi29 DNA polymerases.

The one or more additional amplification reagents can be selected from at least one primer or at least one pair of primers for amplification of a nucleic acid target, at least one probe and/or dye to enable detection of amplification, a buffer, a ligase, a reverse transcriptase, a detergent (e.g., non-ionic detergents), nucleotides (dNTPs and/or NTPs), a magnesium salt (e.g., magnesium chloride), or any combination thereof, among other amplification reagents that would be recognized by one of ordinary skill in the art based on the present disclosure. For example, in some embodiments, the amplification reagents comprise at least one primer, deoxynucleotide triphosphates (dNTPs), a buffer, and a magnesium salt.

In some embodiments, the amplification reagents include one or more primers. A primer may be DNA, RNA, an analog thereof (e.g., an artificial nucleic acid), or any combination thereof. A primer may have any suitable length, such as at least about 10 to about 30 nucleotides, or about 15 to about 30 nucleotides, for example, about 15, 16, 17, 18, 19, 20, 21, 22, 23, 24, 25, 26, 27, 28, 29, or 30 nucleotides. Primers are typically synthesized chemically. Primers may be supplied as at least one pair of primers for amplification of at least one nucleic acid target. A pair of primers may be a forward primer and a reverse primer (i.e., a sense primer and an antisense primer) that collectively define the opposing ends (and thus the length) of a resulting amplicon.

In some embodiments, the amplification reagents include a pair of primers that specifically detect an organism or cell type of interest. In some embodiments, the organism is a microorganism. In some embodiments, the microorganism is a bacterium. In some embodiments, the bacterium is from a genus selected from *Actinomyces, Bacteroides, Bacillus, Bordetella, Campylobacter, Clostridium, Corynebacterium, Enterobacter, Enterococcus, Escherichia, Fusobacterium, Haemophilus, Helicobacter, Klebsiella, Legionella, Leptospira, Listeria, Mycobacterium, Mycoplasma, Neisseria, Pasteurella, Pseudomonas, Staphylococcus, Streptobacillus, Streptococcus, Treponema, Vibrio*, and *Yersinia*. In some embodiments, the microorganism is a virus. In some embodiments, the virus is from a family selected from Retroviridae, Picornaviridae, Calciviridae, Flaviridae, Coronaviridae, Rhabdoviridae, Filoviridae, Paramyxoviridae, Orthomyxoviridae, Bungaviridae, Arenaviridae, Reoviridae, Birnaviridae, Hepadnaviridae, Parvoviridae, Papovaviridae, Adenoviridae, Herpesviridae, Poxyiridae, and Iridoviridae. In some embodiments, the microorganism is a fungus. In some embodiments, the microorganism is a yeast. In some embodiments, the cell type of interest is a plant cell or mammalian cell.

The pair of primers can be designed to detect an amplicon of a particular length. For example, the amplicon may be about 200 base pairs to about 1000 base pairs, or about 400 base pairs to about 750 base pairs. For example, in some embodiments, the primers are for an amplicon of at least about 200 base pairs, at least about 300 base pairs, at least about 400 base pairs, at least about 500 base pairs, at least about 600 base pairs, at least about 700 base pairs, at least about 800 base pairs, at least about 900 base pairs, or at least about 1000 base pairs. In some embodiments, the primers are for an amplicon of about 200, 250 300, 350, 400, 450, 500, 550, 600, 650, 700, 750, 800, 850, 900, 950, or 1000 base pairs.

In some embodiments, the amplification reagents comprise a magnesium salt, such as magnesium chloride or magnesium sulfate. In some embodiments, the amplification reagents comprise magnesium chloride.

In some embodiments, the amplification reagents comprise a buffer. Exemplary buffers include tris(hydroxymethyl)aminomethane (Tris) buffers. The buffer can further comprise a salt, such as an ammonium salt (e.g., ammonium chloride or ammonium sulfate), and/or a potassium salt (e.g., potassium chloride). The pH of the buffer may be particularly tailored to the DNA polymerase being used in the amplification reaction. In some embodiments, the buffer has a pH of about 7.5 to about 10, or about 8.0 to about 9.5.

In some embodiments, such as embodiments of the methods to detect a viable microorganism in a sample, the amplification reagents comprise one or more probes, or any nucleic acid connected to at least one label, such as at least one dye. A probe may be a sequence-specific binding partner for a nucleic acid target and/or amplicon. The probe may be designed to enable detection of target amplification based on fluorescence resonance energy transfer (FRET), including one or more nucleic acids connected to a pair of dyes that collectively exhibit fluorescence resonance energy transfer (FRET) when proximate one another. The pair of dyes may provide first and second emitters, or an emitter and a quencher, among others. Fluorescence emission from the pair of dyes changes when the dyes are separated from one another, such as by cleavage of the probe during primer extension (e.g., a 5' nuclease assay, such as with a TAQMAN probe), or when the probe hybridizes to an amplicon (e.g., a molecular beacon probe). The nucleic acid portion of the probe may have any suitable structure or origin, for example, the portion may be a locked nucleic acid, a member of a universal probe library, or the like. In other cases, a probe and one of the primers of a primer pair may be combined in the same molecule. For example, the primer-probe molecule may include a primer sequence at its 3' end and a molecular beacon-style probe at its 5' end. With this arrangement, related primer-probe molecules labeled with different dyes can be used in a multiplexed assay with the same reverse primer to quantify target sequences differing by a single nucleotide (single nucleotide polymorphisms (SNPs)).

In some embodiments, the amplification reagents also include one or more labels or reporter molecules. Exemplary dyes used for labeling are fluorescent dyes (fluorophores) and fluorescence quenchers. A reporter includes any compound or set of compounds that reports a condition such as the extent of a reaction. Exemplary reporters comprise at least one dye, such as a fluorescent dye or an energy transfer pair, and/or at least one oligonucleotide. Exemplary reporters for nucleic acid amplification assays may include a probe and/or an intercalating dye (e.g., SYBR Green, ethidium bromide, etc.).

In accordance with the embodiments provided herein, concentrations of the amplification reagents described above can vary, depending on specific reaction conditions and reagents used, as well as the desired target to be amplified. One of skill in the art would readily recognize that any specific concentrations or concentration ranges provided herein for any amplification reagents, including concentration ranges pertaining to the compounds of the present disclosure, will vary depending on the specific reaction conditions and reagents used and are not meant to be limiting.

In some embodiments, such as those involving PCR, after adding the DNA polymerase and the amplification reagents to form the mixture, the method further comprises heating the mixture to a temperature of at least 90° C. to activate the DNA polymerase prior to subjecting the mixture to the thermal cycling protocol. For example, the DNA polymerase may initially be unreactive at ambient temperature, via inhibition through antibody interaction or other modification. An initial step activates the DNA polymerization by causing dissociation from the inhibitor. In this step, the mixture can be subjected to a temperature of at least 90° C., e.g., about 90° C. to about 96° C., e.g., about 90° C., about 91° C., about 92° C., about 93° C., about 94° C., about 95° C., or about 96° C. This heating step can be conducted for about 1 minute to about 10 minutes, or about 2 minutes to about 5 minutes, e.g., about 1, 2, 3, 4, 5, 6, 7, 8, 9, or 10 minutes.

In some embodiments, the nucleic acid is amplified using a thermal cycling protocol. In some embodiments, the thermal cycling protocol comprises:

(1) a denaturation step comprising subjecting the mixture to a temperature of about 90-96° C.;

(2) an annealing step comprising subjecting the mixture to a temperature of about 45-68° C.; and (3) an extension step comprising subjecting the mixture to a temperature of about 50-72° C.;

wherein the sequence of steps (1)-(3) is repeated about 10 or more times in succession.

The denaturation step comprises subjecting the mixture to a temperature of about 90-96° C. to denature the double-stranded DNA and allow for subsequent annealing of the primers. For example, the mixture can be subjected to a temperature of about 90° C. to about 96° C., e.g., about 90° C., about 91° C., about 92° C., about 93° C., about 94° C., about 95° C., or about 96° C. This step can be conducted for about 15 seconds to about 60 seconds, e.g., about 15 seconds, about 30 seconds, about 45 seconds, or about 60 seconds.

The annealing step comprises subjecting the mixture to a temperature of about 45-68° C. to allow the primers to bind to the complementary sequence on the denatured DNA. The optimal annealing temperature will depend on the particular primers being used, and is typically a temperature that is about 5° C. lower than the primer melting temperature (Tm). For example, the mixture can be subjected to a temperature of about 45° C. to about 68° C., e.g., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., or about 68° C. The annealing step can be conducted for about 15 seconds to about 60 seconds, e.g., about 15 seconds, about 30 seconds, about 45 seconds, or about 60 seconds.

The extension step comprises subjecting the mixture to a temperature of about 50-72° C. to allow the DNA polymerase to extend the DNA strands starting from the annealed primers. The extension temperature will depend on the particular DNA polymerase being used, and the extension time will depend on the length of the amplicon. A typical extension temperature is about 50° C. to about 72° C., e.g., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., or about 72° C. A typical extension time is about 1 minute per kilobase of DNA. For example, the extension step can be conducted for about 15 seconds to about 2 minutes, e.g., about 15 seconds, about 30 seconds, about 45 seconds, about 60 seconds, about 75 seconds, about 90 seconds, about 105 seconds, or about 120 seconds.

The sequence of denaturation, annealing, and extension steps can be repeated about 10 or more times in succession, e.g., about 10, 15, 20, 25, 30, 35, 40, 45, or 50 times in succession.

In other embodiments, the thermal cycling protocol may comprise only two steps, a denaturation step and a combined annealing/extension step. For example, in some embodiments the thermal cycling protocol comprises:

(1a) a denaturation step comprising subjecting the mixture to a temperature of 90-96° C.;

(2a) an annealing/extension step comprising subjecting the mixture to a temperature of 45-70° C.; and wherein the sequence of steps (1a)-(2a) is repeated 10 or more times in succession.

In these embodiments, the annealing/extension step comprises subjecting the mixture to a temperature of about 45° C. to about 70° C., e.g., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., or about 70° C. The annealing/extension step can be conducted for about 15 seconds to about 2 minutes, e.g., about 15 seconds, about 30 seconds, about 45 seconds, about 60 seconds, about 75 seconds, about 90 seconds, about 105 seconds, or about 120 seconds.

The sequence of denaturation and annealing/extension steps can be repeated about 10 or more times in succession, e.g., about 10, 15, 20, 25, 30, 35, 40, 45, or 50 times in succession.

In some embodiments, the nucleic acid is amplified using an isothermal amplification protocol.

In methods of detecting a viable microorganism or cell in the sample, the method produces a detectable signal, wherein the signal is indicative of the presence of a viable organism or cell in the sample. In some embodiments of such methods, the method further comprises detecting the detectable signal from the sample. The specific detection step will depend on the probe and/or dye used in the method. Any suitable detection method can be used, such as photochemical, biochemical, spectroscopic, immunochemical, electrical, optical, or chemical means. In some embodiments, the detection step is a fluorescence detection step. For example, in some embodiments, the amplified products can be directly detected using fluorescence. In some embodiments, a fluorescent probe for the amplified products can be detected using fluorescence.

In some embodiments, the detection is performed using a spectrophotometric thermal cycler. Such thermal cyclers are commercially available from, for example, Agilent (e.g., AriaDx and AriaMx instruments), Applied Biosystems (e.g., QuantStudio® systems), Bio-Rad (e.g., CFX systems), Cepheid (e.g., SmartCycler®), Roche (e.g., LightCycler® systems), and Stratagene (e.g., Mx3005p).

In some embodiments, the disclosure provides a method of removing nucleic acids from a sample, the method comprising contacting the sample with a compound described herein (i.e., a compound comprising a NAB moiety, a LDCD moiety, and a NAM moiety). In some embodiments of such methods, the compound is immobilized on a solid support, such as a bead, a resin, or a membrane. Such methods can be used with any sample for which it would be desirable to remove free nucleic acids. For example, certain reagents or solutions intended for use as human injectables may be treated with the compounds described herein to remove free DNA.

5. EXAMPLES

It will be readily apparent to those skilled in the art that other suitable modifications and adaptations of the methods of the present disclosure described herein are readily applicable and appreciable and may be made using suitable equivalents without departing from the scope of the present disclosure or the aspects and embodiments disclosed herein. The disclosure will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

Example 1

Viability PCR Workflow

A diagram of the viability PCR (vPCR) workflow described in this application is shown in FIG. 1. In this procedure, live-cell impermeable nucleic acid-modifying compounds are incubated with a mixture of bacterial cells, entering only dead/dying cells due to the permeability of compromised cell membranes. As a result, only nucleic acid from non-viable cells is covalently crosslinked, preventing subsequent amplification via PCR. Therefore, the signal observed in a vPCR detection assay is derived exclusively from viable cells. Dead cells are notated by perforated grey membranes and live cells are notated by intact purple membranes.

Example 2

Compound Syntheses

Abbreviations used in this example include the following: Ac is acetyl; ACN is acetonitrile; DIPEA is N,N-diisopropylethylamine; DMF is N,N-dimethylformamide; HATU is (1-[bis(dimethylamino)methylene]-1H-1,2,3-triazolo[4,5-b] pyridinium 3-oxide hexafluorophosphate; HPLC is high performance liquid chromatography; RT is room temperature; TFA is trifluoroacetic acid; TIPS is triisopropylsilane; TMS is trimethylsilyl; and TSTU is N,N,N',N'-tetramethyl-O—(N-succinimidyl)uronium tetrafluoroborate.

Compound CS0729

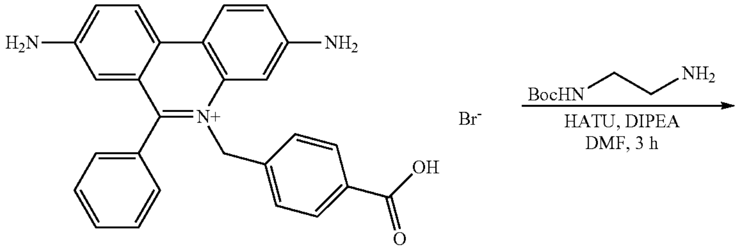

-continued

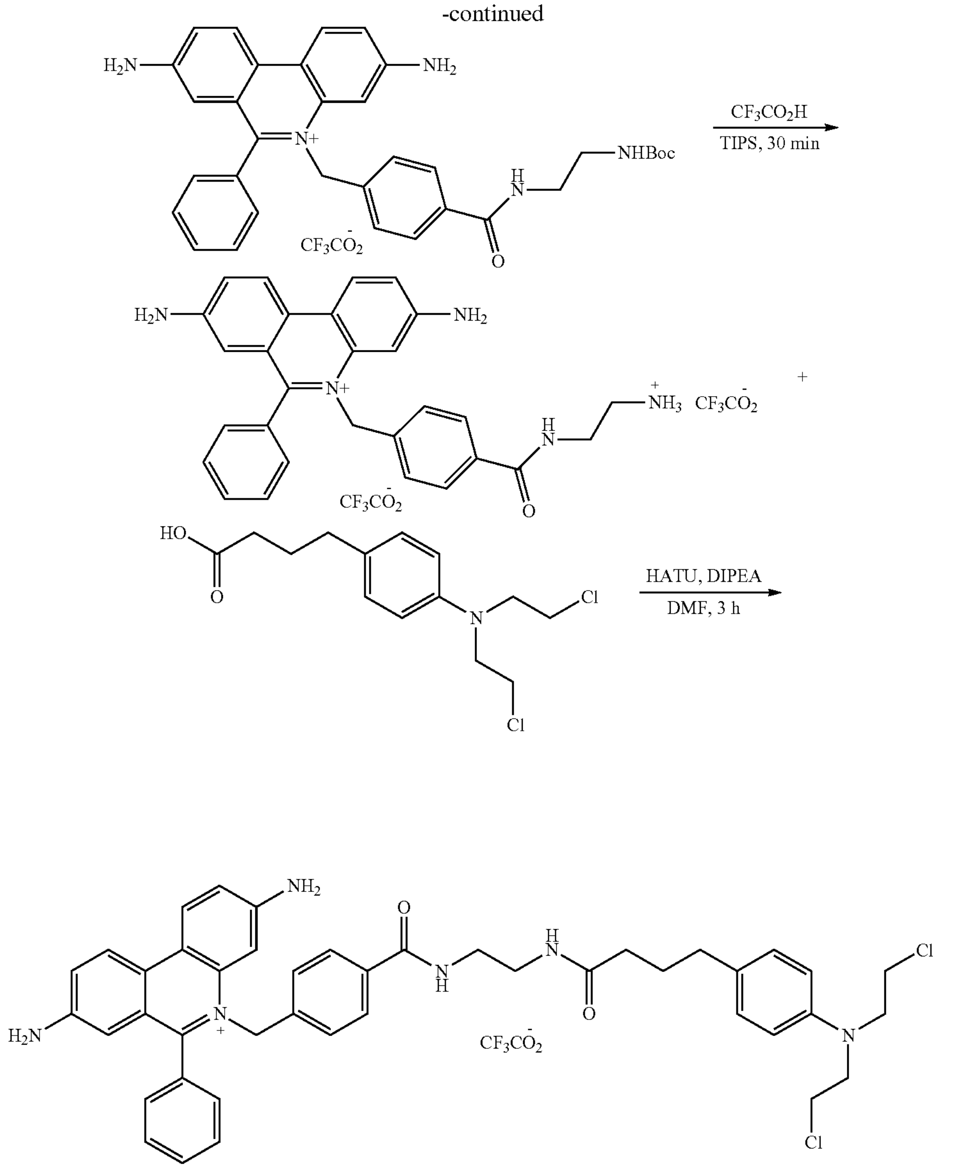

CS0729

Step 1: 3,8-diamino-5-(4-carboxybenzyl)-6-phenylphenanthridin-5-ium bromide (50 mg, 0.1 mmol, 1.0 equiv) was added to a solution of tert-butyl (2-aminoethyl) carbamate (24 mg, 0.15 mmol, 1.5 equiv), DIPEA (39 mg, 0.3 mmol, 3.0 equiv) and HATU (57 mg, 0.15 mmol, 1.5 equiv) in DMF (2 mL). The solution was stirred at RT for 3 h and quenched by addition of 2 mL of $CH_3CN$/0.1% TFA in $H_2O$ (1/1). The mixture was then purified by reverse phase HPLC to afford 3,8-diamino-5-(4-((2-((tert-butoxycarbonyl) amino)-ethyl)carbamoyl)benzyl)-6-phenylphenanthridin-5-ium 2,2,2-trifluoroacetate.

Step 2: 3,8-diamino-5-(4-((2-((tert-butoxycarbonyl) amino)-ethyl)carbamoyl)benzyl)-6-phenylphenanthri-din-5-ium 2,2,2-trifluoroacetate (67.5 mg, 0.1 mmol, 1.0 equiv) was dissolved in TFA (1 mL) and TIPS (0.1 mL) and stirred for 30 min. The reaction was concentrated in vacuo and purified by reverse phase HPLC to afford 5-(4-((2-(14-azaneyl)ethyl)carbamoyl)benzyl)-3,8-diamino-6-phenylphenanthridin-5-ium 2,2,2-trifluoroacetate.

Step 3: 5-(4-((2-(14-azaneyl)ethyl)carbamoyl)benzyl)-3,8-diamino-6-phenylphenanthridin-5-ium 2,2,2-trifluoroacetate (69 mg, 0.1 mmol, 1.0 equiv) was added to a solution of 4-(4-(bis(2-chloroethyl)amino)-phenyl)butanoic acid (33 mg, 0.11 mmol, 1.1 equiv), HATU (42 mg, 0.11 mmol, 1.1 equiv) and DIPEA (39 mg, 0.3 mmol, 3.0 equiv) in DMF (2 mL). The solution was stirred at RT for 3 h and quenched by addition of 2 mL of $CH_3CN$/0.1% TFA in $H_2O$ (1/1). The mixture was then purified by reverse phase HPLC to afford 3,8-diamino-5-(4-((2-(4-(4-(bis(2-chloroethyl)amino)phenyl)butanamido)ethyl)carbamoyl)-benzyl)-6-phenylphenanthridin-5-ium 2,2,2-trifluoroacetate (CS0729).

Compounds CS0727, CS0775, CS0776, CS0777, CS0935, and CS0942 were synthesized analogously using the above procedure; structures and characterization data are shown in Table 1.

TABLE 1
| Compound | Structure | MS (M+) |
|---|---|---|
| CS0729 | 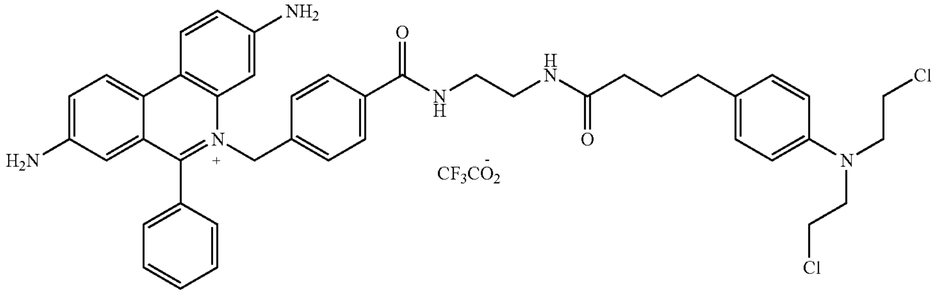 | 747.3 |
| CS0727 | 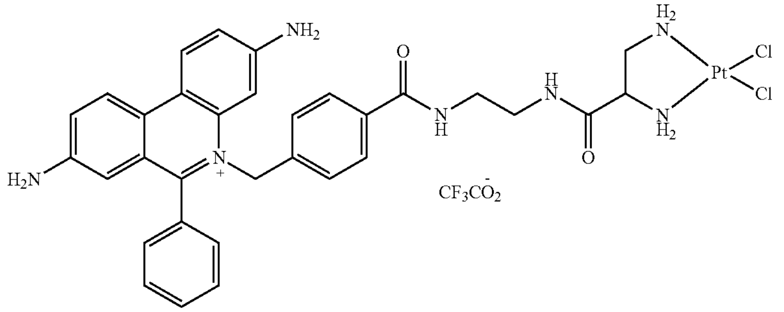 | 813.2 |
| CS0775 | 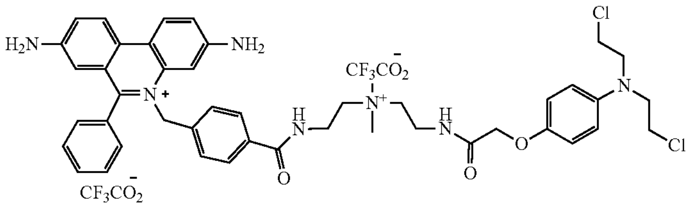 | 403.7 |
| CS0776 | 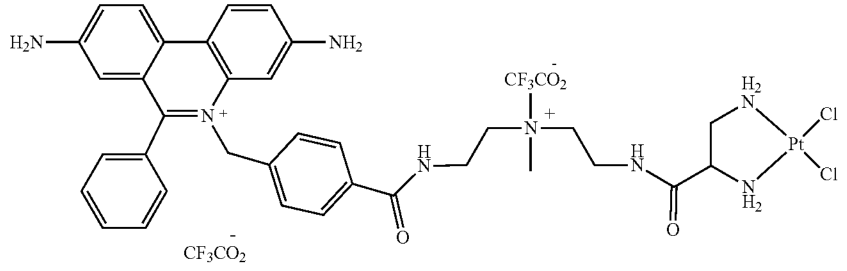 | 442.6 |
| CS0777 | 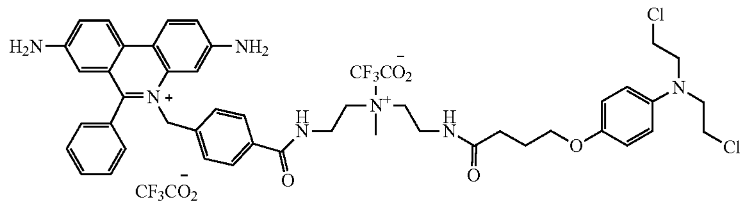 | 417.7 |

TABLE 1-continued
| Compound | Structure | MS (M+) |
| --- | --- | --- |
| CS0935 | 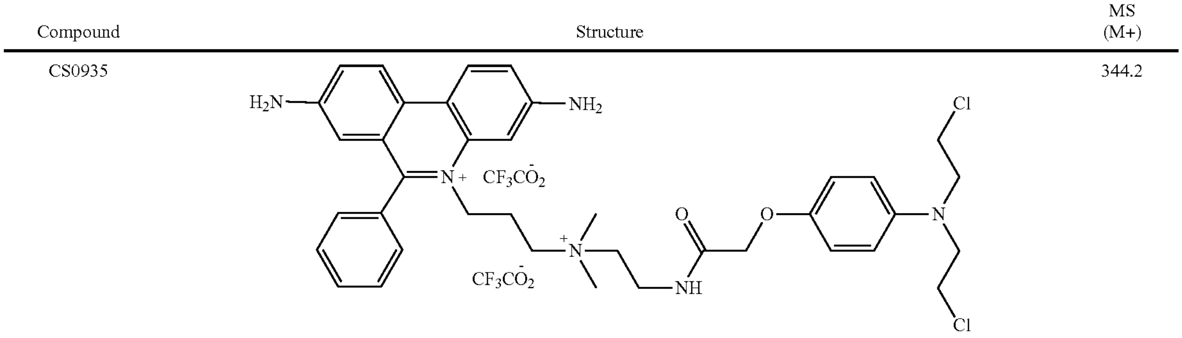 | 344.2 |
| CS0942 | 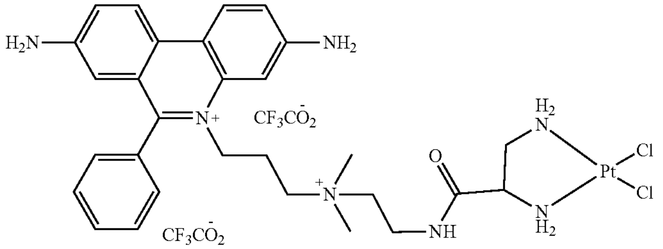 | 383.1 |
Compound CS0733
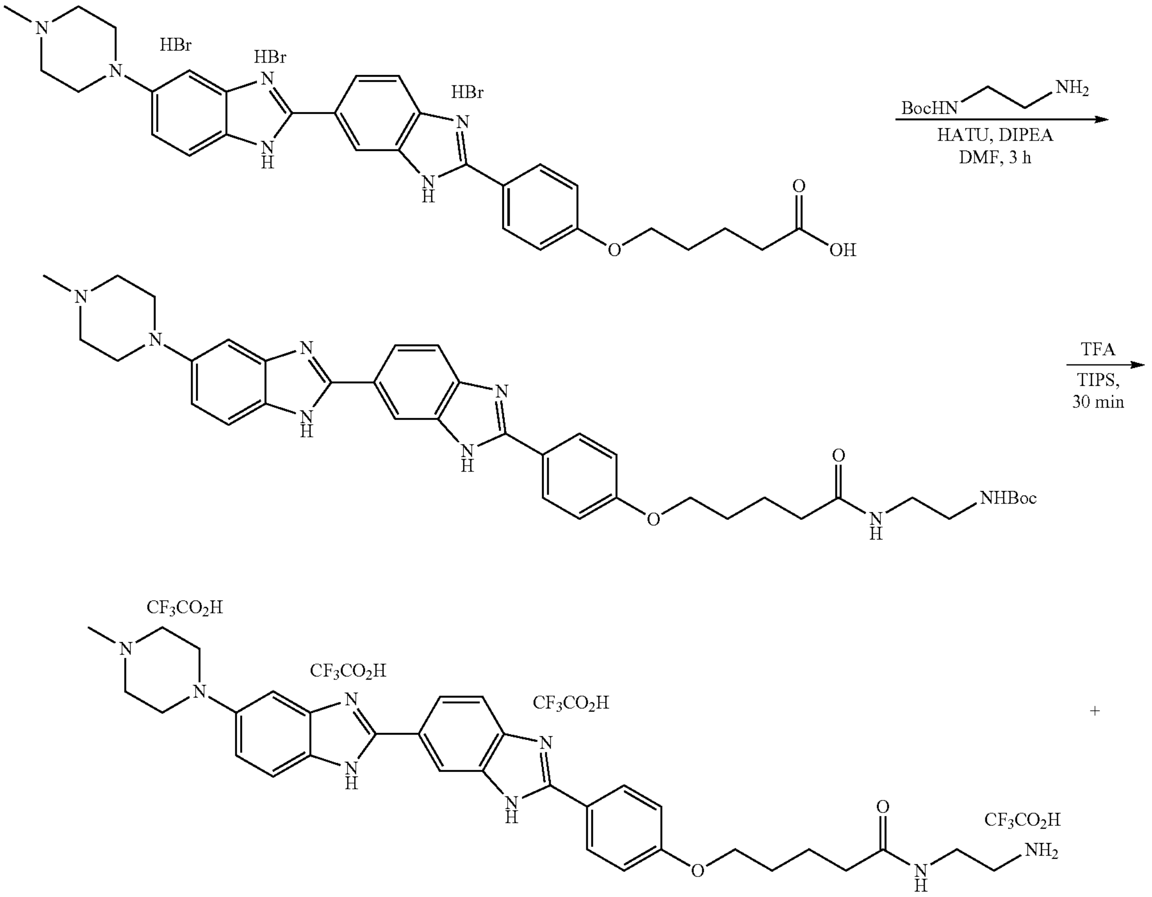

-continued

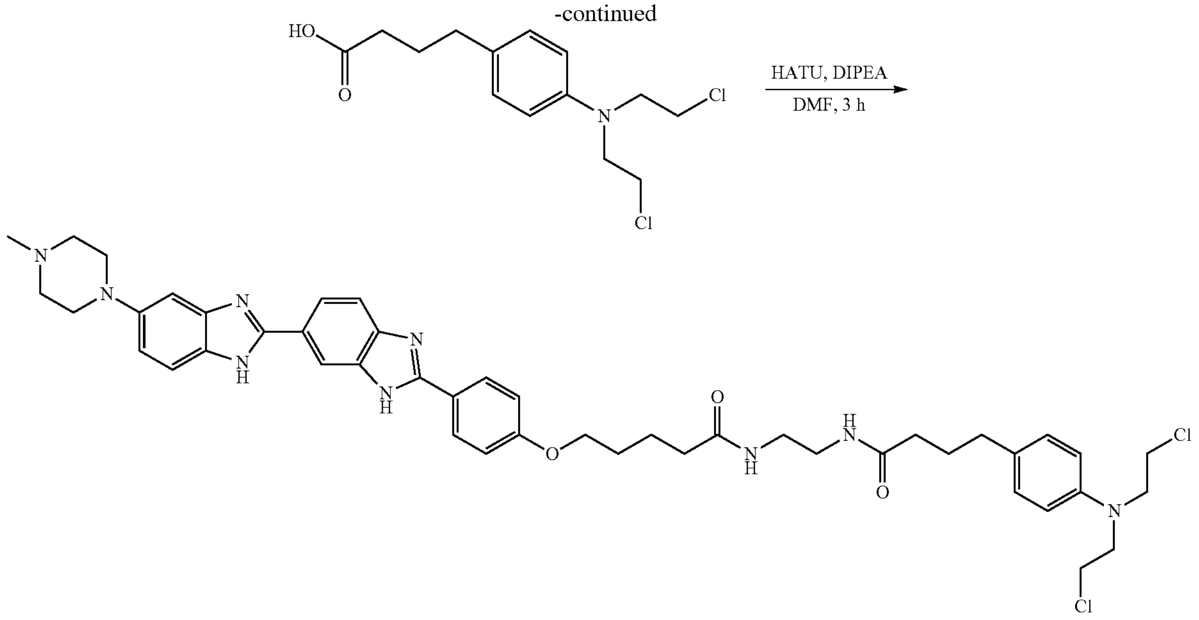

CS0733

Step 1: 5-(4-(5-(4-methylpiperazin-1-yl)-1H,3'H-[2,5'-bibenzo[d]imidazol]-2'-yl)phenoxy)pentanoic acid trihydrobromide (76.6 mg, 0.1 mmol, 1.0 equiv) was added to a solution of tert-butyl (2-aminoethyl)carbamate (24 mg, 0.15 mmol, 1.5 equiv), DIPEA (78 mg, 0.6 mmol, 6.0 equiv) and HATU (57 mg, 0.15 mmol, 1.5 equiv) in DMF (2 mL). The solution was stirred at RT for 3 h and quenched by addition of 2 mL of $CH_3CN$/0.1% TFA in $H_2O$ (1/1). The mixture was then purified via silica gel purification to afford tert-butyl (2-(5-(4-(5-(4-methylpiperazin-1-yl)-1H,3'H-[2,5'-bibenzo [d]imidazol]-2'-yl)phenoxy)pentanamido)ethyl)carbamate.

Step 2: tert-butyl (2-(5-(4-(5-(4-methylpiperazin-1-yl)-1H,3'H-[2,5'-bibenzo[d]imidazol]-2'-yl)phenoxy)-pentanamido)ethyl)carbamate (67 mg, 0.1 mmol, 1.0 equiv) was dissolved in TFA (1 mL) and TIPS (0.1 mL) and stirred for 30 min. The reaction was concentrated in vacuo and purified by reverse phase HPLC to afford N-(2-aminoethyl)-5-(4-(5-(4-methylpiperazin-1-yl)-1H,3'H-[2,5'-bibenzo[d]imidazol]-2'-yl)phenoxy)pentanamide tetrakis(2,2,2-trifluoroacetate).

Step 3: N-(2-aminoethyl)-5-(4-(5-(4-methylpiperazin-1-yl)-1H,3'H-[2,5'-bibenzo[d]imidazol]-2'-yl)phen-oxy)pentanamide tetrakis(2,2,2-trifluoroacetate) (101 mg, 0.1 mmol, 1.0 equiv) was added to a solution of 4-(4-(bis(2-chloroethyl)amino)-phenyl)butanoic acid (33 mg, 0.11 mmol, 1.1 equiv), HATU (42 mg, 0.11 mmol, 1.1 equiv) and DIPEA (117 mg, 0.9 mmol, 9.0 equiv) in DMF (2 mL). The solution was stirred at RT for 3 h and concentrated in vacuo. The mixture was then purified on normal phase silica gel to afford (CS0733).

Compound CS0717 was synthesized analogously using the above procedure; structures and characterization data are shown in Table 2.

TABLE 2

| Compound | Structure | MS (M+) |
|---|---|---|
| CS0733 | 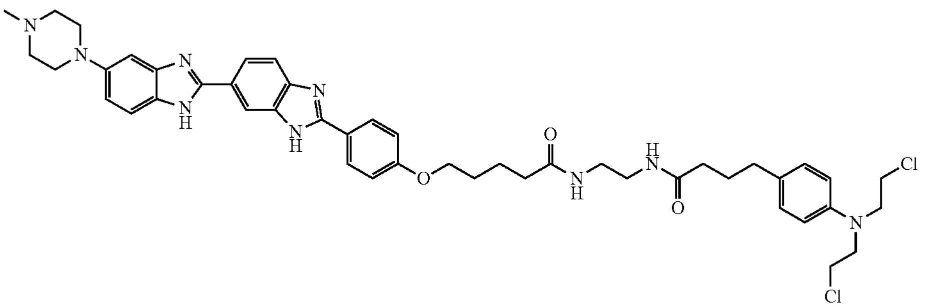 [SMILES: CN1CCN(c2ccc3[nH]c(-c4ccc5nc(-c6ccc(OCCCCC(=O)NCCNC(=O)CCCc7ccc(N(CCCl)CCCl)cc7)cc6)[nH]c5c4)nc3c2)CC1] | 852.9 |

TABLE 2-continued
| Compound | Structure | MS (M+) |
| --- | --- | --- |
| CS0717 | 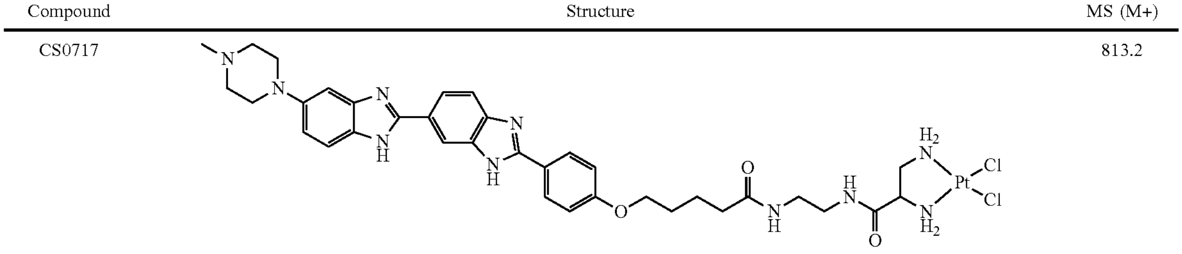 | 813.2 |
Compound CS0868
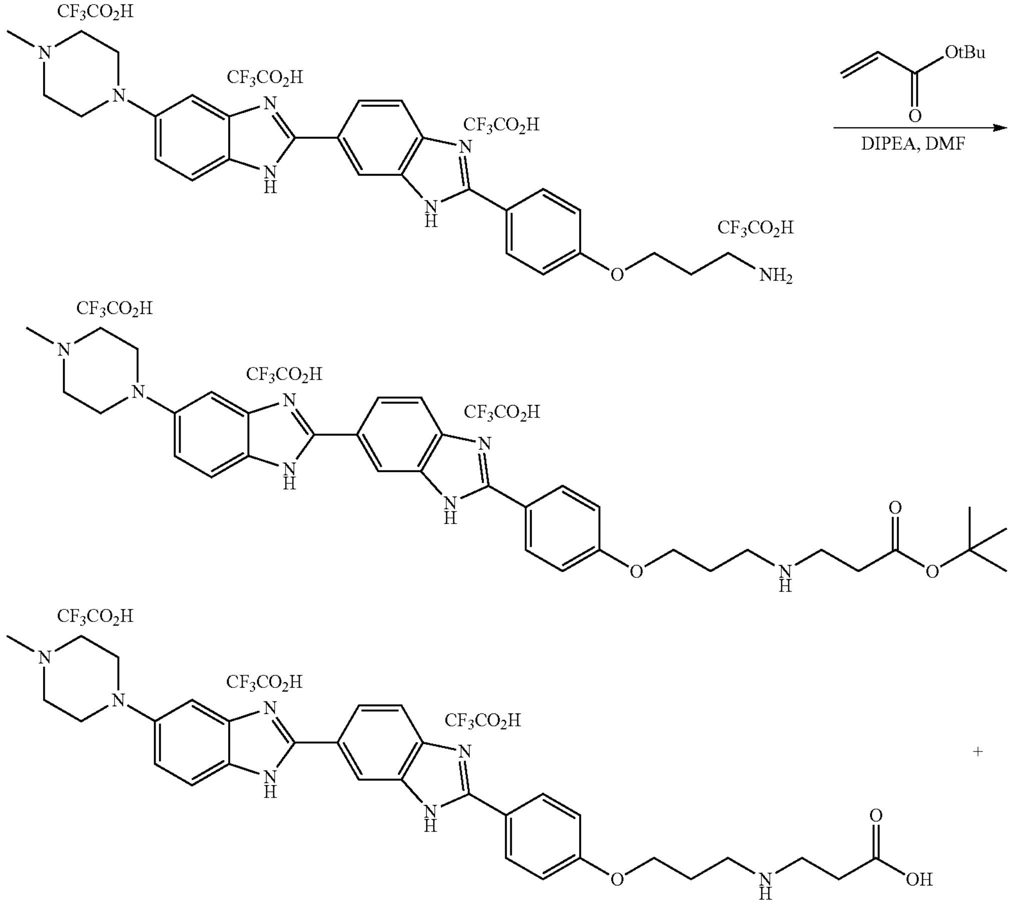
+
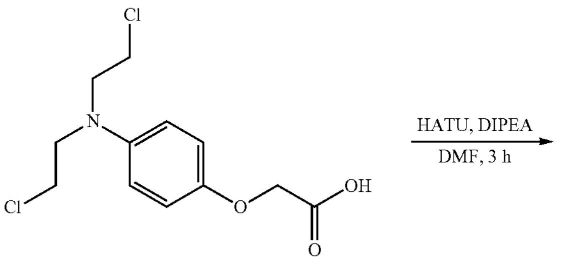

-continued

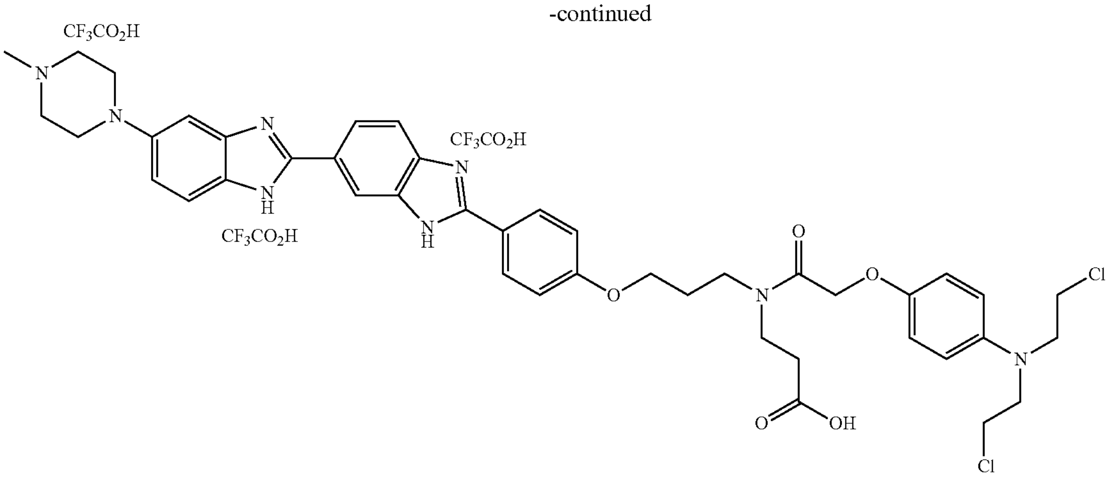

CS0868

Step 1: 3-(4-(5-(4-methylpiperazin-1-yl)-1H,3'H-[2,5'-bibenzo[d]imidazol]-2'-yl)phenoxy)propan-1-amine tetrakis (2,2,2-trifluoroacetate) (93.7 mg, 0.1 mmol, 1.0 equiv) in DMF (1 mL) was added to a solution of tert-butyl acrylate (39 mg, 0.3 mmol, 3.0 equiv) and DIPEA (65 mg, 0.5 mmol, 5.0 equiv) in DMF (1 mL). The solution was stirred at RT for 48 h. The product was isolated using reverse phase HPLC to afford tert-butyl 3-((3-(4-(5-(4-methylpiperazin-1-yl)-1H,3'H-[2,5'-bibenzo[d]imidazol]-2'-yl)phenoxy)propyl)-amino)propanoate tris(2,2,2-trifluoroacetate).

Step 2: tert-butyl 3-((3-(4-(5-(4-methylpiperazin-1-yl)-1H,3'H-[2,5'-bibenzo[d]imidazol]-2'-yl)phenoxy)-propyl)-amino)propanoate tris(2,2,2-trifluoroacetate) (95 mg, 0.1 mmol, 1.0 equiv) was dissolved in TFA (1 mL) and TIPS (0.1 mL) and stirred for 30 min. The reaction was concentrated in vacuo and purified by reverse phase HPLC to afford 2,2,2-trifluoroacetic acid compound with 3-((3-(4-(5-(4-methylpiperazin-1-yl)-1H,3'H-[2,5'-bibenzo[d]imidazol]-2'-yl)phenoxy)propyl)amino)propanoic acid (4:1).

Step 3: N-(2-aminoethyl)-5-(4-(5-(4-methylpiperazin-1-yl)-1H,3'H-[2,5'-bibenzo[d]imidazol]-2'-yl)phen-oxy)pentanamide tetrakis(2,2,2-trifluoroacetate) (101 mg, 0.1 mmol, 1.0 equiv) was added to a solution of 2-(4-(bis(2-chloroethyl)amino)phenoxy)acetic acid (33 mg, 0.11 mmol, 1.1 equiv), HATU (42 mg, 0.11 mmol, 1.1 equiv) and DIPEA (117 mg, 0.9 mmol, 9.0 equiv) in DMF (2 mL). The solution was stirred at RT for 3 h and concentrated in vacuo. The mixture was then purified using reverse phase prep HPLC to afford 2,2,2-trifluoroacetic acid compound with 3-(2-(4-(bis(2-chloroethyl)amino)phenoxy)-N-(3-(4-(5-(4-methylpiperazin-1-yl)-1H,3'H-[2,5'-bibenzo[d]imidazol]-2'-yl)phenoxy)propyl)acetamido)propanoic acid (3:1) (CS0868). MS (M+) 852.9.

Compound CS0858

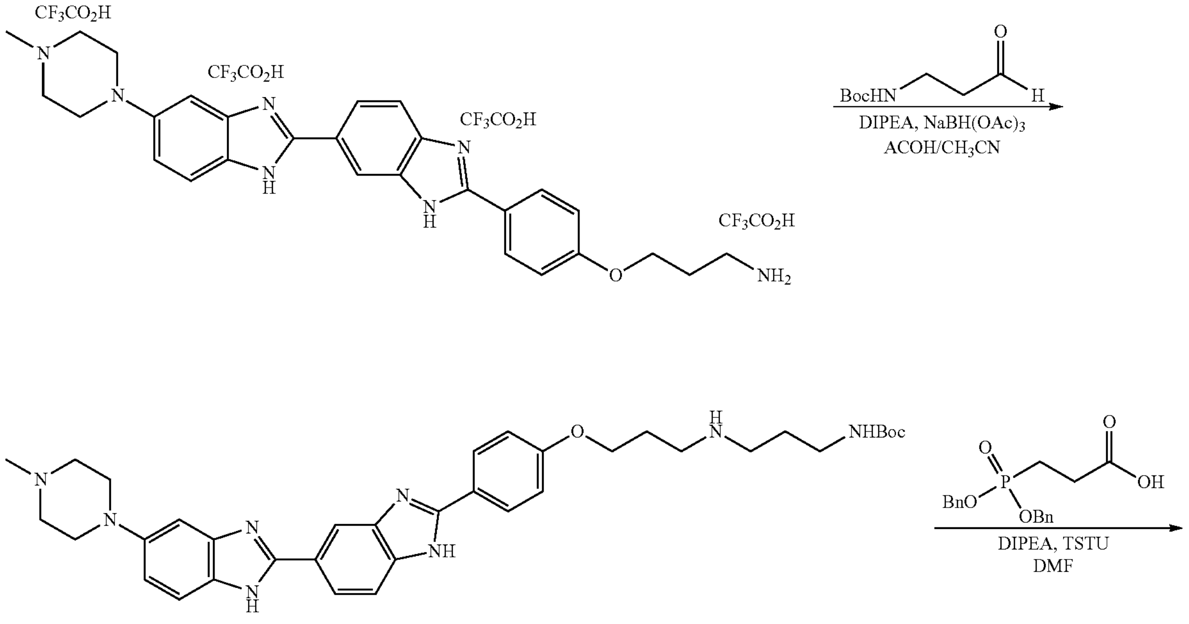

-continued
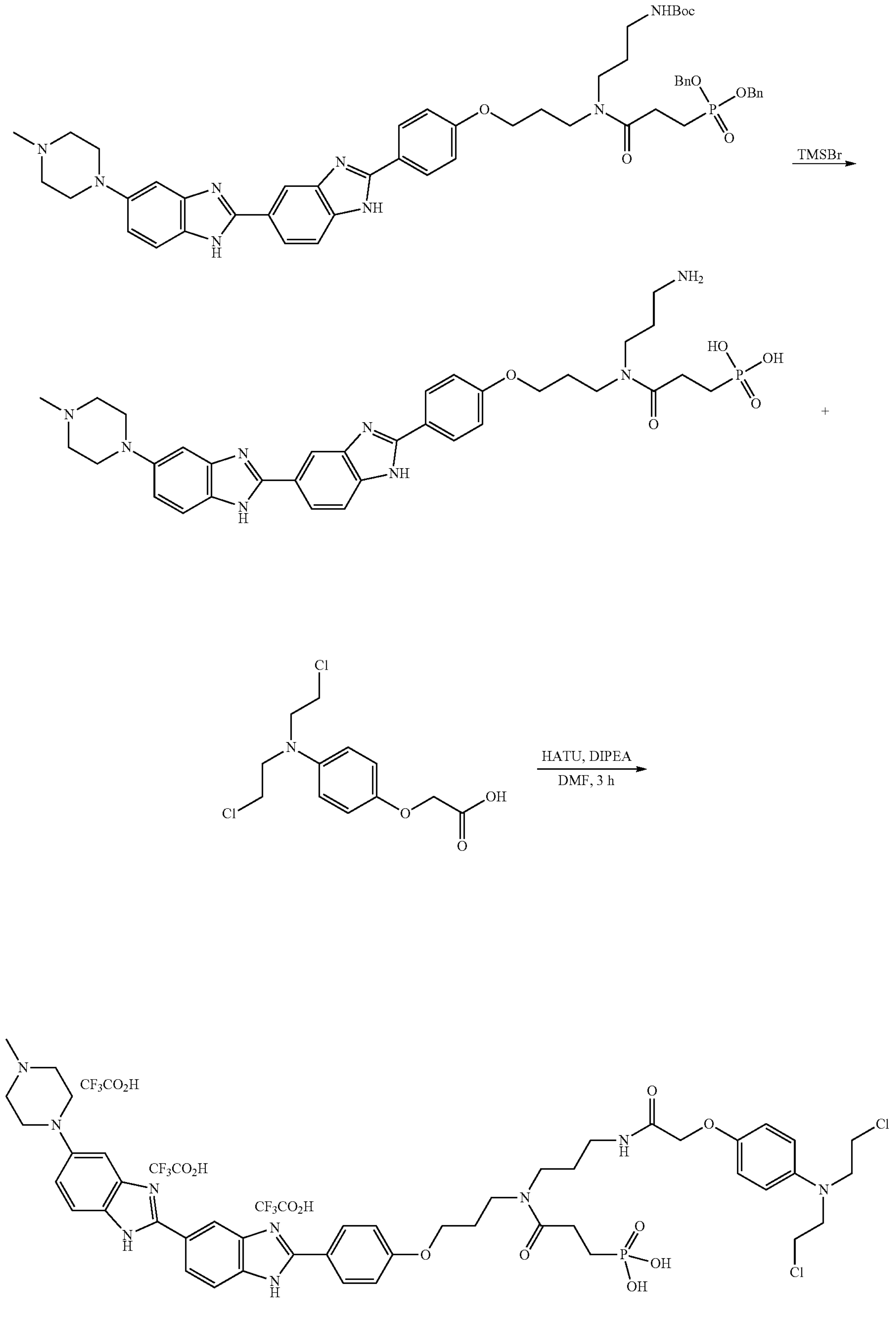

Step 1: tert-Butyl (3-oxopropyl)carbamate (17 mg, 0.1 mmol, 1.0 equiv) was mixed with $NaBH(OAc)_3$ (53 mg, 0.25 mmol, 2.5 equiv) and AcOH (240 μL, 4.0 mmol, 40 equiv) in ACN (2 mL) and stirred for 30 min before a solution of 3-(4-(5-(4-methylpiperazin-1-yl)-1H,3'H-[2,5'-bibenzo[d]imidazol]-2'-yl)phen-oxy)propan-1-amine was added (48 mg, 0.1 mmol, 1.0 equiv). The reaction was stirred at RT for 24 h and purified via reverse phase prep HPLC to afford the intermediate tert-butyl (3-(3-(bis(benzyloxy)phosphoryl)-N-(3-(4-(5-(4-methylpiperazin-1-yl)-1H,1'H-[2,5'-bibenzo[d]imidazol]-2'-yl)phenoxy)propyl)propanamido) propyl)carbamate.

Step 2: 3-(bis(benzyloxy)phosphoryl)propanoic acid (50 mg, 0.15 mmol, 1.5 equiv) was mixed with TSTU (45 mg, 0.15 mmol, 1.5 equiv) and DIPEA (50 μL, 0.3 mmol, 3.0 equiv) in DMF (2 mL). To this solution, tert-butyl (3-(3-(bis(benzyloxy)phosphoryl)-N-(3-(4-(5-(4-methyl-piperazin-1-yl)-1H,1'H-[2,5'-bibenzo-[d]imidazol]-2'-yl)phenoxy)propyl)propanamido)propyl)-c-arbamate (64 mg, 0.1 mmol, 1.0 equiv) was added, and the solution was stirred at RT for 3 h and purified via reverse phase prep HPLC to afford the intermediate tert-butyl (3-(3-(bis(benzyloxy)phosphoryl)-N-(3-(4-(5-(4-methylpiperazin-1-yl)-1H,1'H-[2,5'-bibenzo[d]imidazo]-2'-yl)phenoxy)propyl)propanamido) propyl)carbamate.

Step 3: tert-Butyl (3-(3-(bis(benzyloxy)phosphoryl)-N-(3-(4-(5-(4-methylpiperazin-1-yl)-1H,1'H-[2,5'-bibenzo[d] imi-dazo]-2'-yl)phenoxy)propyl)propanamido)propyl)carbamate (95 mg, 0.1 mmol, 1.0 equiv) was dissolved in TMSBr (2 mL) and stirred at RT for 2 h. LC-MS indicated full conversion to the desired product. The reaction was concentrated and purified via reverse phase HPLC purification to afford trifluoroacetate salt of (3-((3-aminopropyl)(3-(4-(5-(4-methylpiperazin-1-yl)-1H,1'H-[2,5'-bibenzo-[d] imidazol]-2'-yl)phenoxy)propyl)amino)-3-oxopro-pyl) phosphonic acid.

Step 4: Trifluoroacetate salt of (3-((3-aminopropyl)(3-(4-(5-(4-methylpiperazin-1-yl)-1H,1'H-[2,5'-bibenzo[d]imidazol]-2'-yl)phenoxy)propyl)amino)-3-oxopro-pyl)phosphonic acid (113 mg, 0.1 mmol, 1.0 equiv) was added to a solution of 2-(4-(bis(2-chloroethyl)amino)phenoxy)acetic acid (33 mg, 0.11 mmol, 1.1 equiv), HATU (42 mg, 0.11 mmol, 1.1 equiv) and DIPEA (117 mg, 0.9 mmol, 9.0 equiv) in DMF (2 mL). The solution was stirred at RT for 3 h and concentrated in vacuo. The mixture was then purified using reverse phase prep HPLC to afford the desired trifluoroacetate salt of (3-((3-(2-(4-(bis(2-chloroethyl)amino)phenoxy) acetamido)propyl)(3-(4-(5-(4-methylpiperazin-1-yl)-1H, 1'H-[2,5'-bibenzo-[d]imidazol]-2'-yl)phenoxy)propyl) amino)-3-oxopropyl)phosphonic acid (CS0858). MS (M+) 948.3.

Compound CS0985

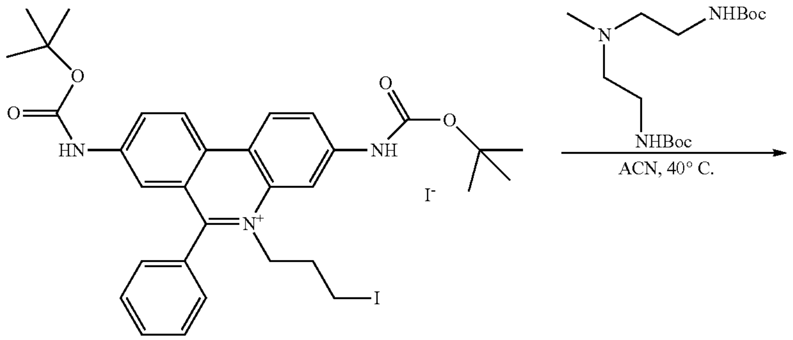

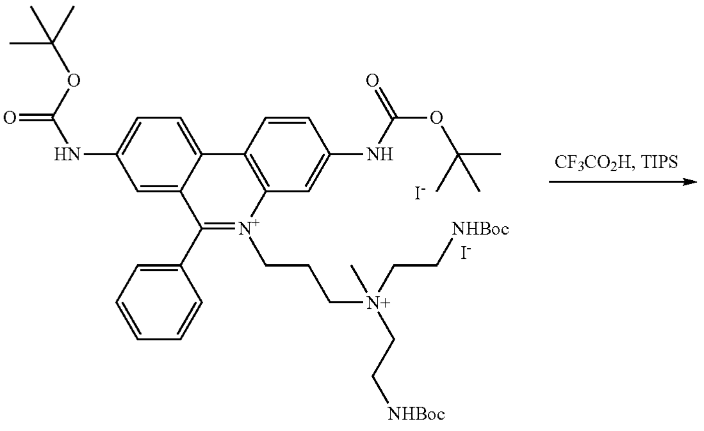

-continued

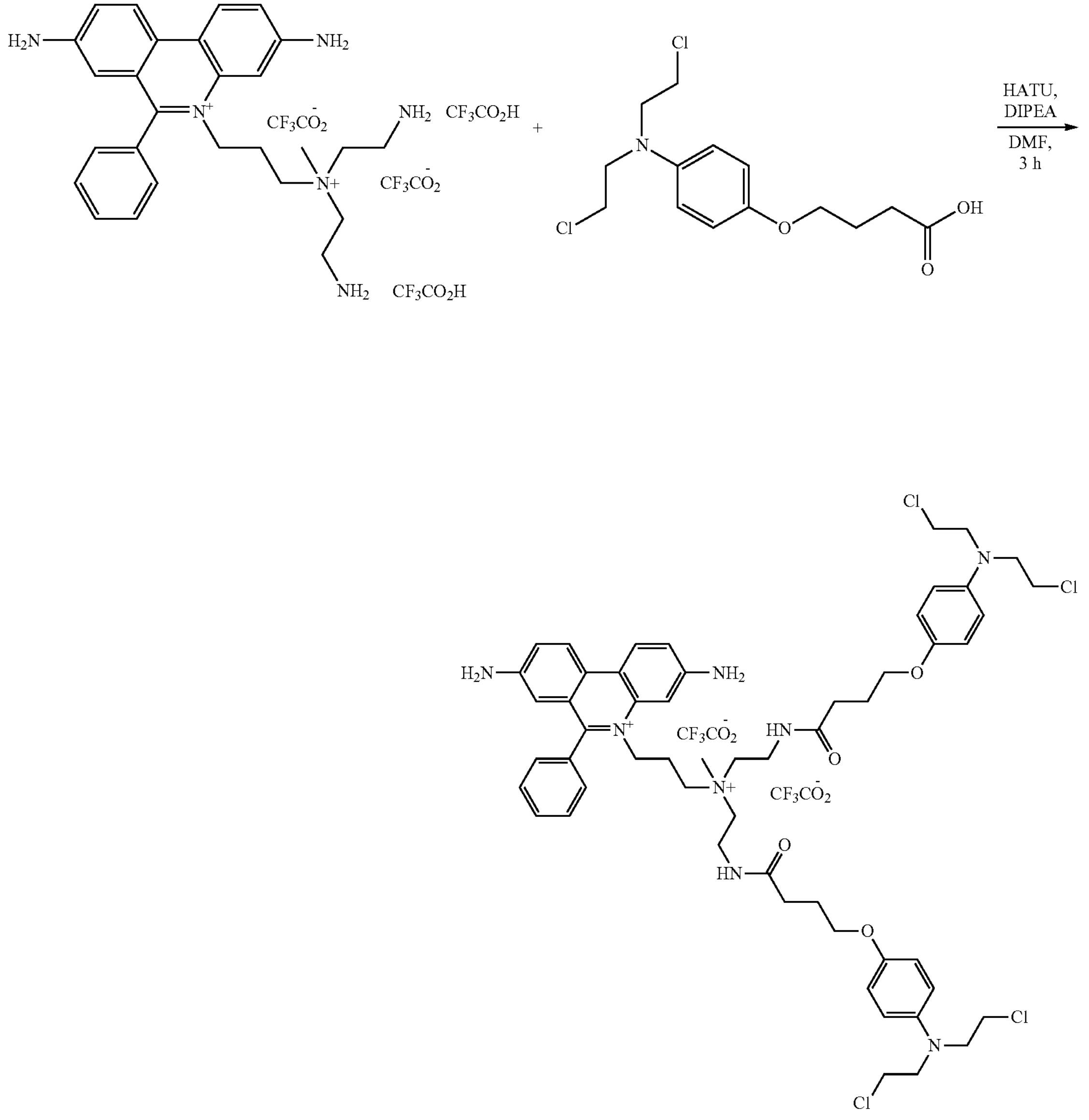

CS0985

Step 1: 3,8-Bis((tert-butoxycarbonyl)amino)-5-(3-iodopropyl)-6-phenylphenanthridin-5-ium iodide (18 mg, 23 μmol, 1.0 equiv) was mixed with di-tert-butyl ((methylazanediyl)bis(ethane-2,1-diyl))dicarbamate (73 mg, 230 μmol, 10 equiv) in $CH_3CN$ (2 mL) under 40° C. for 6 d. The reaction was concentrated and purified by reverse prep HPLC to afford 5-(3-(bis(2-((tert-butoxycarbonyl)amino)ethyl)(methyl)ammonio)propyl)-3,8-bis((tert-butoxycarbonyl)amino)-6-phenylphenanthridin-5-ium iodide.

Step 2: 5-(3-(Bis(2-((tert-butoxycarbonyl)amino)ethyl)(methyl)ammonio)propyl)-3,8-bis((tert-butoxy-car-bonyl)amino)-6-phenylphenanthridin-5-ium iodide (25 mg, 23 μmol, 1.0 equiv) was dissolved in $CF_3CO_2H$/TIPS (2 mL/0.2 mL) and stirred at RT for 1 h. The reaction was concentrated and purified by reverse prep HPLC to afford the trifluoroacetate salts of 3,8-diamino-5-(3-(bis(2-aminoethyl)-(methyl)ammonio)propyl)-6-phenylphenanthridin-5-ium.

Step 3: Trifluoroacetate salt of 3,8-diamino-5-(3-(bis(2-aminoethyl)-(methyl)ammonio)propyl)-6-phenylphenanthridin-5-ium (44 mg, 0.1 mmol, 1.0 equiv) was added to a solution of 4-(4-(bis(2-chloroethyl)amino)phenoxy)butanoic acid (76 mg, 0.24 mmol, 2.4 equiv), HATU (91 mg, 0.24 mmol, 2.4 equiv) and DIPEA (117 mg, 0.9 mmol, 9.0 equiv) in DMF (2 mL). The solution was stirred at RT for 3 h and then purified using reverse phase prep HPLC to afford the desired trifluoroacetate salt of 3,8-diamino-5-(3-(bis(2-(4-(4-(bis(2-chloroethyl)amino)phenoxy)butanamido)ethyl)(methyl)ammonio)propyl)-6-phenylphenanthridin-5-ium (CS0985). MS (M+)=524.3.

Compound CS1065

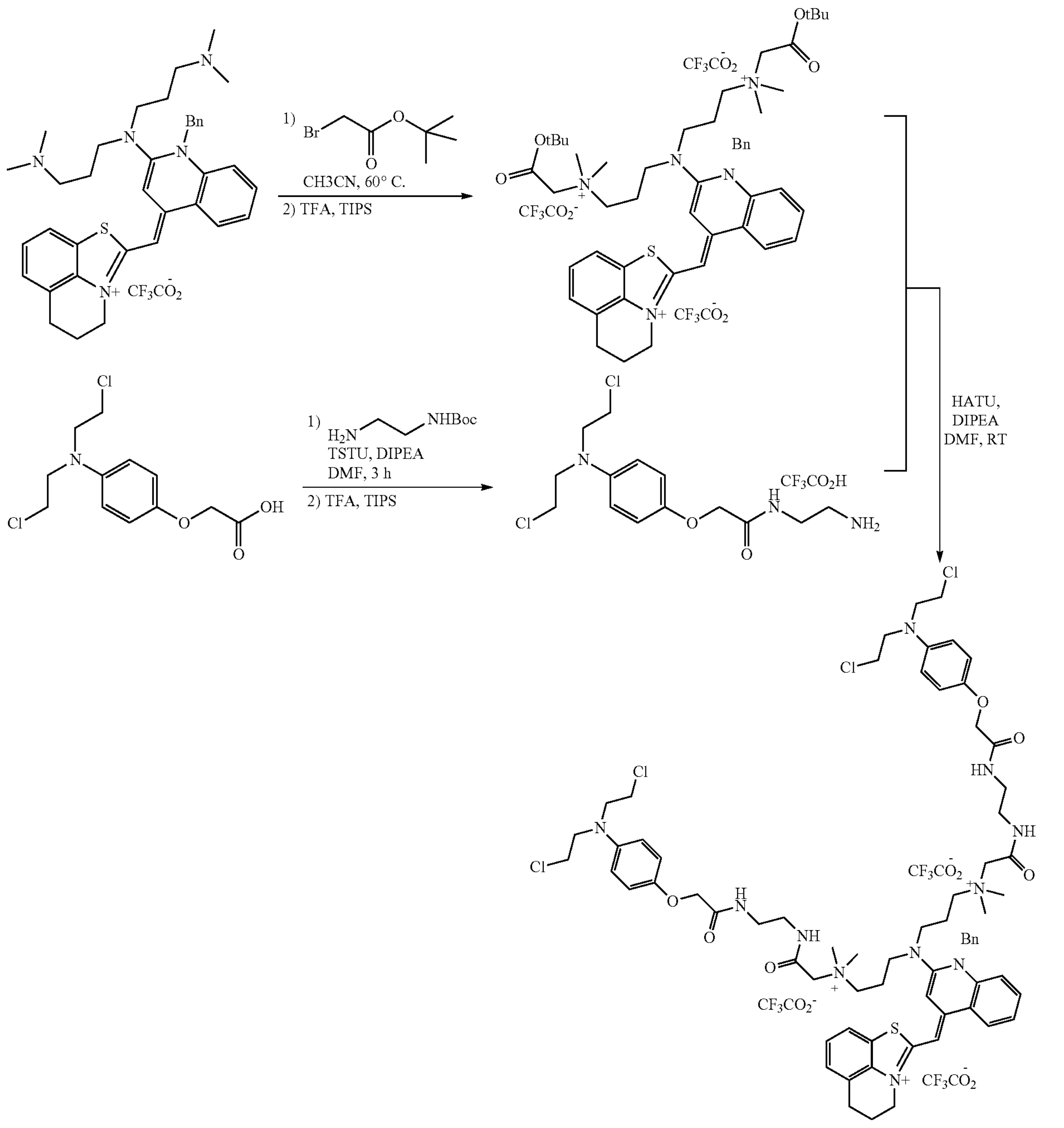

CS1065

Step 1. (E)-2-((1-benzyl-2-(bis(3-(dimethylamino)propyl)amino)quinolin-4(1H)-ylidene)methyl)-5,6-dihydro-4H-thiazolo[5,4,3-ij]quinolin-3-ium trifluoroacetate (70 mg, 0.1 mmol, 1.0 equiv) was added to a solution of tert-butyl bromoacetate (390 mg, 2 mmol, 20 equiv) in $CH_3CN$ (5 mL), and the reaction was heated to 50° C. for 3 d. The reaction was then concentration and used directly in the next step without further purification.

The intermediate mentioned above (E)-2-((1-benzyl-2-(bis(3-((2-(tert-butoxy)-2-oxoethyl)dimethylam-monio)propyl)amino)quinolin-4(1H)-ylidene)methyl)-5,6-dihydro-4H-thiazolo[5,4,3-ij]quinolin-3-ium trifluoroacetate salt (11.6 mg, 0.01 mmol, 1.0 equiv) was dissolved in TFA/TIPS (2/0.2 mL) and stirred at RT for 2 h. The reaction was concentrated and purified by reverse phase prep HPLC to afford (E)-2-((1-benzyl-2-(bis(3-((carboxymethyl)dimethyl-ammonio)propyl)amino)quinolin-4(1H)-ylidene)methyl)-5,6-dihydro-4H-thiazolo[5,4,3-ij]quinolin-3-ium trifluoroacetate salt.

Step 2: 2-(4-(bis(2-chloroethyl)amino)phenoxy)acetic acid (29 mg, 0.1 mmol, 1.0 equiv) was added to a solution of tert-butyl (2-aminoethyl)carbamate (160 mg, 0.1 mmol, 1.0 equiv), TSTU (33 mg, 0.11 mmol, 1.1 equiv) and DIPEA (26 mg, 0.2 mmol, 2.0 equiv) in $CH_3CN$ (2 mL). The reaction was concentration in vacuo and purified via normal phase silica gel (Heptane/EtOAc) to afford the intermediate tert-butyl (2-(2-(4-(bis(2-chloroethyl)amino)phenoxy)acetamido)ethyl)carbamate, which was subsequently dissolved in TFA/TIPS (2/0.2 mL). The reaction was stirred for 30 min to ensure completion and concentration in vacuo afforded the N-(2-aminoethyl)-2-(4-(bis(2-chloro-ethyl)amino)phenoxy)acetamide, trifluoroacetate salt product which was used in the next step without further purification.

Step 3: N-(2-aminoethyl)-2-(4-(bis(2-chloro-ethyl)amino)phenoxy)acetamide, trifluoroacetate salt (8.8 mg, 0.02 mmol, 2.0 equiv) was added to a solution of (E)-2-((1-benzyl-2-(bis(3-((carboxymethyl)dimethylammonio)propyl)amino)quinolin-4(1H)-ylidene)methyl)-5,6-dihydro-4H-thiazolo[5,4,3-ij]quinolin-3-ium trifluoroacetate salt (10.5 mg, 0.1 mmol, 1.0 equiv), HATU (84 mg, 0.22 mmol, 2.2 equiv) and DIPEA (240 mg, 1.8 mmol, 18.0 equiv) in DMF (2 mL). The solution was stirred at RT for 3 h and concentrated in vacuo. The mixture was then purified using reverse phase prep HPLC to afford (E)-2-((1-benzyl-2-(bis(3-((2-((2-(2-(4-(bis(2-chloroethyl)amino)phenoxy)acetamido)ethyl)amino)-2-oxoethyl)dimethylammonio)propyl)amino)quinolin-4(1H)-ylidene)methyl)-5,6-dihydro-4H-thiazolo[5,4,3-ij]quinolin-3-ium 2,2,2-trifluoroacetate (CS1065). MS (M+)=447.5.

Example 3

Viability PCR Experiment with *Listeria innocua*

Figure 2:
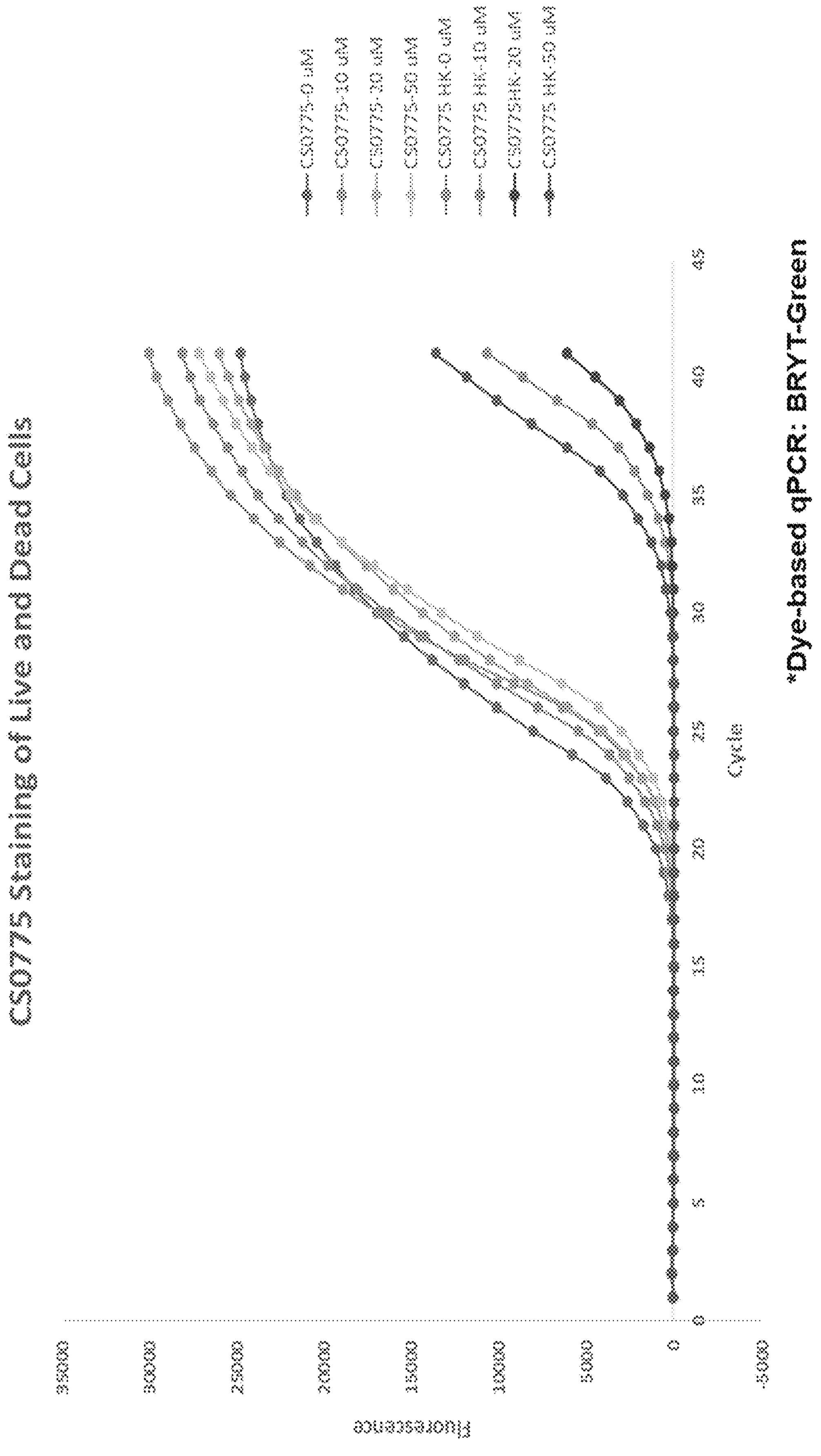
FIG. 2 shows data from vPCR reactions conducted in live and dead cells with several concentrations of compound CS0775.

Turbid overnight cultures of *Listeria innocua* were subcultured into Terrific Broth, grown to early/mid-exponential phase, and concentrated to OD ~1.0 (~1×10^8 CFU/mL). 200 uL of live or dead (heat-killed for 95° C. for 15 minutes, HK) *Listeria innocua* cells were incubated with listed concentrations of compound CS0775 at 37° C. for 90 minutes. Inactivation buffer was added to reaction tubes, and reactions incubated at room temperature for 15 minutes. Nucleic acid was purified using the Maxwell automated purification workflow and a dye-based qPCR analysis using primers specific for *Listeria innocua* was performed. Results are shown in FIG. 2. ΔCt is defined as the qPCR signal threshold difference between dead and live cells. Viable and non-viable cells are clearly distinguished using the described viability PCR workflow.

Example 4

Solvent Effect on Permeation in Non-Viable Cells

Figure 3:
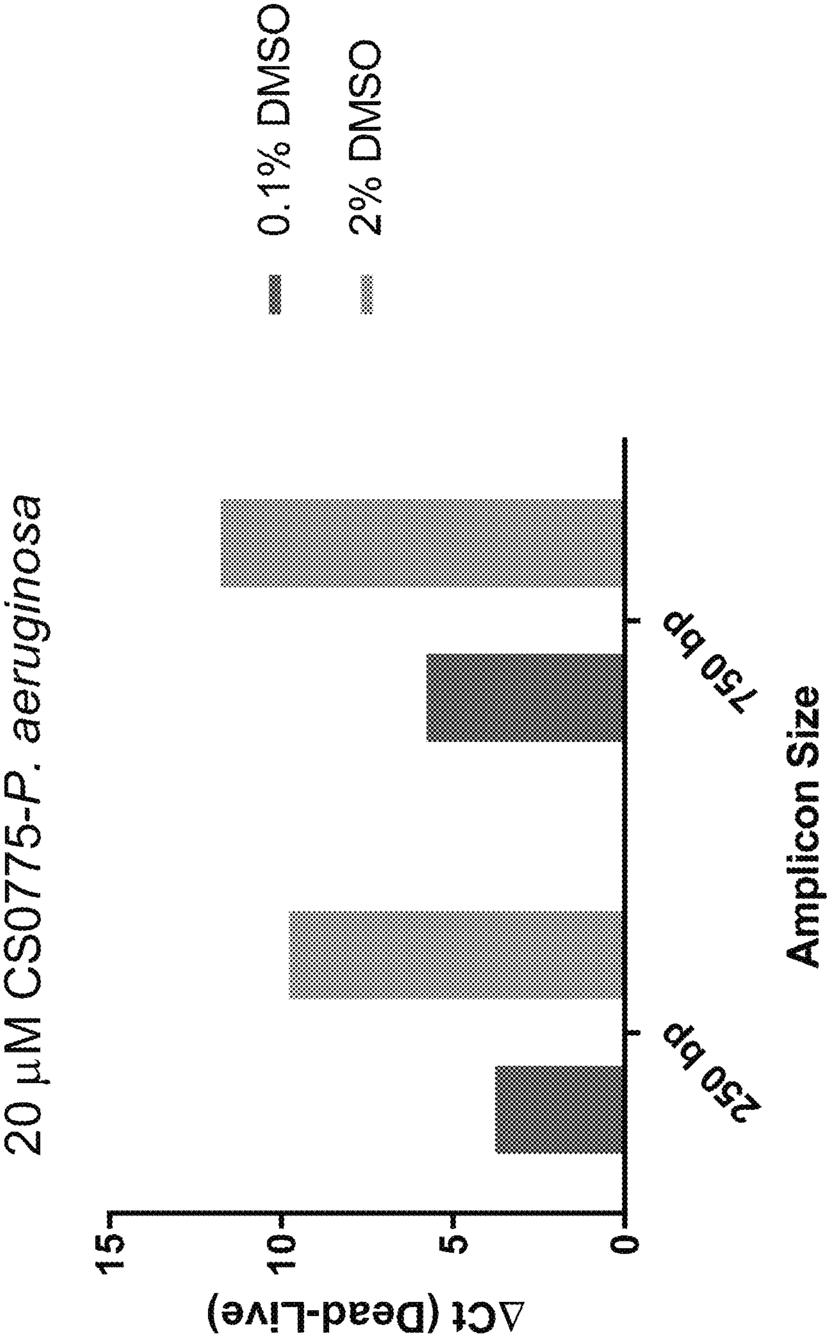
FIG. 3 shows data from vPCR reactions performed in a representative Gram-negative bacterium in the presence of compound CS0775 in varying concentrations of DMSO and two amplicon sizes.

Turbid cultures of *Pseudomonas aeruginosa* were subcultured into LB Broth, grown to early/mid-exponential phase, and concentrated to OD ~1.0 (~1×10^8 CFU/mL). 200 μL of live or dead (heat-killed for 95° C. for 15 minutes, HK) *Pseudomonas aeruginosa* cells were incubated with 20 uM CS0775 at 37° C. for 90 minutes. Inactivation buffer was added to reaction tubes, and reactions incubated at room temperature for 15 minutes. Nucleic acid was purified using the Maxwell automated purification workflow and a dye-based qPCR analysis using primer sets specific for *Pseudomonas aeruginosa* was performed. Results are shown in FIG. 3. PCR amplicon size notated on horizontal axis. ΔCt is defined as the qPCR signal threshold difference between dead and live cells. Increased concentration of DMSO in the final reaction increases the DNA modification efficiency and subsequent differentiation of non-viable cells from viable cells.

Example 5

Amplicon Length Analysis

Figure 4:
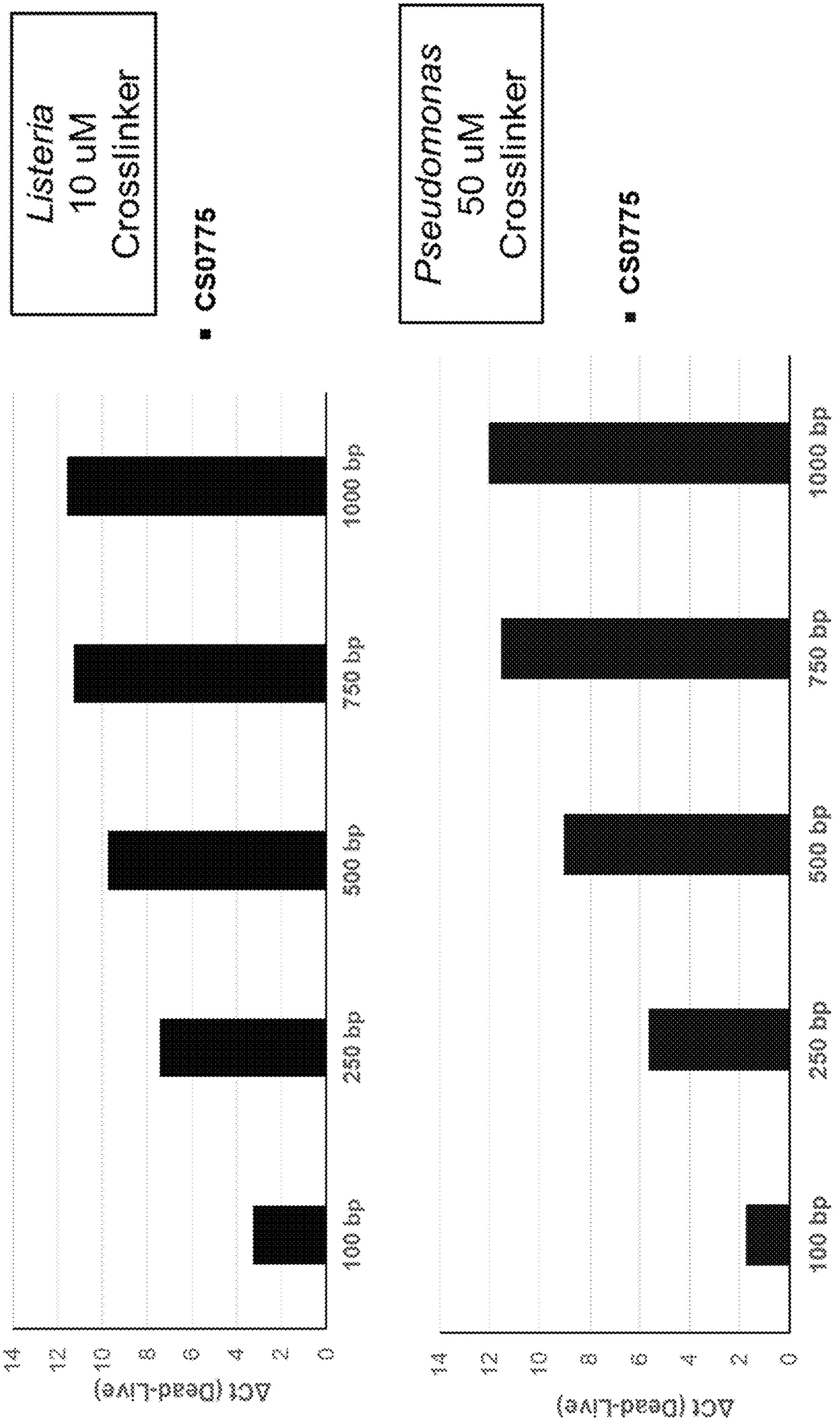
FIG. 4 shows data from vPCR reactions in representative bacterial strains in the presence of compound CS0775 using primers optimized for various amplicon sizes.

Turbid cultures of *Pseudomonas aeruginosa* and *Listeria innocua* were subcultured into LB Broth or Terrific Broth, respectively, grown to early/mid-exponential phase, and concentrated to OD ~1.0 (~1×10^8 CFU/mL). 200 μL of live or dead (heat-killed for 95° C. for 15 minutes, HK) bacterial cells were incubated with 10 uM (*Listeria*) or 50 uM (*Pseudomonas*) CS0775 at 37° C. for 90 minutes. Inactivation buffer was added to reaction tubes, and reactions incubated at room temperature for 15 minutes. Nucleic acid was purified using the Maxwell automated purification workflow and a dye-based qPCR analysis using primers sets specific for *Pseudomonas aeruginosa* or *Listeria innocua* was performed. Results are shown in FIG. 4. PCR amplicon size notated on horizontal axis. Live-dead differentiation (ΔCt) increases with amplicon length.

Example 6

Effects of Compound Concentration

Figure 5:
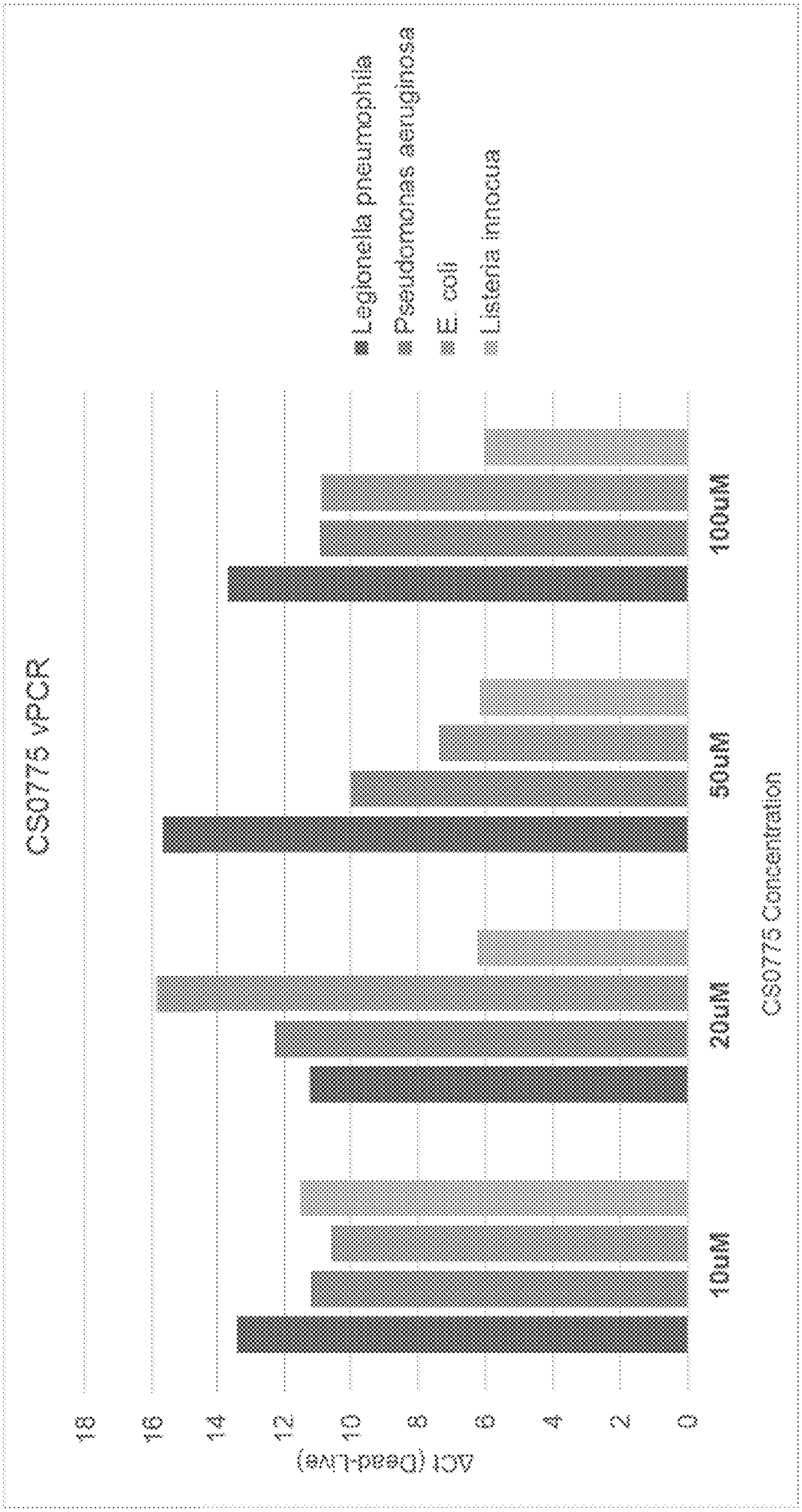
FIG. 5 shows data from vPCR reactions in representative bacterial strains in the presence of varying concentrations of compound CS0775.

Turbid cultures of *Pseudomonas aeruginosa, Escherichia coli, Legionella pneumophila*, and *Listeria innocua* were subcultured into LB Broth (*E. coli, P. aeruginosa*) Terrific Broth (*L. innocua*), or *Legionella* broth (*L. pneumophila*), grown to early/mid-exponential phase, and concentrated to OD ~1.0 (~1×10^8 CFU/mL). 200 μL of live or dead (heat-killed for 95° C. for 15 minutes, HK) bacterial cells were incubated with the indicated concentration of CS0775 at 37° C. for 90 minutes. Inactivation buffer was added to reaction tubes, and reactions incubated at room temperature for 15 minutes. Nucleic acid was purified using the Maxwell automated purification workflow and a dye-based qPCR analysis using primers sets specific for the listed bacterial species was performed. Results are shown in FIG. 5. Optimal concentration of compound varies between Gram-negative and Gram-positive bacteria.

Example 7

Viability PCR Assays Using Various Compounds

Figure 6:
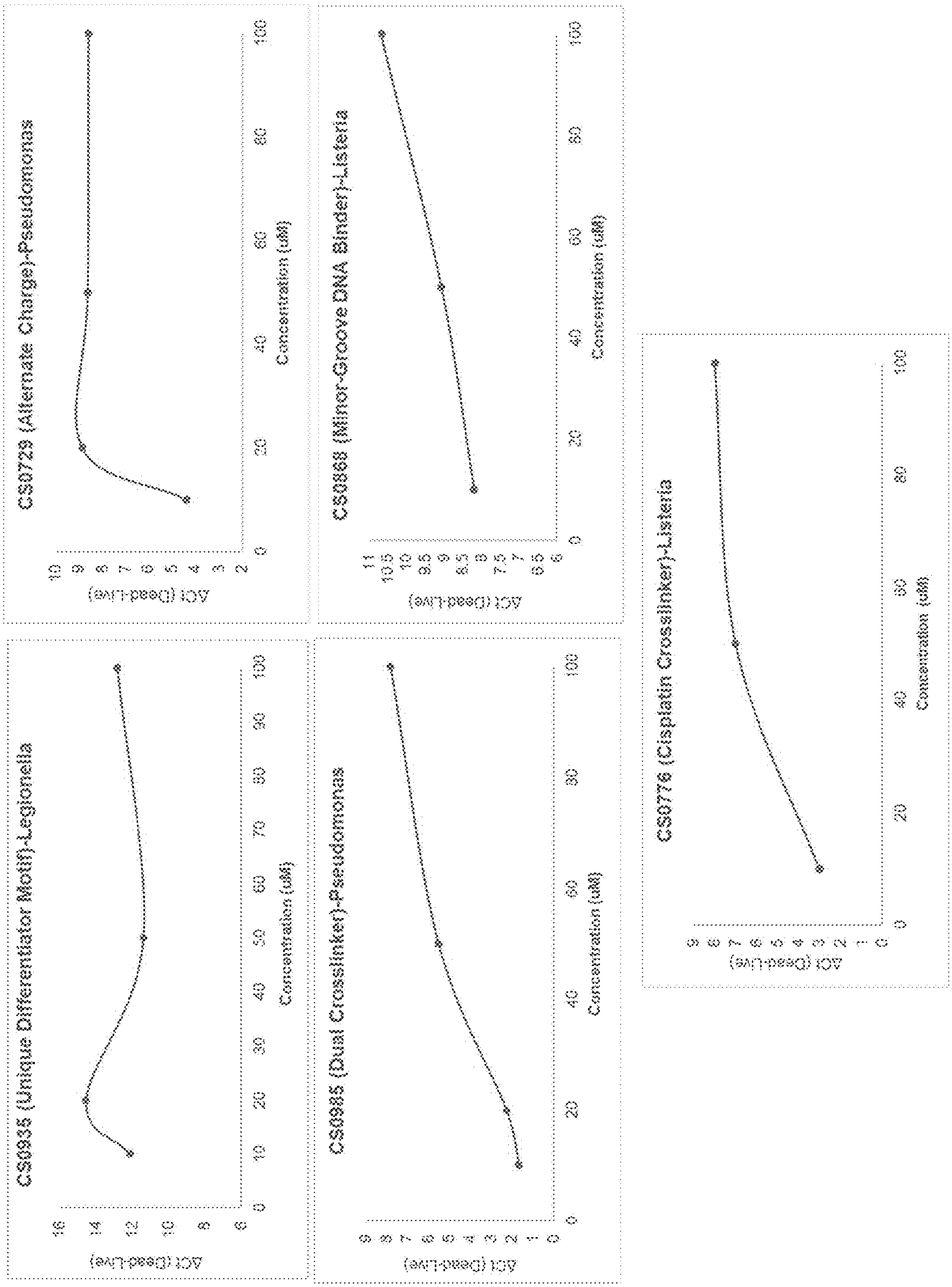
FIG. 6 shows data from vPCR reactions in representative bacterial strains in the presence of several compounds of the disclosure at varying concentrations.

Turbid cultures of *Pseudomonas aeruginosa, Legionella pneumophila*, and *Listeria innocua* were subcultured into LB Broth (*P. aeruginosa*), Terrific Broth (*L. innocua*), or *Legionella* broth (*L. pneumophila*), grown to early/mid-exponential phase, and concentrated to OD ~1.0 (~1×10^8 CFU/mL). 200 μL of live or dead (heat-killed for 95° C. for 15 minutes, HK) bacterial cells were incubated with the indicated concentration of the indicated compound at 37° C. for 90 minutes. Inactivation buffer was added to reaction tubes, and reactions incubated at room temperature for 15 minutes. Nucleic acid was purified using the Maxwell automated purification workflow and a dye-based qPCR analysis using primers sets specific for the listed bacterial species was performed. Results are shown in FIG. 6. Different classes of compounds can effectively discriminate between viable and non-viable cells when used as part of the viability PCR procedure.

Example 8

Assay Sensitivity

Figure 7:
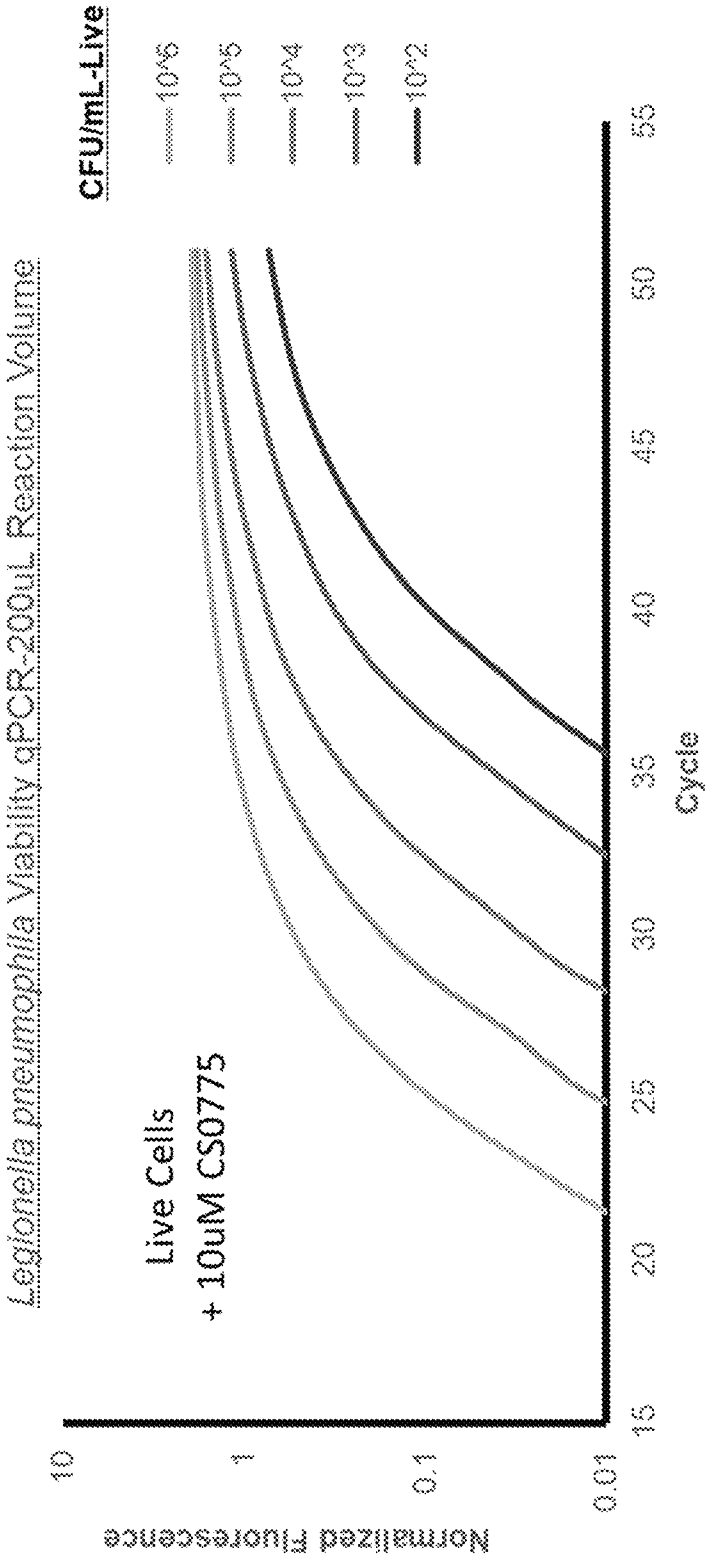
FIG. 7 shows data from vPCR reactions in samples containing various cell concentrations in the presence of compound CS0775.

Turbid cultures of *Legionella pneumophila* were subcultured into *Legionella* Broth, grown to early/mid-exponential phase, and concentrated to OD ~1.0 (~1x10^8 CFU/mL). Serial dilutions were performed and 200 μL of the indicated concentration of live *Legionella pneumophila* cells were incubated with 10 uM CS0775 at 37° C. for 90 minutes. Inactivation buffer was added to reaction tubes, and reactions incubated at room temperature for 15 minutes. Nucleic acid was purified using the Maxwell automated purification workflow and a probe-based qPCR analysis using a primer and probe set specific for *Legionella pneumophila* was performed. Results are shown in FIG. 7. The assay can detect bacteria at concentrations as low as ~$10^2$ CFU/mL.

Example 9

Assays in Samples with Live and Dead Cells

Figure 8:
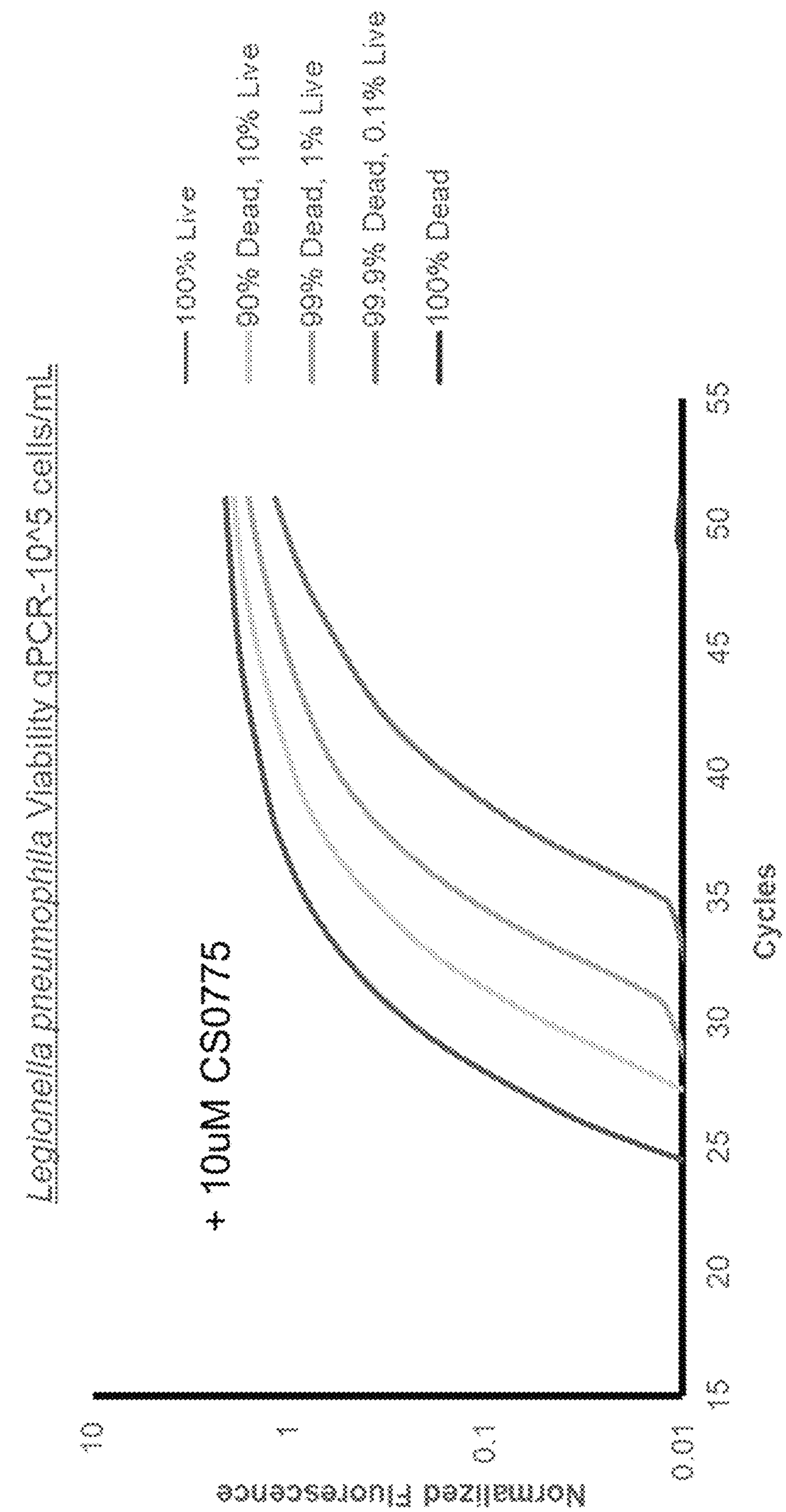
FIG. 8 shows data from vPCR reactions in samples with various proportional combinations of live and dead cells in the presence of compound CS0775.

Turbid cultures of *Legionella pneumophila* were subcultured into *Legionella* broth, grown to early/mid-exponential phase, and concentrated to OD ~1.0 (~1x10^8 CFU/mL). Cells were subsequently diluted to 10^5 CFU/mL. The listed proportions of live or dead (heat-killed for 95° C. for 15 minutes, HK) bacterial cells were mixed (total volume: 200 uL) and incubated with 10 uM of CS0775 at 37° C. for 90 minutes. Inactivation buffer was added to reaction tubes, and reactions incubated at room temperature for 15 minutes. Nucleic acid was purified using the Maxwell automated purification workflow and a probe-based qPCR analysis using a primer and probe set specific for *Legionella pneumophila* was performed. Results are shown in FIG. 8. The assay can discriminately detect small proportions of live cells in background of predominantly dead cells.

Example 10

Viability PCR Comparison to Traditional Culture

Turbid cultures of *Legionella pneumophila* were subcultured into *Legionella* Broth, grown to early/mid-exponential phase, and concentrated to OD ~1.0 (~1x10^8 CFU/mL). Serial dilutions were performed, plated on *Legionella* agar to confirm CFU/mL. In parallel, 200 μL of the indicated dilution of live *Legionella pneumophila* cells were incubated with or without 10 uM CS0775 at 37° C. for 90 minutes. Inactivation buffer was added to reaction tubes, and reactions incubated at room temperature for 15 minutes. Nucleic acid was purified using the Maxwell automated purification workflow and a probe-based qPCR analysis using a primer and probe set specific for *Legionella pneumophila* was performed. A standard curve of *Legionella* template DNA was amplified concurrently with the experimental samples to allow for quantification. Results are shown in Table 2. vGU: viable genomic units. The assay produces quantitative data that is comparable to traditional culture-based *Legionella pneumophila* detection techniques.

TABLE 2

| vPCR-Determined Live Cell Numbers | | | |
|---|---|---|---|
| Culture | | | |
| Live Cell | Predicted vGU/ | qPCR | |
| Concentration | PCR Reaction | −Crosslinker | +Crosslinker |
| 5.2 × 10^5 CFU/mL | 2600 | 5181.00 | 2534.00 |
| 5.2 × 10^4 CFU/mL | 260 | 537.00 | 211.10 |

TABLE 2-continued

| vPCR-Determined Live Cell Numbers | | | |
|---|---|---|---|
| Culture | | | |
| Live Cell | Predicted vGU/ | qPCR | |
| Concentration | PCR Reaction | −Crosslinker | +Crosslinker |
| 5.2 × 10^3 CFU/mL | 26 | 46.87 | 17.88 |
| 5.2 × 10^2 CFU/mL | 2.6 | 4.13 | 1.54 |

Example 11

Viability PCR Experiment with Adeno-Associated Virus (AAV)

Figure 9:
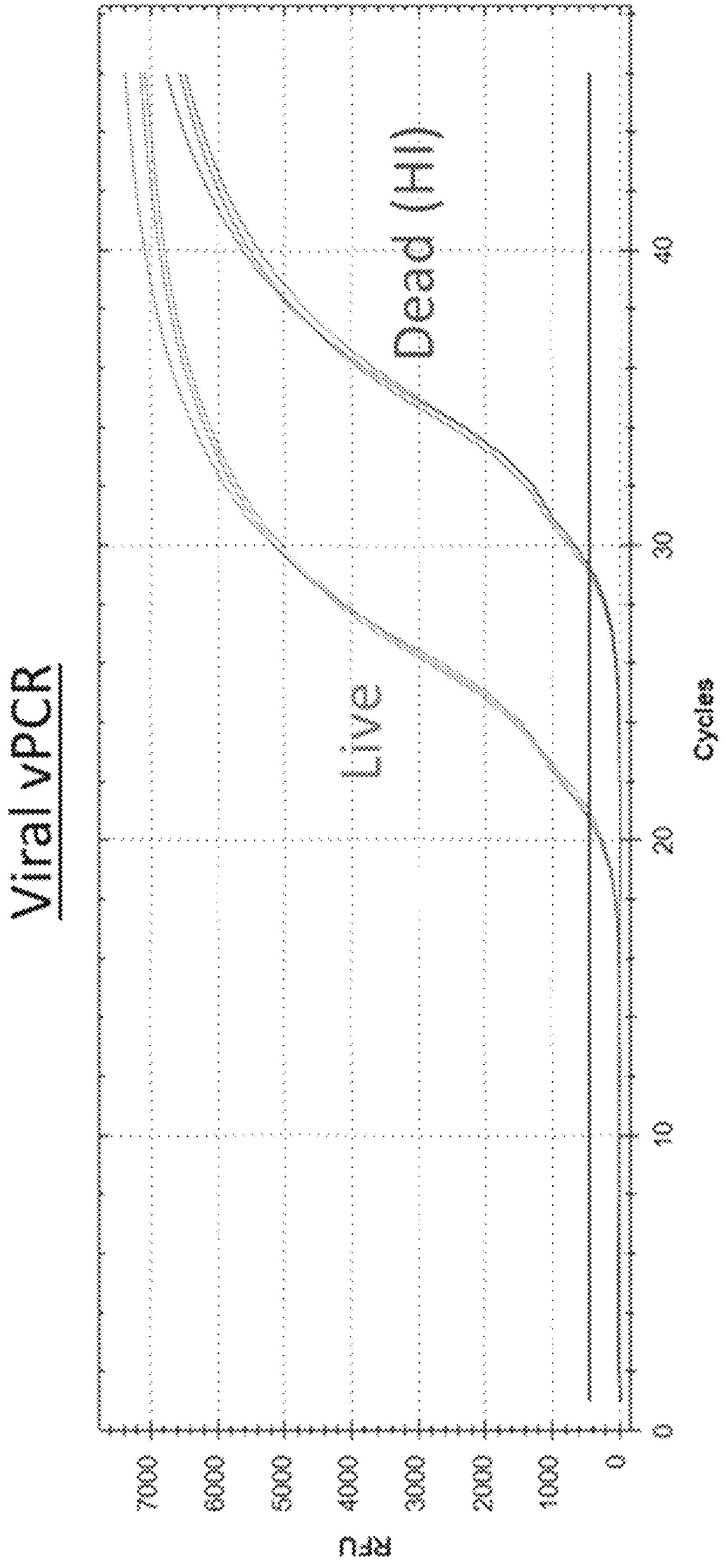
FIG. 9 shows data from vPCR reactions conducted with intact and heat-inactivated virus particles treated with compound CS0775.

AAV9 reference capsids (Vigene Biosciences; Rockville, MD) containing a recombinant CMV-GFP plasmid were diluted to ~10^8/mL in PBS. 200 μL of live (intact) or dead (heat-inactivated at 75° C. for 10 minutes, HI) AAV9 suspensions were incubated with 1 uM CS0775 at 37° C. for 60 minutes. Inactivation buffer was added to reaction tubes, and reactions incubated at room temperature for 15 minutes. Nucleic acid was purified using the Maxwell automated purification workflow, and a dye-based qPCR analysis using primers specific for GFP was performed. Results are shown in FIG. 9. Intact and heat-inactivated viral capsids are clearly distinguished using the described viability PCR workflow.

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, may be made without departing from the spirit and scope thereof.

What is claimed is:

1. A compound or a salt thereof, the compound comprising:

(A) a nucleic acid binding moiety ("NAB moiety") having a structure selected from:

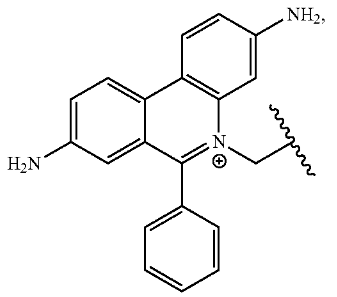

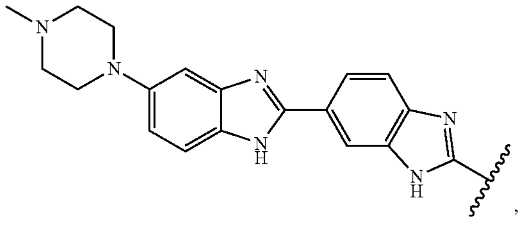

, and

-continued

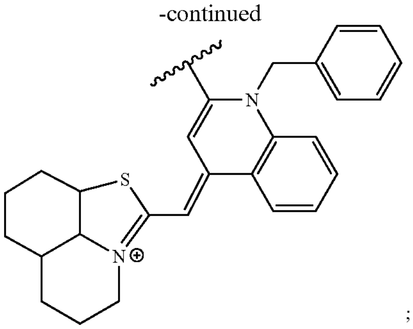

;

(B) a live/dead cell differentiating moiety ("LDCD moiety") having at least one charged moiety; and (C) a nucleic acid modifying moiety ("NAM moiety") having a structure selected from:

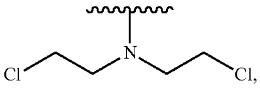

,

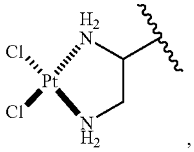

,

-continued

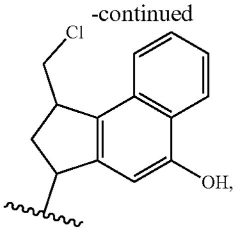

and

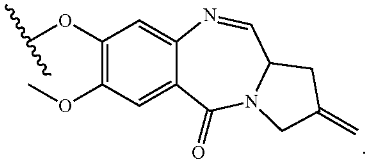

.

2. The compound of claim 1, or a salt thereof, wherein the compound has the structure:

A-B—C wherein A is the NAB moiety, B is the LDCD moiety, C is the nucleic acid modifying moiety.

3. The compound of claim 1, wherein the LDCD moiety comprises at least one quaternary ammonium group.

4. A compound selected from:

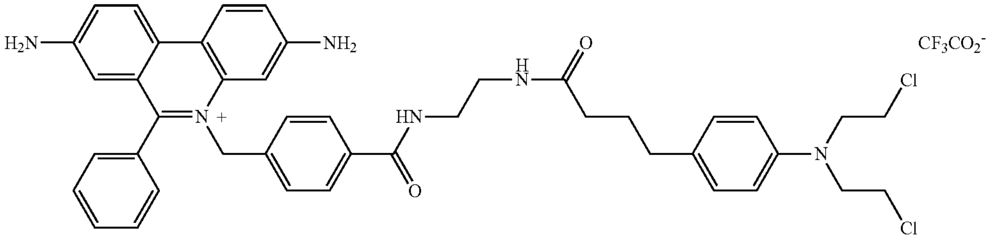

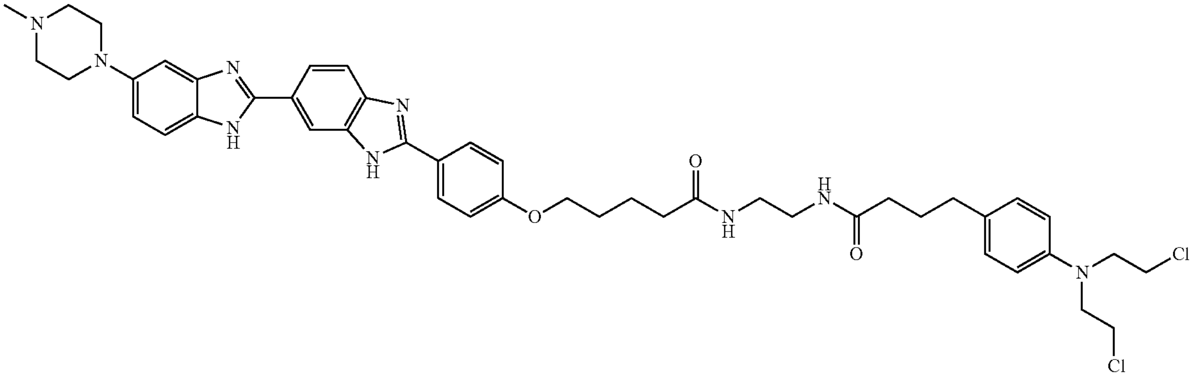

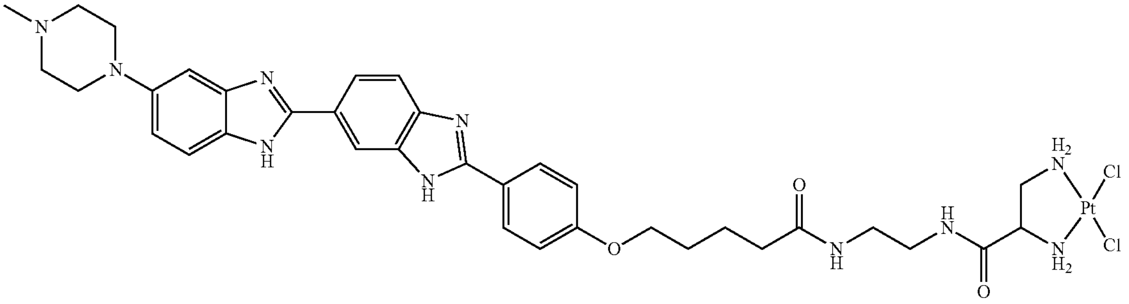

-continued
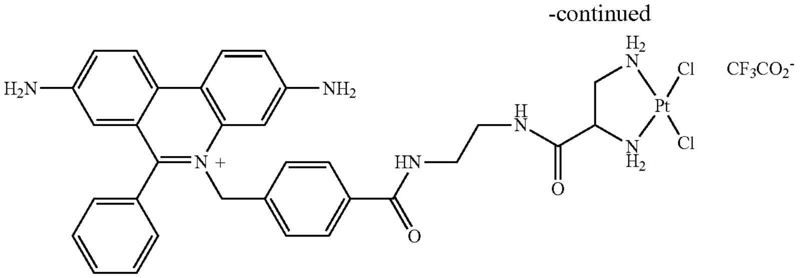
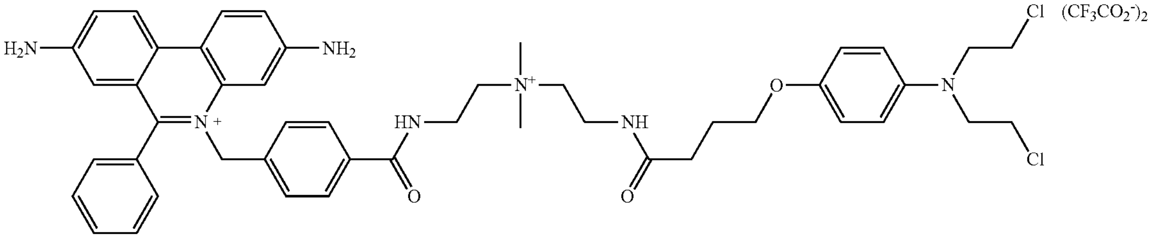
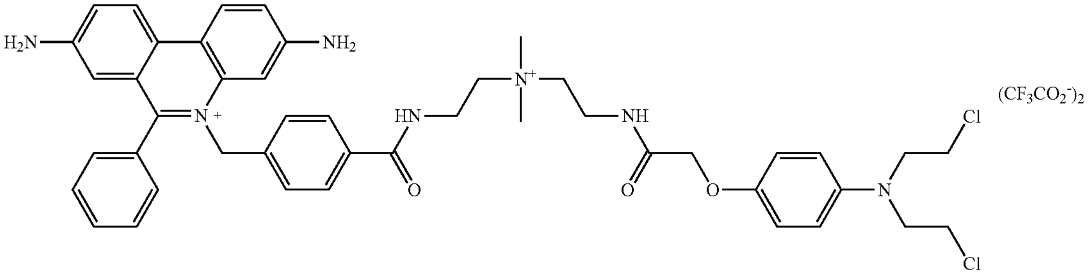
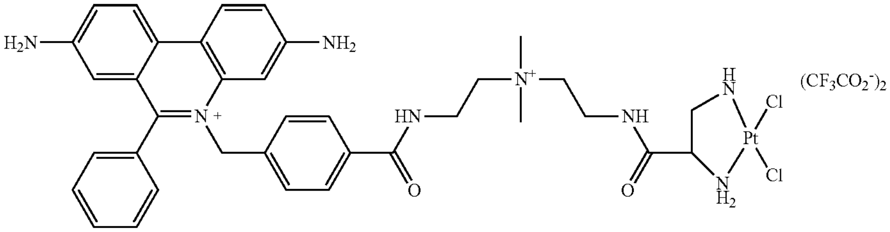
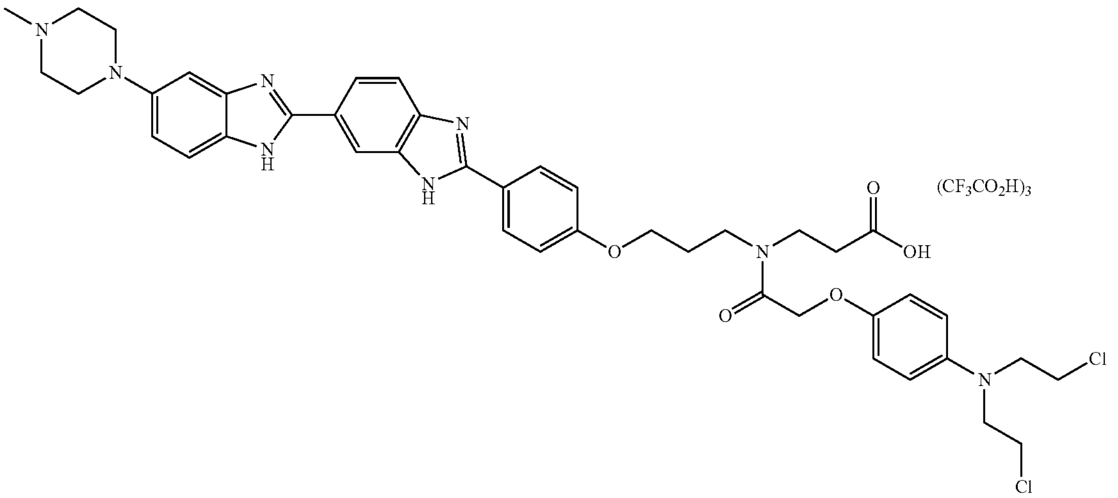

-continued
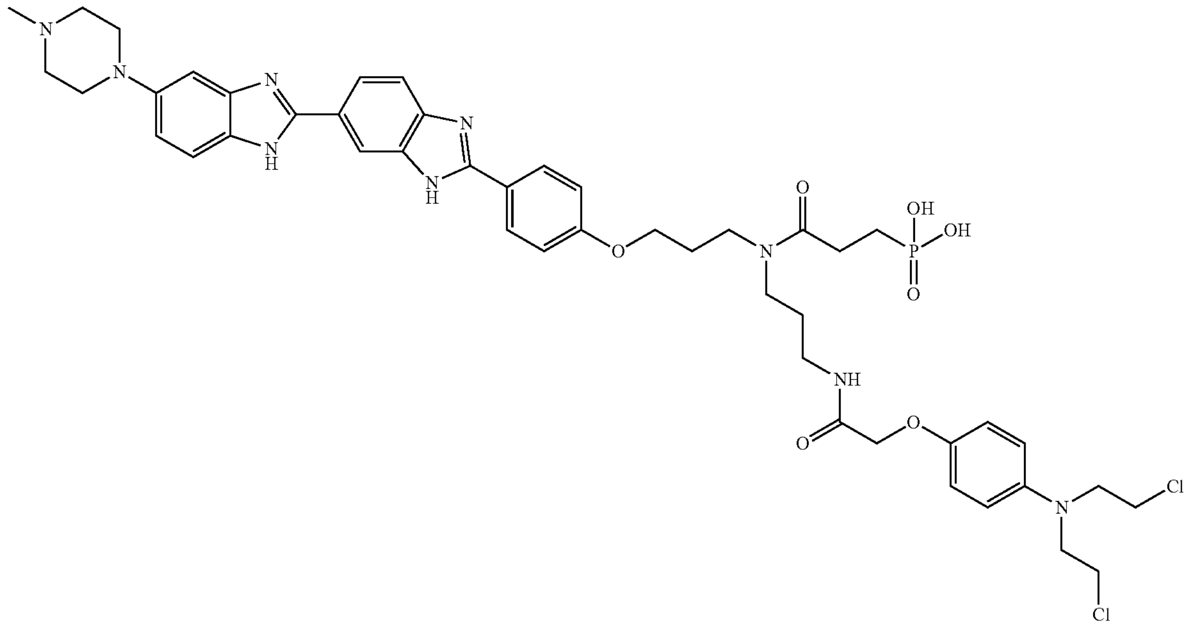
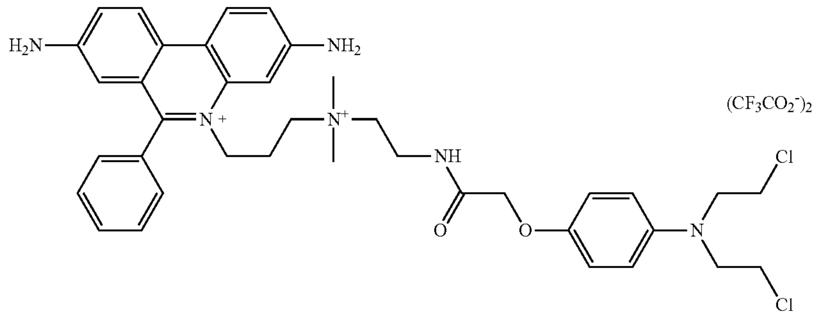
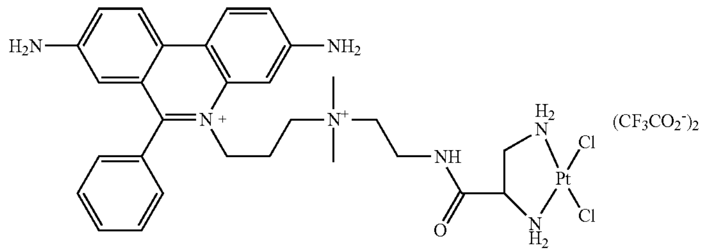
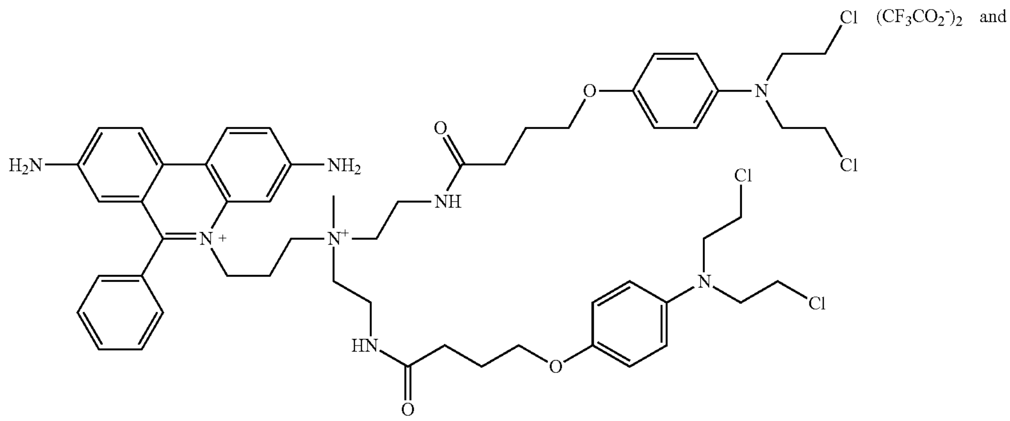
and

-continued

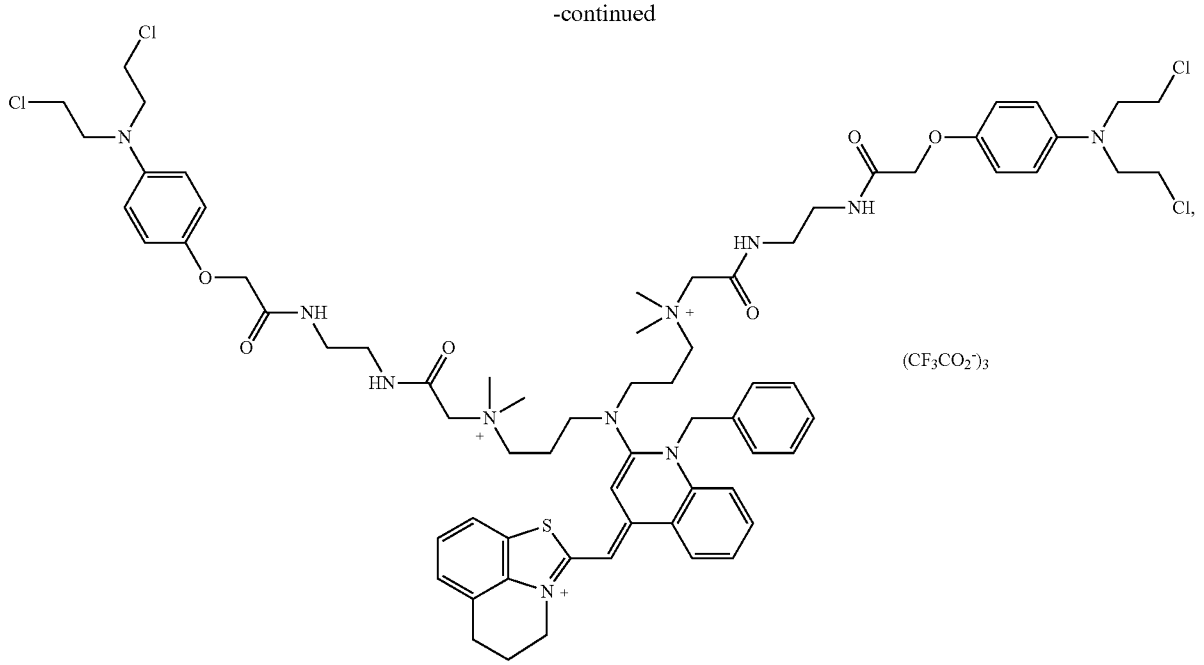

$(CF_3CO_2^-)_3$ and a salt of any thereof.

5. A method of detecting a viable microorganism or cell in a sample, the method comprising:

(a) contacting the sample with a compound of claim 1, or a salt thereof, to form a first mixture;

(b) contacting the first mixture with an inactivating agent to form a second mixture; and (c) amplifying nucleic acids from the second mixture to produce a detectable signal, wherein the signal is indicative of the presence of a viable microorganism or cell in the sample.

6. The method of claim 5, wherein the method does not include a photoactivation step and/or a culturing step.

7. The method of claim 5, wherein the inactivating agent is selected from cysteine, glutathione, a dNTP, guanine, an amine-containing buffer, and a mixture of any thereof.

8. The method of claim 5, wherein step (c) comprises:

(i) lysing cells in the second mixture to form a lysed sample;

(ii) optionally removing contaminants and/or cellular debris from the lysed sample;

(iii) adding a DNA polymerase and amplification reagents to the lysed sample to form a mixture; and (iv) subjecting the mixture to a thermal cycling protocol to amplify the nucleic acid from the sample.

9. The method of claim 5, wherein the detectable signal is a fluorescent signal.

10. The method of claim 5, wherein the microorganism is a bacterium, a virus, a fungus, a yeast, a mammalian cell, or a plant cell.

11. A method of amplifying a nucleic acid from a sample, the method comprising:

(a) contacting the sample with a compound of claim 1, or a salt thereof, to form a first mixture;

(b) contacting the first mixture with an inactivating agent to form a second mixture; and (c) amplifying nucleic acids from the second mixture.

12. A method of removing nucleic acids from a sample, the method comprising:

contacting the sample with a compound of claim 1, or a salt thereof.

13. A system or kit comprising a compound of claim 1, or a salt thereof, and further comprising a DNA polymerase, one or more amplification reagents, and/or forward and reverse primers for a target nucleic acid sequence of an organism or cell selected from a bacterium, a virus, a yeast, a fungi, a mammalian cell, or a plant cell.

* * * * *